United States Patent
Weigel et al.

(10) Patent No.: US 9,956,541 B2
(45) Date of Patent: May 1, 2018

(54) METHODS OF SEPARATING AROMATIC COMPOUNDS FROM LUBE BASE STOCKS

(71) Applicants: Scott J. Weigel, Allentown, PA (US); Lei Zhang, Basking Ridge, NJ (US); Quanchang Li, Dayton, NJ (US); Darryl Donald Lacy, Easton, PA (US); Paul Podsiadlo, Easton, PA (US); David Charles Calabro, Bridgewater, NJ (US); Bal Kaul, Fairfax, VA (US); James William Gleeson, Burke, VA (US)

(72) Inventors: Scott J. Weigel, Allentown, PA (US); Lei Zhang, Basking Ridge, NJ (US); Quanchang Li, Dayton, NJ (US); Darryl Donald Lacy, Easton, PA (US); Paul Podsiadlo, Easton, PA (US); David Charles Calabro, Bridgewater, NJ (US); Bal Kaul, Fairfax, VA (US); James William Gleeson, Burke, VA (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 77 days.

(21) Appl. No.: 14/966,790

(22) Filed: Dec. 11, 2015

(65) Prior Publication Data
US 2016/0168484 A1 Jun. 16, 2016

Related U.S. Application Data

(60) Provisional application No. 62/091,071, filed on Dec. 12, 2014, provisional application No. 62/091,077, filed on Dec. 12, 2014.

(51) Int. Cl.
*C07C 7/12* (2006.01)
*B01J 20/26* (2006.01)
(Continued)

(52) U.S. Cl.
CPC ............ *B01J 20/262* (2013.01); *B01D 15/00* (2013.01); *B01D 53/02* (2013.01); *B01D 53/04* (2013.01);
(Continued)

(58) Field of Classification Search
CPC .......... C10G 25/003; B01D 2257/7027; B01D 15/00; C08G 77/26
(Continued)

(56) References Cited

U.S. PATENT DOCUMENTS 3,178,392 A   4/1965   Kriner
4,218,308 A   8/1980   Itoh et al.
(Continued)

FOREIGN PATENT DOCUMENTS

CN   101804335 A   8/2010
CN   101980013 A   2/2011
(Continued)

OTHER PUBLICATIONS

Grudzien, R.M.; Pikus, S.; Jaroniec, M. "Periodic Mesoporous Organosilicas with Im3m Symmetry and Large Isocyanurate Bridging Groups", J. Phys. Chem. B. (2006), 110, pp. 2972-2975.*
(Continued)

*Primary Examiner* — Philip Y Louie
*Assistant Examiner* — Aaron W Pierpont
(74) *Attorney, Agent, or Firm* — Scott F. Yarnell

(57) ABSTRACT

Methods are provided herein for separating an aromatic compound from a lube base stock by contacting a lube base stock containing an aromatic compound with an organosilica material.

27 Claims, 3 Drawing Sheets

(51) Int. Cl.
| | |
|---|---|
| B01D 15/00 | (2006.01) |
| B01J 20/06 | (2006.01) |
| B01J 20/08 | (2006.01) |
| B01J 20/10 | (2006.01) |
| B01J 20/18 | (2006.01) |
| B01D 53/04 | (2006.01) |
| B01J 20/28 | (2006.01) |
| B01J 20/286 | (2006.01) |
| B01J 20/30 | (2006.01) |
| B01J 20/32 | (2006.01) |
| B01J 29/03 | (2006.01) |
| C01B 37/00 | (2006.01) |
| C08F 36/04 | (2006.01) |
| C08F 36/20 | (2006.01) |
| C08G 77/60 | (2006.01) |
| C08F 2/00 | (2006.01) |
| C08F 2/42 | (2006.01) |
| C10G 25/00 | (2006.01) |
| C10G 45/44 | (2006.01) |
| B01J 20/02 | (2006.01) |
| B01J 20/16 | (2006.01) |
| B01D 53/02 | (2006.01) |
| B01D 53/047 | (2006.01) |
| B01J 23/44 | (2006.01) |
| B01J 31/02 | (2006.01) |
| B01J 37/02 | (2006.01) |
| C10G 45/52 | (2006.01) |
| B01J 20/22 | (2006.01) |
| B01J 35/10 | (2006.01) |
| C07F 7/08 | (2006.01) |
| C08G 77/26 | (2006.01) |
| C10M 101/02 | (2006.01) |
| B01D 67/00 | (2006.01) |
| B01D 69/10 | (2006.01) |
| B01D 71/70 | (2006.01) |
| C10G 31/09 | (2006.01) |
| C23C 16/56 | (2006.01) |
| C08F 2/10 | (2006.01) |
| C08F 4/659 | (2006.01) |
| C08F 4/6592 | (2006.01) |

(52) U.S. Cl.
CPC ....... *B01D 53/047* (2013.01); *B01D 53/0462* (2013.01); *B01D 67/0088* (2013.01); *B01D 69/10* (2013.01); *B01D 71/70* (2013.01); *B01J 20/0229* (2013.01); *B01J 20/0237* (2013.01); *B01J 20/06* (2013.01); *B01J 20/08* (2013.01); *B01J 20/10* (2013.01); *B01J 20/103* (2013.01); *B01J 20/16* (2013.01); *B01J 20/18* (2013.01); *B01J 20/22* (2013.01); *B01J 20/264* (2013.01); *B01J 20/286* (2013.01); *B01J 20/28011* (2013.01); *B01J 20/28057* (2013.01); *B01J 20/28061* (2013.01); *B01J 20/28064* (2013.01); *B01J 20/28066* (2013.01); *B01J 20/28069* (2013.01); *B01J 20/28071* (2013.01); *B01J 20/28073* (2013.01); *B01J 20/28076* (2013.01); *B01J 20/28078* (2013.01); *B01J 20/28083* (2013.01); *B01J 20/3042* (2013.01); *B01J 20/3204* (2013.01); *B01J 20/3212* (2013.01); *B01J 20/3236* (2013.01); *B01J 20/3238* (2013.01); *B01J 20/3272* (2013.01); *B01J 23/44* (2013.01); *B01J 29/0308* (2013.01); *B01J 31/0274* (2013.01); *B01J 35/1019* (2013.01); *B01J 35/1023* (2013.01); *B01J 35/1028* (2013.01); *B01J 35/1061* (2013.01); *B01J 37/0213* (2013.01); *B01J 37/0236* (2013.01); *C01B 37/00* (2013.01); *C07F 7/0807* (2013.01); *C07F 7/0818* (2013.01); *C08F 2/00* (2013.01); *C08F 2/10* (2013.01); *C08F 2/42* (2013.01); *C08F 36/04* (2013.01); *C08F 36/20* (2013.01); *C08G 77/26* (2013.01); *C08G 77/60* (2013.01); *C10G 25/003* (2013.01); *C10G 31/09* (2013.01); *C10G 45/44* (2013.01); *C10G 45/52* (2013.01); *C10M 101/02* (2013.01); *C23C 16/56* (2013.01); *B01D 2253/20* (2013.01); *B01D 2253/25* (2013.01); *B01D 2256/245* (2013.01); *B01D 2257/302* (2013.01); *B01D 2257/304* (2013.01); *B01D 2257/40* (2013.01); *B01D 2257/504* (2013.01); *B01D 2257/80* (2013.01); *B01J 2220/86* (2013.01); *C08F 4/659* (2013.01); *C08F 4/65912* (2013.01); *C08F 4/65916* (2013.01); *C08F 4/65925* (2013.01); *C08F 4/65927* (2013.01)

(58) Field of Classification Search
USPC .................. 585/830, 804, 800, 823, 824
See application file for complete search history.

(56) References Cited

U.S. PATENT DOCUMENTS

| | | | |
|---|---|---|---|
| 4,808,300 A * | 2/1989 | Yao | C10G 25/03 208/28 |
| 5,510,564 A * | 4/1996 | Raghuram | C10G 53/08 585/802 |
| 5,630,937 A | 5/1997 | Betz et al. | |
| 5,719,322 A | 2/1998 | Lansbarkis et al. | |
| 7,300,905 B2 | 11/2007 | Keefer et al. | |
| 7,497,965 B2 | 3/2009 | Wariishi et al. | |
| 7,538,065 B2 | 5/2009 | McCarthy et al. | |
| 7,682,502 B2 | 3/2010 | McCarthy et al. | |
| 7,705,062 B2 | 4/2010 | Markowitz et al. | |
| 7,754,330 B2 | 7/2010 | Hamada et al. | |
| 7,767,620 B2 | 8/2010 | Whitnall et al. | |
| 7,947,799 B2 | 5/2011 | Landskron et al. | |
| 8,110,692 B2 | 2/2012 | Bellussi et al. | |
| 8,211,498 B2 | 7/2012 | Ku et al. | |
| 8,277,600 B2 | 10/2012 | Hamada et al. | |
| 8,277,661 B2 | 10/2012 | Sah et al. | |
| 8,425,762 B2 | 4/2013 | McCarthy et al. | |
| 8,441,006 B2 | 5/2013 | Mchalak et al. | |
| 8,470,074 B2 | 6/2013 | Baugh et al. | |
| 8,545,694 B2 | 10/2013 | McCarthy et al. | |
| 8,562,856 B2 | 10/2013 | Giannantonio et al. | |
| 8,568,520 B2 | 10/2013 | Ohashi et al. | |
| 8,598,070 B1 | 12/2013 | Baugh et al. | |
| 8,598,071 B1 | 12/2013 | Baugh et al. | |
| 8,809,561 B2 | 8/2014 | Bellussi et al. | |
| 9,181,282 B2 | 11/2015 | Ide et al. | |
| 2003/0188991 A1 | 10/2003 | Shan et al. | |
| 2005/0093189 A1 | 5/2005 | Vo | |
| 2006/0058565 A1 | 3/2006 | DeWild | |
| 2006/0070917 A1 | 4/2006 | McCarthy et al. | |
| 2006/0165574 A1 | 7/2006 | Sayari | |
| 2007/0034992 A1 | 2/2007 | Wariishi et al. | |
| 2007/0054136 A1 | 3/2007 | Takahashi et al. | |
| 2007/0112242 A1 | 5/2007 | Edmiston | |
| 2007/0173401 A1* | 7/2007 | Landskron | B01J 29/0308 502/232 |
| 2009/0130412 A1 | 5/2009 | Hatton et al. | |
| 2009/0215612 A1 | 8/2009 | McCarthy et al. | |
| 2009/0294922 A1 | 12/2009 | Hamada et al. | |
| 2010/0155302 A1 | 6/2010 | Kaminsky et al. | |
| 2010/0233482 A1 | 9/2010 | Hamada et al. | |
| 2011/0139685 A1 | 6/2011 | McCarthy et al. | |
| 2012/0059181 A1 | 3/2012 | Bellussi et al. | |
| 2012/0160742 A1 | 6/2012 | Sohn et al. | |

(56) References Cited

U.S. PATENT DOCUMENTS

| | | | |
|---|---|---|---|
| 2013/0075876 | A1 | 3/2013 | Goethals et al. |
| 2013/0078172 | A1 | 3/2013 | Li et al. |
| 2013/0249049 | A1 | 9/2013 | Michalak et al. |
| 2014/0004358 | A1 | 1/2014 | Blackwell et al. |
| 2014/0186246 | A1 | 7/2014 | Calabro et al. |
| 2014/0208753 | A1 | 7/2014 | Liu et al. |
| 2015/0011787 | A1 | 1/2015 | Bellussi et al. |

FOREIGN PATENT DOCUMENTS

| | | | |
|---|---|---|---|
| CN | 102052713 | A | 5/2011 |
| CN | 102643429 | A | 8/2012 |
| CN | 103157362 | A | 6/2013 |
| CN | 103495340 | A | 1/2014 |
| CN | 103613975 | A | 3/2014 |
| CN | 104117343 | A | 10/2014 |
| EP | 1995214 | A2 | 11/2008 |
| JP | H10151343 | A | 6/1998 |
| JP | H11295284 | A | 10/1999 |
| JP | 2003167233 | A | 6/2003 |
| JP | 2006083311 | A | 3/2006 |
| JP | 2006095512 | A | 4/2006 |
| JP | 2007070520 | A | 3/2007 |
| JP | 2007238761 | A | 9/2007 |
| JP | 2008045060 | A | 2/2008 |
| JP | 2008062138 | A | 3/2008 |
| JP | 2010100492 | A | 5/2010 |
| JP | 2011025201 | A | 2/2011 |
| JP | 2012149138 | A | 8/2012 |
| JP | 2014057941 | A | 4/2014 |
| JP | 5544672 | B1 | 7/2014 |
| RU | 2291878 | C1 | 1/2007 |
| WO | 9610537 | A1 | 4/1996 |
| WO | 2006032140 | A1 | 3/2006 |
| WO | 2007081212 | A1 | 7/2007 |
| WO | 2011145933 | A1 | 11/2011 |
| WO | 2013093022 | A1 | 6/2013 |
| WO | 2014010512 | A1 | 1/2014 |
| WO | 2014090757 | A1 | 6/2014 |

OTHER PUBLICATIONS

Russo, P.A . Carrott, M.L.R.; Carrot, P.J.M. "Hydrocarbons adsorption on templated mesoporous materials: effect of the pore size, geometry and surface chemistry", New J. Chem. (2011), 35, pp. 407-416.*

Lin, D.; Hu, L.; Li, Z.; Loy, D.A. "Influence of alkylene-bridging group length on mesostructured and porosity in cubic (Pm3n) periodic mesoporous bridged polysilsesquioxanes", J. Porous Mater. (Sep. 14, 2014), 21: pp. 39-44.*

Libowitz, G.G.; Whittingham, M.S. "Materials Science in Energy Technology", Academic Press: New York (1979); p. 11.*

Topchiev et al., "Preparation of hexa alkoxy derivatives of cyclotrimethylenesilane", Doklady Akademii Nauk SSSR, 1955, pp. 95-96. vol. 103.

Kriner, "The preparation of cyclic siliconmethylene compounds", Journal of Organic Chemistry, 1964-06, pp. 1601-1606, vol. 29.

Kuivila et al., "Trimethylsilyl-substituted norbornenes, norbornanes, and nortricyclene", Journal of Organic Chemistry, 1964-10, pp. 2845-2851, vol. 29.

Vidal-Madjar et al., "Fast Analysis of Geometrical Isomers of Complex Compounds by Gas-Solid Chromatography", Gas Chromatography, Sep. 28, 1970-Oct. 2, 1970, pp. 381-386.

Niemeyer et al., "Effects of CO2 Sorption on the Rotational Reorientation Dynamics of a Model Solute Dissolved in Molten Poly(dimethylsiloxane)", Macromolecules, Jan. 13, 1998, pp. 77-85, vol. 31.

Shinji et al., "Novel Mesoporous Materials with a Uniform Distribution of Organic Groups and Inorganic Oxide in Their Frameworks", Journal of the American Chemical Society, Oct. 4, 1999, pp. 9611-9614, vol. 121.

Melde et al., "Mesoporous Sieves with Unified Hybrid Inorganic/Organic Frameworks", Chemistry of Materials, Oct. 9, 1999, pp. 3302-3308, vol. 11.

Eliseeva et al., "Antifoaming additive for alkaline absorption solutions for removal of carbon dioxide from synthesis gas", Khimicheskaya Promyshlennost, 1999, pp. 632-633, vol. 10.

Brondani, et al., "Polyfunctional carbosilanes and organosilicon compounds. Synthesis via Grignard reactions", Tetrahedron Letters, Mar. 2, 2001, pp. 2111-2114, vol. 34.

Gilman et al., "Reactions of triphenylsilyllithium with some dichloropropenes", Journal of Organometallic Chemistry, Apr. 13, 2001, pp. 293-303, vol. 2.

Landskron et al., "Periodic Mesoporous Organosilicas Containing Interconnected [Si(CH2)]3 Rings", Science, Oct. 10, 2003, pp. 266-269, vol. 302.

Harlick et al., "Applications of Pore-Expanded Mesoporous Silica. 5. Triamine Grafted Material with Exceptional CO2 Dynamic and Equilibrium Adsorption Performance", Industrial & Engineering Chemistry Research, Dec. 20, 2006, pp. 446-458 vol. 46.

Grudzien et al., "Cage-like ordered mesoporous organosilicas with isocyanurate bridging groups: Synthesis, template removal and structural properties", Microporous and Mesoporous Materials, pp. 68-77, vol. 118, No. 1-3.

Walcarius et al., "Mesoporous organosilica adsorbents: nanoengineered materials for removal of organic and inorganic pollutants", Journal of Materials Chemistry, Jan. 1, 2010, pp. 4478-4511, vol. 20, No. 22.

Vidal et al., "Adsorption of polycyclic aromatic hydrocarbons from aqueous solutions by modified periodic mesoporous organosilica", Journal of Colloid and Interface Science, Feb. 3, 2011, pp. 466-473, vol. 357, No. 2.

Goethals et al., "Ultra-low-k cyclic carbon-bridged PMO films with a high chemical resistance", Journal of Materials Chemistry, Feb. 21, 2012, pp. 8281-8286, vol. 22.

PCT/US2015/065258 Partial International Search Report and Written Opinion dated Mar. 16, 2016.

PCT/US2015/065194 International Search Report and Written Opinion dated Mar. 29, 2016.

PCT/US2015/065191 International Search Report and Written Opinion dated Mar. 29, 2016.

PCT/US2015/065306 International Search Report and Written Opinion dated Mar. 29, 2016.

PCT/US2015/065219 International Search Report and Written Opinion dated Apr. 5, 2016.

PCT/US2015/065283 International Search Report and Written Opinion dated Apr. 6, 2016.

PCT/US2015/065199 International Search Report and Written Opinion dated Apr. 8, 2016.

PCT/US2015/065204 International Search Report and Written Opinion dated Apr. 8, 2016.

PCT/US2015/065225 International Search Report and Written Opinion dated Apr. 8, 2016.

Grudzien et al., "Cage-like mesoporous organosilicas with isocyanurate bridging groups synthesized by soft templating with poly(ethylene oxide)-poly(butylene oxide)-poly(ethylene oxide) block copolymer", Journal of Colloid and Interface Science, May 1, 2009, pp. 354-362, vol. 333, No. 1, Elsevier.

Grudzien et al., "Periodic Mesoporous Organosilicas with Im3m Symmetry and Large Isocyanurate Bridging Groups", The Journal of Physical Chemistry B, Feb. 1, 2006, pp. 2972-2975, vol. 110, No. 7, ACS Publications.

Olkhovyk et al., "Periodic Mesoporous Organosilica with Large Heterocyclic Bridging Groups", Journal of American Chemical Society, Jan. 1, 2005, pp. 60-61, vol. 127, No. 1, ACS Publications.

Poli et al., "Different Routes for Preparing Mesoporous Organosilicas Containing the Troger's Base and Their Textural and Catalytic Implications", The Journal of Physical Chemistry C, Apr. 21, 2011, pp. 7573-7585, vol. 115, No. 15, ACS Publications.

PCT/US2015/065208 International Search Report and Written Opinion dated May 17, 2016.

PCT/US2015/065200 Partial International Search Report and Written Opinion dated May 23, 2016.

(56) References Cited

OTHER PUBLICATIONS

Diaz et al., "Hybrid organic-inorganic catalytic porous materials synthesized at neutral pH in absence of structural directing agents", Journal of Materials Chemistry, Jan. 1, 2009, pp. 5970-5979, vol. 19, No. 33, Royal Society of Chemistry.
Reale et al., "A fluoride-catalyzed sol-gel route to catalytically active non-ordered mesoporous silica materials in the absence of surfactants", Journal of Materials Chemistry, Jan. 1, 2005, pp. 1742-1754, vol. 15, No. 17, Royal Society of Chemistry.
PCT/US2015/065200 Partial International Search Report and Written Opinion dated Jul. 18, 2016.

\* cited by examiner

METHODS OF SEPARATING AROMATIC COMPOUNDS FROM LUBE BASE STOCKS

CROSS-REFERENCE TO RELATED APPLICATIONS

This application claims priority to U.S. Provisional Application Ser. No. 62/091,071 filed Dec. 12, 2014 and U.S. Provisional Application Ser. No. 62/091,077 filed Dec. 12, 2014, both of which are herein incorporated by reference in their entirety.

This application is also related to several other U.S. applications, filed on even date herewith and bearing Ser. No. 14/965,992 (entitled "Organosilica Materials and Uses Thereof"), Ser. No. 14/966,001 (entitled "Methods of Producing Organosilica Materials and Uses Thereof"), Ser. No. 14/966,071 (entitled "Aromatic Hydrogenation Catalysts and Uses Thereof"), Ser. No. 14/965,984 (entitled "Organosilica Materials and Uses Thereof"), Ser. No. 14/966,383 (entitled "Organosilica Materials and Uses Thereof"), Ser. No. 14/966,015 (entitled "Organosilica Materials and Uses Thereof"), Ser. No. 14/966,284 (entitled "Organosilica Materials and Uses Thereof"), Ser. No. 14/966,407 (entitled "Coating Method Using Organosilica Materials and Uses Thereof"), Ser. No. 14/966,445 (entitled "Membrane Fabrication Method Using Organosilica Materials and Uses Thereof"), and Ser. No. 14/966,534 (entitled "Adsorbent for Heteroatom Species Removal and Uses Thereof"), the entire disclosures of each of which are incorporated by reference herein.

Additionally, this application is further related to several other U.S. applications, filed on even date herewith and bearing Ser. No. 15/526,512 (entitled "Organosilica Materials for Use as Adsorbents for Oxygenate Removal"), Ser. No. 15/526,524 (entitled "Supported Catalyst for Olefin Polymerization"), Ser. No. 15/526,529 (entitled "Supported Catalyst for Olefin Polymerization"), Ser. No. 15/526,513 (entitled "Supported Catalyst for Olefin Polymerization"), and Ser. No. 15/526,521 (entitled "Supported Catalyst for Olefin Polymerization"), the entire disclosures of each of which are incorporated by reference herein.

FIELD

This disclosure relates to methods of separating aromatic compounds from lube base stocks.

BACKGROUND

Traditionally, aromatic compounds in lube range products are removed through hydrogenation or cracking chemistry. While the hydrogenation process may be able to remove a large of amount of the aromatics from lube base stocks, large multi-ring aromatics cannot be completely hydrogenated leaving at least one ring aromatics left in the product. Such one ring aromatic may cause issues with additive package solubility and/or stability used in the formulated lube product or introduce oxidative instability causing coloring of the final product. In some instances, these large compounds can be cracked open exposing the inner aromatics rings which can then be hydrogenated; however, cracking chemistry can be non-selective thereby cracking desired high molecular weight molecules resulting in product yield loss and potentially lower performance of the base stock. Thus, there is a need for a separation process (e.g., adsorption) that can separate aromatic compounds from lube base stocks. Furthermore, coupling a separation process with conventional hydroprocessing processes may produce base stocks with higher saturate levels. Highly saturated base stocks are desired in the industry since it is believed that the unsaturated species can cause significant oxidative degradation of the finished lubricants under the operating conditions found in typical engines and industrial applications.

Porous inorganic solids have found great utility as separation media for industrial application. In particular, mesoporous materials, such as silicas and aluminas, having a periodic arrangement of mesopores are attractive materials for use in adsorption and separation processes due to their uniform and tunable pores, high surface areas and large pore volumes. Such mesoporous materials are known to have large specific surface areas (e.g., 1000 $m^2/g$) and large pore volumes (e.g., 1 $cm^3/g$). For these reasons, such mesoporous materials enable molecules to rapidly diffuse into the pores and therefore, can be advantageous over zeolites, which have smaller pore sizes. Consequently, such mesoporous materials can be useful as large capacity adsorbents.

However, mesoporous organosilicas, which may be used as an adsorbent, are conventionally formed by the self-assembly of the silsequioxane precursor in the presence of a structure directing agent, a porogen and/or a framework element. The precursor is hydrolysable and condenses around the structure directing agent. These materials have been referred to as Periodic Mesoporous Organosilicates (PMOs), due to the presence of periodic arrays of parallel aligned mesoscale channels. For example, Landskron, K., et al. [*Science*, 302:266-269 (2003)] report the self-assembly of 1,3,5-tris[diethoxysila]cylcohexane [$(EtO)_2SiCH_2]_3$ in the presence of a base and the structure directing agent, cetyltrimethylammonium bromide, to form PMOs that are bridged organosilicas with a periodic mesoporous framework, which consist of $SiO_3R$ or $SiO_2R_2$ building blocks, where R is a bridging organic group. In PMOs, the organic groups can be homogenously distributed in the pore walls. U.S. Pat. Pub. No. 2012/0059181 reports the preparation of a crystalline hybrid organic-inorganic silicate formed from 1,1,3,3,5,5 hexaethoxy-1,3,5 trisilyl cyclohexane in the presence of $NaAlO_2$ and base. U.S. Patent Application Publication No. 2007/003492 reports preparation of a composition formed from 1,1,3,3,5,5 hexaethoxy-1,3,5 trisilyl cyclohexane in the presence of propylene glycol monomethyl ether.

However, the use of a structure directing agent, such as a surfactant, in the preparation of an organosilica material, requires a complicated, energy intensive process to eliminate the structure directing agent at the end of the preparation process. For example, calcining may be required as well as wastewater disposal steps and associated costs to dispose of the structure directing agent. This limits the ability to scale-up the process for industrial applications.

Therefore, there is a need for improved processes for separation of aromatic compounds from hydrocarbon feeds using organosilica materials that can be prepared by a method that can be practiced in the absence of a structure directing agent, a porogen or surfactant.

SUMMARY

It has been found that aromatic compounds can be separated from lube base stocks using organosilica materials. Further, such organosilica materials can be successfully prepared without the need for a structure directing agent, a porogen or surfactant.

Thus, in one aspect, embodiments of the disclosure provide a method for separating an aromatic compound from a lube base stock, the method comprising contacting a lube base stock containing an aromatic compound with an organosilica material, which is a polymer of at least one monomer selected from the group consisting of: (a) a monomer of Formula $[Z^1OZ^2OSiCH_2]_3$ (I), wherein $Z^1$ and $Z^2$ each independently represent a hydrogen atom, a $C_1$-$C_4$ alkyl group, or a bond to a silicon atom of another monomer; and (b) a cyclic polyurea monomer of Formula

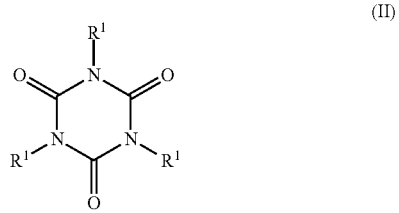

(II)

wherein each $R^1$ independently is a $X^1OX^2X^3SiX^4$ group, wherein each $X^1$ represents a hydrogen atom, a $C_1$-$C_4$ alkyl group, or a bond to a silicon atom of another monomer unit; $X^2$ and $X^3$ each independently represent a hydroxyl group, a $C_1$-$C_4$ alkyl group, a $C_1$-$C_4$ alkoxy group, or an oxygen atom bonded to a silicon atom of another monomer unit; and each $X^4$ represents a $C_1$-$C_8$ alkylene group bonded to a nitrogen atom of the cyclic polyurea.

In still another aspect, embodiments of the disclosure provide an at least partially purified lube base made by the method of any one of the previous claims.

Other embodiments, including particular aspects of the embodiments summarized above, will be evident from the detailed description that follows.

DETAILED DESCRIPTION

Figure 1:
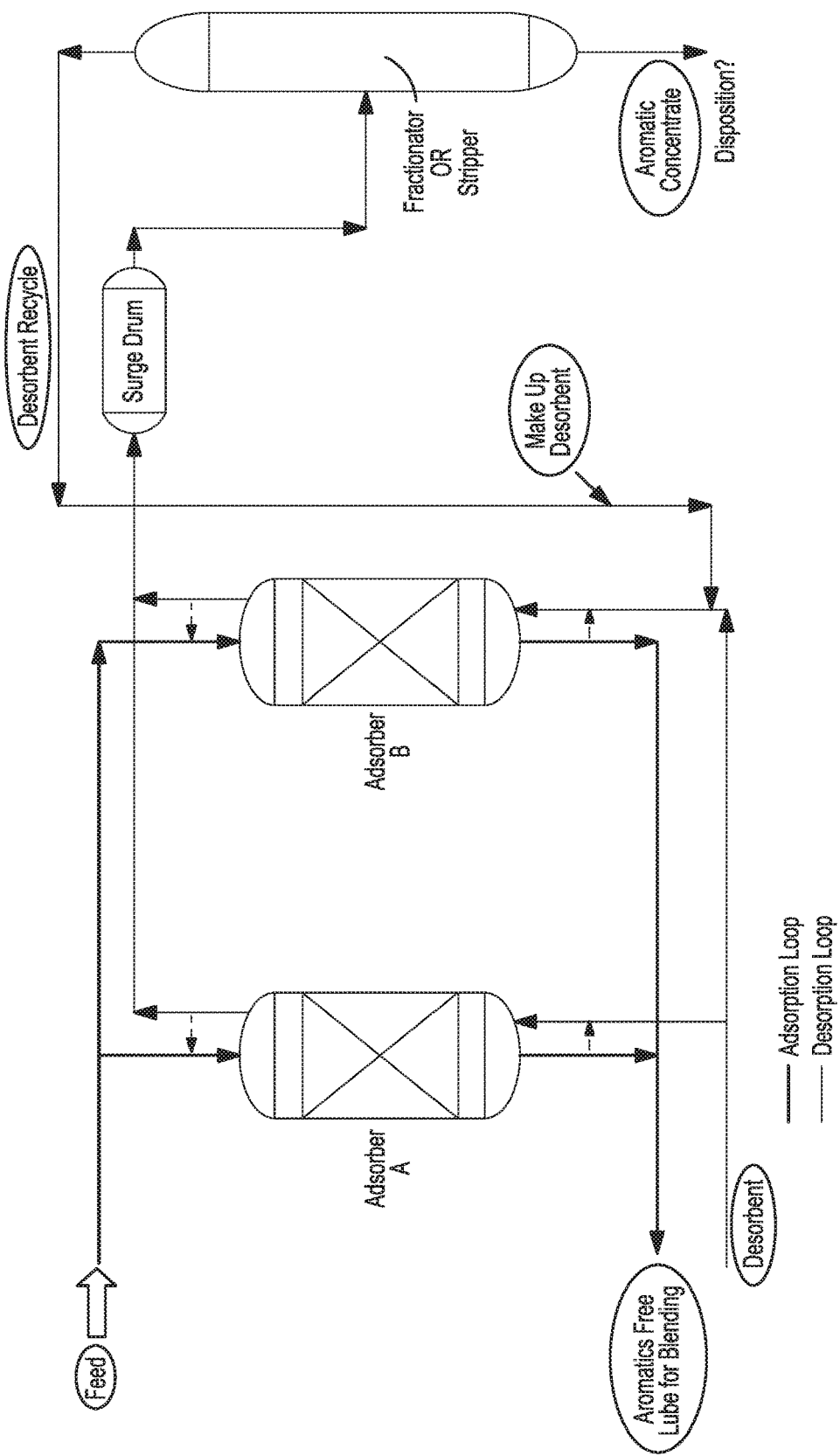
FIG. 1 illustrates a flow scheme for trimming aromatics from lube oil.

In various aspects of the disclosure, methods for separating aromatic compounds with organosilica materials and methods for preparing organosilica materials and aromatics processes are provided.

I. Definitions

All numerical values within the detailed description and the claims herein are modified by "about" or "approximately" the indicated value, and take into account experimental error and variations that would be expected by a person having ordinary skill in the art.

For purposes of this disclosure and the claims hereto, the numbering scheme for the Periodic Table Groups is according to the IUPAC Periodic Table of Elements.

The term "and/or" as used in a phrase such as "A and/or B" herein is intended to include "A and B", "A or B", "A", and "B".

The terms "substituent", "radical", "group", and "moiety" may be used interchangeably.

As used herein, and unless otherwise specified, the term "$C_n$" means hydrocarbon(s) having n carbon atom(s) per molecule, wherein n is a positive integer.

As used herein, and unless otherwise specified, the term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

As used herein, and unless otherwise specified, the term "alkyl" refers to a saturated hydrocarbon radical having from 1 to 12 carbon atoms (i.e. $C_1$-$C_{12}$ alkyl), particularly from 1 to 8 carbon atoms (i.e. $C_1$-$C_8$ alkyl), particularly from 1 to 6 carbon atoms (i.e. $C_1$-$C_6$ alkyl), and particularly from 1 to 4 carbon atoms (i.e. $C_1$-$C_4$ alkyl). Examples of alkyl groups include, but are not limited to, methyl, ethyl, propyl, butyl, pentyl, hexyl, heptyl, octyl, decyl, and so forth. The alkyl group may be linear, branched or cyclic. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl and so forth. As used herein, "$C_1$ alkyl" refers to methyl (—$CH_3$), "$C_2$ alkyl" refers to ethyl (—$CH_2CH_3$), "$C_3$ alkyl" refers to propyl (—$CH_2CH_2CH_3$) and "$C_4$ alkyl" refers to butyl (e.g. —$CH_2CH_2CH_2CH_3$, —($CH_3$)$CHCH_2CH_3$, —$CH_2CH$($CH_3$)$_2$, etc.). Further, as used herein, "Me" refers to methyl, and "Et" refers to ethyl, "i-Pr" refers to isopropyl, "t-Bu" refers to tert-butyl, and "Np" refers to neopentyl.

As used herein, and unless otherwise specified, the term "alkylene" refers to a divalent alkyl moiety containing 1 to 12 carbon atoms (i.e. $C_1$-$C_{12}$ alkylene) in length and meaning the alkylene moiety is attached to the rest of the molecule at both ends of the alkyl unit. For example, alkylenes include, but are not limited to, —$CH_2$—, —$CH_2CH_2$—, —$CH(CH_3)CH_2$—, —$CH_2CH_2CH_2$—, etc. The alkylene group may be linear or branched.

As used herein, and unless otherwise specified, the term "nitrogen-containing alkyl" refers to an alkyl group as defined herein wherein one or more carbon atoms in the alkyl group is substituted with a nitrogen atom or a nitrogen-containing cyclic hydrocarbon having from 2 to 10 carbon atoms (i.e., a nitrogen-containing cyclic $C_2$-$C_{10}$ hydrocarbon), particularly having from 2 to 5 carbon atoms (i.e., a nitrogen-containing cyclic $C_2$-$C_5$ hydrocarbon), and particularly having from 2 to 5 carbon atoms (i.e., a nitrogen-containing cyclic $C_2$-$C_5$ hydrocarbon). The nitrogen-containing cyclic hydrocarbon may have one or more nitrogen atoms. The nitrogen atom(s) may optionally be substituted with one or two $C_1$-$C_6$ alkyl groups. The nitrogen-containing alkyl can have from 1 to 12 carbon atoms (i.e. $C_1$-$C_{12}$ nitrogen-containing alkyl), particularly from 1 to 10 carbon atoms (i.e. $C_1$-$C_{10}$ nitrogen-containing alkyl), particularly from 2 to 10 carbon atoms (i.e. $C_2$-$C_{10}$ nitrogen-containing alkyl), particularly from 3 to 10 carbon atoms (i.e. $C_3$-$C_{10}$ nitrogen-containing alkyl), and particularly from 3 to 8 carbon atoms (i.e. $C_1$-$C_{10}$ nitrogen-containing alkyl). Examples of nitrogen-containing alkyls include, but are not limited to,

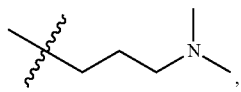

,

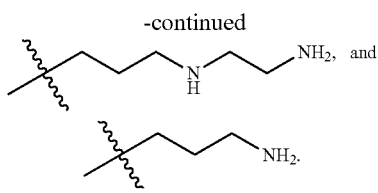

As used herein, and unless otherwise specified, the term "nitrogen-containing alkylene" refers to an alkylene group as defined herein wherein one or more carbon atoms in the alkyl group is substituted with a nitrogen atom. The nitrogen atom(s) may optionally be substituted with one or two $C_1$-$C_6$ alkyl groups. The nitrogen-containing alkylene can have from 1 to 12 carbon atoms (i.e. $C_1$-$C_{12}$ nitrogen-containing alkylene), particularly from 2 to 10 carbon atoms (i.e. $C_2$-$C_{10}$ nitrogen-containing alkylene), particularly from 3 to 10 carbon atoms (i.e. $C_3$-$C_{10}$ nitrogen-containing alkylene), particularly from 4 to 10 carbon atoms (i.e. $C_4$-$C_{10}$ nitrogen-containing alkylene), and particularly from 3 to 8 carbon atoms (i.e. $C_3$-$C_8$ nitrogen-containing alkyl). Examples of nitrogen-containing alkylenes include, but are not limited to,

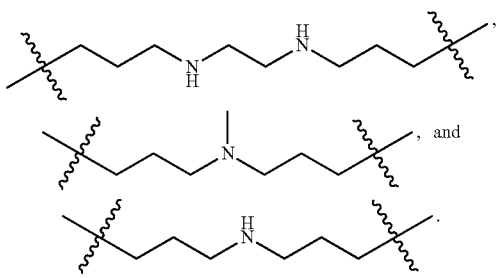

As used herein, and unless otherwise specified, the term "alkenyl" refers to an unsaturated hydrocarbon radical having from 2 to 12 carbon atoms (i.e., $C_2$-$C_{12}$ alkenyl), particularly from 2 to 8 carbon atoms (i.e., $C_2$-$C_8$ alkenyl), particularly from 2 to 6 carbon atoms (i.e., $C_2$-$C_6$ alkenyl), and having one or more (e.g., 2, 3, etc.) carbon-carbon double bonds. The alkenyl group may be linear, branched or cyclic. Examples of alkenyls include, but are not limited to ethenyl (vinyl), 2-propenyl, 3-propenyl, 1,4-pentadienyl, 1,4-butadienyl, 1-butenyl, 2-butenyl and 3-butenyl. "Alkenyl" is intended to embrace all structural isomeric forms of an alkenyl. For example, butenyl encompasses 1,4-butadienyl, 1-butenyl, 2-butenyl and 3-butenyl, etc.

As used herein, and unless otherwise specified, the term "alkenylene" refers to a divalent alkenyl moiety containing 2 to about 12 carbon atoms (i.e. $C_2$-$C_{12}$ alkenylene) in length and meaning that the alkylene moiety is attached to the rest of the molecule at both ends of the alkyl unit. For example, alkenylenes include, but are not limited to, —CH═CH—, —CH═CHCH$_2$—, —CH═CH═CH—, —CH$_2$CH$_2$CH═CHCH$_2$—, etc. —CH$_2$CH$_2$—, —CH(CH$_3$)CH$_2$—, —CH$_2$CH$_2$CH$_2$—, etc. The alkenylene group may be linear or branched.

As used herein, and unless otherwise specified, the term "alkynyl" refers to an unsaturated hydrocarbon radical having from 2 to 12 carbon atoms (i.e., $C_2$-$C_{12}$ alkynyl), particularly from 2 to 8 carbon atoms (i.e., $C_2$-$C_8$ alkynyl), particularly from 2 to 6 carbon atoms (i.e., $C_2$-$C_6$ alkynyl), and having one or more (e.g., 2, 3, etc.) carbon-carbon triple bonds. The alkynyl group may be linear, branched or cyclic. Examples of alkynyls include, but are not limited to ethynyl, 1-propynyl, 2-butynyl, and 1,3-butadiynyl. "Alkynyl" is intended to embrace all structural isomeric forms of an alkynyl. For example, butynyl encompassses 2-butynyl, and 1,3-butadiynyl and propynyl encompasses 1-propynyl and 2-propynyl (propargyl).

As used herein, and unless otherwise specified, the term "alkynylene" refers to a divalent alkynyl moiety containing 2 to about 12 carbon atoms (i.e. $C_2$-$C_{12}$ alkenylene) in length and meaning that the alkylene moiety is attached to the rest of the molecule at both ends of the alkyl unit. For example, alkenylenes include, but are not limited to, —C≡C—, —C≡CCH$_2$—, —C≡CCH$_2$C≡C—, —CH$_2$CH$_2$C≡CCH$_2$—, etc. —CH$_2$CH$_2$—, —CH(CH$_3$)CH$_2$—, —CH$_2$CH$_2$CH$_2$—, etc. The alkynlene group may be linear or branched.

As used herein, and unless otherwise specified, the term "alkoxy" refers to —O-alkyl containing from 1 to about 10 carbon atoms. The alkoxy may be straight-chain or branched-chain. Non-limiting examples include methoxy, ethoxy, propoxy, butoxy, isobutoxy, tert-butoxy, pentoxy, and hexoxy. "$C_1$ alkoxy" refers to methoxy, "$C_2$ alkoxy" refers to ethoxy, "$C_3$ alkoxy" refers to propoxy and "$C_4$ alkoxy" refers to butoxy. Further, as used herein, "OMe" refers to methoxy and "OEt" refers to ethoxy.

As used herein, and unless otherwise specified, the term "aromatic" refers to unsaturated cyclic hydrocarbons having a delocalized conjugated π system and having from 5 to 20 carbon atoms (aromatic $C_5$-$C_{20}$ hydrocarbon), particularly from 5 to 12 carbon atoms (aromatic $C_5$-$C_{12}$ hydrocarbon), and particularly from 5 to 10 carbon atoms (aromatic $C_5$-$C_{12}$ hydrocarbon). Exemplary aromatics include, but are not limited to benzene, toluene, xylenes, me sitylene, ethylbenzenes, cumene, naphthalene, methylnaphthalene, dimethylnaphthalenes, ethylnaphthalenes, acenaphthalene, anthracene, phenanthrene, tetraphene, naphthacene, benzanthracenes, fluoranthrene, pyrene, chrysene, triphenylene, and the like, and combinations thereof. Additionally, the aromatic may comprise one or more heteroatoms. Examples of heteroatoms include, but are not limited to, nitrogen, oxygen, and/or sulfur. Aromatics with one or more heteroatom include, but are not limited to furan, benzofuran, thiophene, benzothiophene, oxazole, thiazole and the like, and combinations thereof. The aromatic may comprise monocyclic, bicyclic, tricyclic, and/or polycyclic rings (in some embodiments, at least monocyclic rings, only monocyclic and bicyclic rings, or only monocyclic rings) and may be fused rings.

As used herein, and unless otherwise specified, the term "aryl" refers to any monocyclic or polycyclic cyclized carbon radical containing 6 to 14 carbon ring atoms, wherein at least one ring is an aromatic hydrocarbon. Examples of aryls include, but are not limited to phenyl, naphthyl, pyridinyl, and indolyl.

As used herein, and unless otherwise specified, the term "aralkyl" refers to an alkyl group substituted with an aryl group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of aralkyl groups include, but are not limited to phenymethyl, phenylethyl, and naphthylmethyl. The aralkyl may comprise one or more heteroatoms and be referred to as a "heteroaralkyl." Examples of heteroatoms include, but are not limited to, nitrogen (i.e., nitrogen-containing heteroaralkyl), oxygen (i.e., oxygen-containing heteroaralkyl), and/or sulfur (i.e., sulfur-containing heteroaralkyl). Examples of heteroaralkyl groups include, but are not limited to, pyridinylethyl, indolylmethyl, furylethyl, and quinolinylpropyl.

As used herein, and unless otherwise specified, the term "heterocyclo" refers to fully saturated, partially saturated or unsaturated or polycyclic cyclized carbon radical containing from 4 to 20 carbon ring atoms and containing one or more heteroatoms atoms. Examples of heteroatoms include, but are not limited to, nitrogen (i.e., nitrogen-containing heterocyclo), oxygen (i.e., oxygen-containing heterocyclo), and/or sulfur (i.e., sulfur-containing heterocyclo). Examples of heterocyclo groups include, but are not limited to, thienyl, furyl, pyrrolyl, piperazinyl, pyridyl, benzoxazolyl, quinolinyl, imidazolyl, pyrrolidinyl, and piperidinyl.

As used herein, and unless otherwise specified, the term "heterocycloalkyl" refers to an alkyl group substituted with heterocyclo group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of heterocycloalkyl groups include, but are not limited to thienylmethyl, furylethyl, pyrrolylmethyl, piperazinylethyl, pyridylmethyl, benzoxazolylethyl, quinolinylpropyl, and imidazolylpropyl.

As used herein, the term "hydroxyl" refers to an —OH group.

As used herein, the term "mesoporous" refers to solid materials having pores that have a diameter within the range of from about 2 nm to about 50 nm.

As used herein, the term "organosilica" refers to an organosiloxane compound that comprises one or more organic groups bound to two or more Si atoms.

As used herein, the term "silanol" refers to a Si—OH group.

As used herein, the term "silanol content" refers to the percent of the Si—OH groups in a compound and can be calculated by standard methods, such as NMR.

As used herein, the terms "structure directing agent," "SDA," and/or "porogen" refer to one or more compounds added to the synthesis media to aid in and/or guide the polymerization and/or polycondensing and/or organization of the building blocks that form the organosilica material framework. Further, a "porogen" is understood to be a compound capable of forming voids or pores in the resultant organosilica material framework. As used herein, the term "structure directing agent" encompasses and is synonymous and interchangeable with the terms "templating agent" and "template."

As used herein, and unless otherwise specified, the term "adsorption" includes physisorption, chemisorption, and condensation onto a solid material and combinations thereof.

As used herein, and unless otherwise specified, the term "lube base stock" refers to hydrocarbons in the lube base stock range that have acceptable viscosity index and viscosity, cloud point, pour point, aromatic content, and color for use in making finished lubes. Lube base stocks are mixed with additives to form finished lubes. The term "lube base stock range" refers to materials with a boiling point range between about 500° F. and about 1100° F. (260° C.-600° C.). Lube base stocks can be either paraffinic or napthenic in nature depending on the chemical structure of the molecules. According to American Petroleum Institute's (API) classification, Group I base stocks contain less than 90 wt % saturates and/or greater than 0.03 wt % sulfur and have viscosity index greater than or equal to 80 and less than 120. Group II base stocks contain greater than or equal to 90 wt % saturates and less than or equal to 0.03 wt % sulfur and have viscosity index greater than or equal to 80 and less than 120. Group III base stocks contain greater than or equal to 90 wt % saturates and less than or equal to 0.03 wt % sulfur and have viscosity index greater than or equal to 120. Group IV base stocks are polyalphaolefins (PAO). Group V base stocks include all other base stocks not included in Group I, II, III, IV.

II. Methods for Separating Aromatic Compounds

The disclosure relates to methods for separating aromatic compounds from hydrocarbon feedstreams, particularly from lube base stocks. In a first embodiment, a method for separating an aromatic compound from a lube base stock is provided. The method comprises contacting a lube base stock containing an aromatic compound with an organosilica material, which is a polymer of at least one monomer selected from the group consisting of: (a) a monomer of Formula $[Z^1OZ^2OSiCH_2]_3$ (I), wherein $Z^1$ and $Z^2$ each independently represent a hydrogen atom, a $C_1$-$C_4$ alkyl group, or a bond to a silicon atom of another monomer; and a cyclic polyurea monomer of Formula

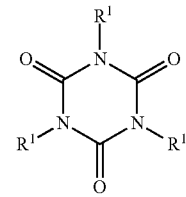

(II)

wherein each $R^1$ independently is a $X^1OX^2X^3SiX^4$ group, wherein each $X^1$ represents a hydrogen atom, a $C_1$-$C_4$ alkyl group, or a bond to a silicon atom of another monomer unit; $X^2$ and $X^3$ each independently represent a hydroxyl group, a $C_1$-$C_4$ alkyl group, a $C_1$-$C_4$ alkoxy group, or an oxygen atom bonded to a silicon atom of another monomer unit; and each $X^4$ represents a $C_1$-$C_8$ alkylene group bonded to a nitrogen atom of the cyclic polyurea.

As used herein, and unless otherwise specified, "a bond to a silicon atom of another monomer" means the bond can advantageously displace a moiety (particularly an oxygen-containing moiety such as a hydroxyl, an alkoxy or the like), if present, on a silicon atom of the another monomer so there may be a bond directly to the silicon atom of the another monomer thereby connecting the two monomers, e.g., via a Si—O—Si linkage. As used herein, and unless otherwise specified, "an oxygen atom bonded to a silicon atom of another monomer" means the oxygen atom can advantageously displace a moiety (particularly an oxygen-containing moiety such as a hydroxyl, an alkoxy or the like), if present, on a silicon atom of the another monomer so there may be an oxygen atom bonded directly to the silicon atom of the another monomer thereby connecting the two monomers, e.g., via a Si—O—Si linkage. For clarity, in these bonding scenarios, the "another monomer" can be a monomer of the same type or a monomer of a different type.

As used herein, "separation" comprises adsorption of an aromatic compound in/onto the organosilica material as well as reaction of the aromatic compound with the organosilica material.

II.A. Hydrocarbon Feedstreams

In addition to lube base stocks, other hydrocarbon feedstreams which may be suitable for use in the methods described include input feeds that can be generated as a product or side-product from a previous type of hydroprocessing, such as hydrocracking for fuels or lubricant base stock production. Such feedstreams can include hydrocarbon fluids, diesel, kerosene, lubricating oil feedstreams, whole and reduced petroleum crudes, FCC tower bottoms, and mixtures of these materials. Such feedstreams can also include other distillate feedstreams such as light to heavy distillates including raw virgin distillates, wax-containing feedstreams such as feeds derived from crude oils, shale oils and tar sands. Synthetic feeds such as those derived from the Fischer-Tropsch process can also be aromatically saturated using the hydrogenation catalyst described herein. Typical wax-containing feedstocks for the preparation of lubricating base oils have initial boiling points of about 315° C. or higher, and include feeds such as whole and reduced petroleum crudes, hydrocrackates, raffinates, hydrotreated oils, gas oils (such as atmospheric gas oils, vacuum gas oils, and coker gas oils), atmospheric and vacuum residues, deasphalted oils/residua (e.g., propane deasphalted residua, brightstock, cycle oil), dewaxed oils, slack waxes and Fischer-Tropsch wax, and mixtures of these materials. Such feeds may be derived from distillation towers (atmospheric and vacuum), hydrocrackers, hydrotreaters and solvent extraction units, and may have wax contents of up to 50% or more. Preferred lubricating oil boiling range feedstreams include feedstreams which boil in the range of 600-1100° F. Diesel boiling range feedstreams include feedstreams which boil in the range of 480-660° F. Kerosene boiling range feedstreams include feedstreams which boil in the range of 350-617° F.

II.B. Aromatic Compounds

In various aspects, the aromatic compound can be a single ring aromatic, a double ring aromatic and/or a multi-ring aromatic (e.g., 3 or more rings). Examples of single ring aromatic compounds include, but are not limited to, benzene, toluene, furan, pyrrole, thiophene, pyridine, pyrazine, pyrimidine, and triazine. Examples of double ring aromatic compounds include, but are not limited to, benzothiophene, purine, benzimidazole, indazole, naphthalene, quinoline, and quinoxaline. Examples of multi-ring aromatic compounds include, but are not limited to, anthracene, acridine, phenanthrene, tetracene, chrysene, triphenylene, pyrene, pentacene, coronene, and corannulene.

An aromatic compound may be removed from the hydrocarbon feedstream (e.g., lube base stock) in an amount of at least about 0.05 wt %, at least about 0.1 wt %, at least about 0.5 wt %, at least about 1.0 wt %, at least about 10 wt %, at least about 15 wt %, at least about 20 wt %, at least about 25 wt %, at least about 30 wt %, at least about 35 wt %, at least about 40 wt %, at least about 45 wt %, or at least about 50 wt %. In particular, at least about 0.1 wt % of the aromatic compounds is removed from the hydrocarbon feedstream (e.g., lube base stock).

Additionally or alternatively, an aromatic compound may be removed from the hydrocarbon feedstream (e.g., lube base stock) in an amount of at least about 0.05 wt % to about 35 wt %, about 0.05 wt % to about 30 wt %, about 0.05 wt % to about 25 wt %, about 0.05 wt % to about 20 wt %, about 0.05 wt % to about 15 wt %, about 0.05 wt % to about 10 wt %, about 0.05 wt % to about 5 wt %, about 0.05 wt % to about 1.0 wt %, about 0.1 wt % to about 35 wt %, about 0.1 wt % to about 30 wt %, about 0.1 wt % to about 25 wt %, about 0.1 wt % to about 20 wt %, about 0.1 wt % to about 15 wt %, about 0.1 wt % to about 10 wt %, about 0.1 wt % to about 5 wt %, about 0.1 wt % to about 1 wt %, about 1.0 wt % to about 35 wt %, about 1.0 wt % to about 30 wt %, about 1.0 wt % to about 25 wt %, about 1.0 wt % to about 20 wt %, about 1.0 wt % to about 15 wt %, or about 1.0 wt % to about 10 wt %.

II.C. Monomers of Formula (I)

In various embodiments, the organosilica material can be a polymer comprising independent units of a monomer of Formula $[Z^1OZ^2OSiCH_2]_3$ (I), wherein $Z^1$ and/or $Z^2$ each can be a hydrogen atom.

Additionally or alternatively, $Z^1$ and/or $Z^2$ each can be a $C_1$-$C_4$ alkyl group, a $C_1$-$C_3$ alkyl group, a $C_1$-$C_2$ alkyl group or methyl.

Additionally or alternatively, $Z^1$ and/or $Z^2$ each can be a bond to a silicon atom of another siloxane monomer.

Additionally or alternatively, $Z^1$ and $Z^2$ each independently can be a hydrogen atom, a $C_1$-$C_2$ alkyl group or a bond to a silicon atom of another monomer.

In a particular embodiment, $Z^1$ and $Z^2$ each independently can be a hydrogen atom, ethyl or a bond to a silicon atom of another monomer.

In another particular embodiment, $Z^1$ and $Z^2$ each independently can be a hydrogen atom or a bond to a silicon atom of another monomer.

II.D. Monomers of Formula (II)

In various embodiments, the organosilica material may further comprise another monomer, optionally in combination with independent units of Formula (I), such as another cyclic monomer of Formula

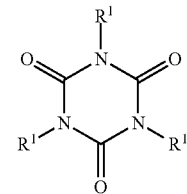

(II)

wherein each $R^1$ independently is a $X^1OX^2X^3SiX^4$ group, wherein each $X^1$ represents a hydrogen atom, a $C_1$-$C_4$ alkyl group, or a bond to a silicon atom of another monomer unit; $X^2$ and $X^3$ each independently represent a hydroxyl group, a $C_1$-$C_4$ alkyl group, a $C_1$-$C_4$ alkoxy group, or an oxygen atom bonded to a silicon atom of another monomer unit; and each $X^4$ represents a $C_1$-$C_8$ alkylene group bonded to a nitrogen atom of the cyclic polyurea.

In various embodiments, each $X^1$ can be a hydrogen atom.

Additionally or alternatively, each $X^1$ can be a $C_1$-$C_4$ alkyl group, a $C_1$-$C_3$ alkyl group, a $C_1$-$C_2$ alkyl group or methyl.

Additionally or alternatively, each $X^1$ can be a bond to a silicon atom of another siloxane monomer.

Additionally or alternatively, each $X^1$ can be a hydrogen atom, a $C_1$-$C_2$ alkyl group or a bond to a silicon atom of another monomer.

Additionally or alternatively, $X^2$ and $X^3$ each independently can be a hydroxyl group.

Additionally or alternatively, $X^2$ and $X^3$ each independently can be a $C_1$-$C_4$ alkyl group, a $C_1$-$C_3$ alkyl group, a $C_1$-$C_2$ alkyl group or methyl.

Additionally or alternatively, $X^2$ and $X^3$ each independently can be a $C_1$-$C_4$ alkoxy group, a $C_1$-$C_3$ alkoxy group, a $C_1$-$C_2$ alkoxy group or methoxy.

Additionally or alternatively, $X^2$ and $X^3$ each independently can be an oxygen atom bonded to a silicon atom of another monomer unit.

Additionally or alternatively, $X^2$ and $X^3$ each independently can be a hydroxyl group, a $C_1$-$C_2$ alkyl group, a $C_1$-$C_2$ alkoxy group, or an oxygen atom bonded to a silicon atom of another monomer unit.

Additionally or alternatively, each $X^1$ can be a hydrogen atom, a $C_1$-$C_2$ alkyl group or a bond to a silicon atom of another monomer; and $X^2$ and $X^3$ each independently can be a hydroxyl group, a $C_1$-$C_2$ alkyl group, a $C_1$-$C_2$ alkoxy group, or an oxygen atom bonded to a silicon atom of another monomer unit.

Additionally or alternatively, each $X^4$ can be a $C_1$-$C_7$ alkylene group bonded to a nitrogen atom of the cyclic polyurea, a $C_1$-$C_7$ alkylene group bonded to a nitrogen atom of the cyclic polyurea, a $C_1$-$C_6$ alkylene group bonded to a nitrogen atom of the cyclic polyurea, a $C_1$-$C_4$ alkylene group bonded to a nitrogen atom of the cyclic polyurea, a $C_1$-$C_3$ alkylene group bonded to a nitrogen atom of the cyclic polyurea, a $C_1$-$C_2$ alkylene group bonded to a nitrogen atom of the cyclic polyurea, or —$CH_2$— bonded to a nitrogen atom of the cyclic polyurea.

Additionally or alternatively, each $X^1$ can be a hydrogen atom, a $C_1$-$C_2$ alkyl group or a bond to a silicon atom of another monomer; $X^2$ and $X^3$ each independently can be a hydroxyl group, a $C_1$-$C_2$ alkyl group, a $C_1$-$C_2$ alkoxy group, or an oxygen atom bonded to a silicon atom of another monomer unit; and $X^4$ can be a $C_1$-$C_4$ alkylene group bonded to a nitrogen atom of the cyclic polyurea.

Additionally or alternatively, each $X^1$ can be a hydrogen atom or a bond to a silicon atom of another monomer; $X^2$ and $X^3$ each independently can be a hydroxyl group, a $C_1$-$C_2$ alkyl group or an oxygen atom bonded to a silicon atom of another monomer unit; and $X^4$ can be a $C_1$-$C_4$ alkylene group bonded to a nitrogen atom of the cyclic polyurea.

Additionally or alternatively, each $X^1$ can be a hydrogen atom or a bond to a silicon atom of another monomer; $X^2$ and $X^3$ each independently can be a hydroxyl group or an oxygen atom bonded to a silicon atom of another monomer unit; and $X^4$ can be a $C_1$-$C_4$ alkylene group bonded to a nitrogen atom of the cyclic polyurea.

In a particular embodiment, each $X^1$ can be a hydrogen atom, methyl, or a bond to a silicon atom of another monomer; $X^2$ and $X^3$ each independently can be a hydroxyl group, methoxy or an oxygen atom bonded to a silicon atom of another monomer unit; and $X^4$ can be —$CH_2CH_2CH_2$— bonded to a nitrogen atom of the cyclic polyurea.

In another particular embodiment, each $X^1$ can be a hydrogen atom or a bond to a silicon atom of another monomer; $X^2$ and $X^3$ each independently can be a hydroxyl group or an oxygen atom bonded to a silicon atom of another monomer unit; and $X^4$ can be —$CH_2CH_2CH_2$— bonded to a nitrogen atom of the cyclic polyurea.

In another particular embodiment, when present with independent units of Formula (I), $Z^1$ and $Z^2$ each independently can be a hydrogen atom, ethyl or a bond to a silicon atom of another monomer; each $X^1$ can be a hydrogen atom, methyl, or a bond to a silicon atom of another monomer; $X^2$ and $X^3$ each independently can be a hydroxyl group, methoxy or an oxygen atom bonded to a silicon atom of another monomer unit; and $X^4$ can be —$CH_2CH_2CH_2$— bonded to a nitrogen atom of the cyclic polyurea.

II.E. Monomers of Formula (III)

In various embodiments, the organosilica material may further comprise another monomer in combination with independent units of Formula (I) and/or independent units of Formula (II), such as another monomer having at least one independent unit of Formula $[Z^3OZ^4SiCH_2]_3$ (III), wherein each $Z^3$ represents a hydrogen atom, a $C_1$-$C_4$ alkyl group or a bond to a silicon atom of another monomer and $Z^4$ represents a $C_1$-$C_6$ alkyl group.

In various embodiments, each $Z^3$ can be a hydrogen atom.

Additionally or alternatively, each $Z^3$ can be a $C_1$-$C_4$ alkyl group, a $C_1$-$C_3$ alkyl group, a $C_1$-$C_2$ alkyl group or methyl.

Additionally or alternatively, each $Z^3$ can be a hydrogen atom or a $C_1$-$C_2$ alkyl group.

Additionally or alternatively, each $Z^3$ can be a bond to a silicon atom of another monomer.

Additionally or alternatively, each $Z^3$ can be a hydrogen atom, a $C_1$-$C_2$ alkyl group or a bond to a silicon atom of another monomer.

Additionally or alternatively, each $Z^3$ can be a hydrogen atom, ethyl or a bond to a silicon atom of another monomer.

Additionally or alternatively, each $Z^4$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^4$ can be a methyl.

Additionally or alternatively, each $Z^3$ can be a hydrogen atom, a $C_1$-$C_2$ alkyl group or a bond to a silicon atom of another monomer and each $Z^4$ can be a $C_1$-$C_4$ alkyl group.

Additionally or alternatively, each $Z^3$ can be a hydrogen atom, ethyl or a bond to a silicon atom of another monomer and each $Z^4$ can be methyl.

Additionally or alternatively, each $Z^3$ can be a hydrogen atom or a bond to a silicon atom of another monomer and each $Z^4$ can be methyl.

In another embodiment, the organosilica material support may comprise independent units of Formula $[Z^3OZ^4SiCH_2]_3$ (III) as described herein and not independent units of Formula (I) or Formula (II) as described herein. In particular, each $Z^3$ can be a hydrogen atom, ethyl or a bond to a silicon atom of another monomer and each $Z^4$ can be methyl. Additionally or alternatively, each $Z^3$ can be a hydrogen atom or a bond to a silicon atom of another monomer and each $Z^4$ can be methyl.

II.F. Monomers of Formula (IV)

In various embodiments, the organosilica material may further comprise another monomer in combination with independent units of Formula (I) and/or Formula (II), and optionally independent units of Formula (III), such as another monomer having at least one independent unit of Formula $Z^5OZ^6Z^7Z^8Si$ (IV), wherein each $Z^5$ can be a hydrogen atom, a $C_1$-$C_4$ alkyl group or a bond to a silicon atom of another monomer; and $Z^6$, $Z^7$ and $Z^8$ each independently can be selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroaralkyl group, and a nitrogen-containing optionally substituted heterocycloalkyl group, and an oxygen atom bonded to a silicon atom of another monomer.

Additionally or alternatively, each $Z^5$ can be a hydrogen atom, a $C_1$-$C_4$ alkyl group or a bond to a silicon atom of another monomer; and $Z^6$, $Z^7$ and $Z^8$ each independently can be selected from the group consisting of a hydroxyl group, a $C_1$-$C_4$ alkyl group, a $C_1$-$C_4$ alkoxy group, and an oxygen atom bonded to a silicon atom of another monomer. Additionally or alternatively, $Z^6$, $Z^7$ and $Z^8$ each independently can optionally be a nitrogen-containing $C_1$-$C_{10}$ alkyl group, a nitrogen-containing heteroaralkyl group, and/or a nitrogen-containing optionally substituted heterocycloalkyl group.

In various aspects, each $Z^5$ can be a hydrogen atom.

Additionally or alternatively, each $Z^5$ can be a $C_1$-$C_4$ alkyl group, a $C_1$-$C_3$ alkyl group, a $C_1$-$C_2$ alkyl group or methyl.

Additionally or alternatively, each $Z^5$ can be a hydrogen atom or a $C_1$-$C_2$ alkyl group.

Additionally or alternatively, each $Z^5$ can be a bond to a silicon atom of another monomer.

Additionally or alternatively, each $Z^5$ can be a hydrogen atom, a $C_1$-$C_2$ alkyl group or a bond to a silicon atom of another monomer.

Additionally or alternatively, each $Z^5$ can be a hydrogen atom, ethyl, methyl or a bond to a silicon atom of another monomer.

Additionally or alternatively, $Z^6$, $Z^7$ and $Z^8$ each independently can be a hydroxyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be a hydroxyl group.

Additionally or alternatively, $Z^6$, $Z^7$ and $Z^8$ each independently can be a $C_1$-$C_4$ alkyl group, a $C_1$-$C_3$ alkyl group, a $C_1$-$C_2$ alkyl group or methyl.

Additionally or alternatively, $Z^6$, $Z^7$ and $Z^8$ each independently can be a hydroxyl group or a $C_1$-$C_2$ alkyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be a hydroxyl group or a $C_1$-$C_2$ alkyl group.

Additionally or alternatively, $Z^6$, $Z^7$ and $Z^8$ each independently can be a $C_1$-$C_4$ alkoxy group, a $C_1$-$C_3$ alkoxy group, a $C_1$-$C_2$ alkoxy group or methoxy.

Additionally or alternatively, $Z^6$, $Z^7$ and $Z^8$ each independently can be selected from the group consisting of a hydroxyl group, a $C_1$-$C_2$ alkyl group and a $C_1$-$C_2$ alkoxy group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each can be selected from the group consisting of a hydroxyl group, a $C_1$-$C_2$ alkyl group and a $C_1$-$C_2$ alkoxy group.

Additionally or alternatively, $Z^6$, $Z^7$ and $Z^8$ each independently can optionally be a nitrogen-containing $C_1$-$C_{10}$ alkyl group, a nitrogen-containing $C_1$-$C_9$ alkyl group, a nitrogen-containing $C_1$-$C_8$ alkyl group, a nitrogen-containing $C_1$-$C_7$ alkyl group, a nitrogen-containing $C_1$-$C_6$ alkyl group, a nitrogen-containing $C_1$-$C_5$ alkyl group, a nitrogen-containing $C_1$-$C_4$ alkyl group, a nitrogen-containing $C_1$-$C_3$ alkyl group, a nitrogen-containing $C_1$-$C_2$ alkyl group, or a methylamine. In particular, $Z^6$, $Z^7$ and $Z^8$ each independently can be a nitrogen-containing $C_2$-$C_{10}$ alkyl group, a nitrogen-containing $C_3$-$C_{10}$ alkyl group, a nitrogen-containing $C_3$-$C_9$ alkyl group, or a nitrogen-containing $C_3$-$C_8$ alkyl group. The aforementioned nitrogen-containing alkyl groups may have one or more nitrogen atoms (e.g., 2, 3, etc.). Examples of nitrogen-containing $C_1$-$C_{10}$ alkyl groups include, but are not limited to,

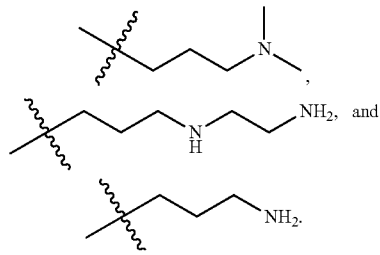

Additionally or alternatively, $Z^6$, $Z^7$ and $Z^8$ each independently can be selected from the group consisting of a hydroxyl group, a $C_1$-$C_2$ alkyl group, a $C_1$-$C_2$ alkoxy group and a nitrogen-containing $C_3$-$C_{10}$ alkyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group and a nitrogen-containing $C_3$-$C_{10}$ alkyl group.

Additionally or alternatively, $Z^6$, $Z^7$ and $Z^8$ each independently can optionally be a nitrogen-containing heteroaralkyl group. The nitrogen-containing heteroaralkyl group can be a nitrogen-containing $C_4$-$C_{12}$ heteroaralkyl group, a nitrogen-containing $C_4$-$C_{10}$ heteroaralkyl group, or a nitrogen-containing $C_4$-$C_8$ heteroaralkyl group. Examples of nitrogen-containing heteroaralkyl groups include but are not limited to pyridinylethyl, pyridinylpropyl, pyridinylmethyl, indolylmethyl, pyrazinylethyl, and pyrazinylpropyl. The aforementioned nitrogen-containing heteroaralkyl groups may have one or more nitrogen atoms (e.g., 2, 3, etc.).

Additionally or alternatively, $Z^6$, $Z^7$ and $Z^8$ each independently can be selected from the group consisting of a hydroxyl group, a $C_1$-$C_2$ alkyl group, a $C_1$-$C_2$ alkoxy group, nitrogen-containing $C_3$-$C_{10}$ alkyl group and a nitrogen-containing heteroaralkyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group, a nitrogen-containing $C_3$-$C_{10}$ alkyl group and a nitrogen-containing heteroaralkyl group.

Additionally or alternatively, $Z^6$, $Z^7$ and $Z^8$ each independently can optionally be a nitrogen-containing heterocycloalkyl group, wherein the heterocycloalkyl group may be optionally substituted with a $C_1$-$C_6$ alkyl group, particularly a $C_1$-$C_4$ alkyl group. The nitrogen-containing heterocycloalkyl group can be a nitrogen-containing $C_4$-$C_{12}$ heterocycloalkyl group, a nitrogen-containing $C_4$-$C_{10}$ heterocycloalkyl group, or a nitrogen-containing $C_4$-$C_8$ heterocycloalkyl group. Examples of nitrogen-containing heterocycloalkyl groups include but are not limited to piperazinylethyl, piperazinylpropyl, piperidinylethyl, piperidinylpropyl. The aforementioned nitrogen-containing heterocycloalkyl groups may have one or more nitrogen atoms (e.g., 2, 3, etc.).

Additionally or alternatively, $Z^6$, $Z^7$ and $Z^8$ each independently can be selected from the group consisting of a hydroxyl group, a $C_1$-$C_2$ alkyl group, a $C_1$-$C_2$ alkoxy group, nitrogen-containing $C_3$-$C_{10}$ alkyl group, a nitrogen-containing heteroaralkyl group, and a nitrogen-containing optionally substituted heterocycloalkyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group, a nitrogen-containing $C_3$-$C_{10}$ alkyl group, a nitrogen-containing heteroaralkyl group and a nitrogen-containing optionally substituted heterocycloalkyl group.

Additionally or alternatively, $Z^6$, $Z^7$ and $Z^8$ each independently optionally can be an oxygen atom bonded to a silicon atom of another monomer.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group, a nitrogen-containing $C_3$-$C_{10}$ alkyl group, a nitrogen-containing heteroaralkyl group, a nitrogen-containing optionally substituted heterocycloalkyl group and an oxygen atom bonded to a silicon atom of another monomer.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group, a nitrogen-containing $C_3$-$C_8$ alkyl group, $C_4$-$C_{10}$ heteroaralkyl group, a nitrogen-containing optionally substituted $C_4$-$C_{10}$ heterocycloalkyl group, and an oxygen atom bonded to a silicon atom of another monomer.

Additionally or alternatively, each $Z^5$ can be a hydrogen atom or a bond to a silicon atom of another monomer; and $Z^6$, $Z^7$ and $Z^8$ each independently can be selected from the group consisting of a hydroxyl group, a $C_1$-$C_2$ alkyl group, a nitrogen-containing $C_3$-$C_8$ alkyl group, $C_4$-$C_{10}$ heteroaralkyl group, a nitrogen-containing optionally substituted $C_4$-$C_{10}$ heterocycloalkyl group, and an oxygen atom bonded to a silicon atom of another monomer.

In a particular embodiment, each $Z^5$ can be a hydrogen atom, ethyl or a bond to a silicon atom of another monomer; and $Z^6$, $Z^7$ and $Z^8$ each independently can be selected from the group consisting of a hydroxyl group, ethoxy, and an oxygen atom bonded to a silicon atom of another monomer.

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and $Z^8$ can be methyl.

In another particular embodiment, each $Z^5$ can be a hydrogen atom, methyl or a bond to a silicon atom of another comonomer; $Z^6$ and $Z^7$ each independently can be selected from the group consisting of a hydroxyl group, methoxy, and an oxygen atom bonded to a silicon atom of another monomer; and each $Z^8$ can be

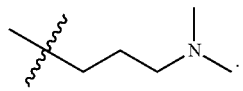 [SMILES: *CCCN(C)C]

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and each $Z^8$ can be

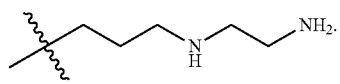 [SMILES: *CCCNCCN]

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and each $Z^8$ can be

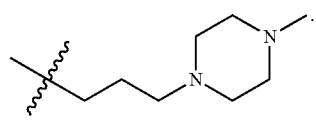 [SMILES: *CCCN1CCN(C)CC1]

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and each $Z^8$ can be

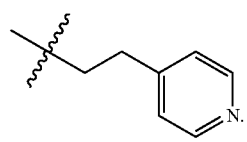 [SMILES: *CCc1ccncc1]

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and each $Z^8$ can be

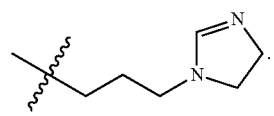 [SMILES: *CCCN1C=NCC1]

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and each $Z^8$ can be

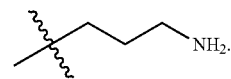 [SMILES: *CCCN]

In another embodiment, the organosilica material support may comprise independent units of Formula (III) as described herein and independent units of Formula (IV) as described herein and not independent units of Formula (I) or Formula (II) as described herein. In particular, each $Z^3$ can be a hydrogen atom, ethyl or a bond to a silicon atom of another monomer, each $Z^4$ can be methyl; each $Z^5$ can be a hydrogen atom, ethyl or a bond to a silicon atom of another monomer; and $Z^6$, $Z^7$ and $Z^8$ each independently can be selected from the group consisting of a hydroxyl group, ethoxy, and an oxygen atom bonded to a silicon atom of another monomer.

II.G. Monomers of Formula (V)

In various embodiments, the organosilica material may further comprise another monomer in combination with independent units of Formula (I) and/or Formula (II) and optionally independent units Formula (III) and/or Formula (IV), such as another monomer having at least one independent unit of Formula $Z^9Z^{10}Z^{11}Si$—R—$SiZ^9Z^{10}Z^{11}$ (V), wherein each $Z^9$ independently can be a hydroxyl group, a $C_1$-$C_4$ alkoxy group or an oxygen atom bonded to a silicon atom of another comonomer; $Z^{10}$ and $Z^{11}$ each independently can a hydroxyl group, a $C_1$-$C_4$ alkoxy group, a $C_1$-$C_4$ alkyl group or an oxygen atom bonded to a silicon atom of another monomer; and each R can be selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group.

Additionally or alternatively, each $Z^9$ independently can be a hydroxyl group, a $C_1$-$C_4$ alkoxy group or an oxygen atom bonded to a silicon atom of another comonomer; $Z^{10}$ and $Z^{11}$ each independently can a hydroxyl group, a $C_1$-$C_4$ alkoxy group, a $C_1$-$C_4$ alkyl group or an oxygen atom bonded to a silicon atom of another monomer; and each R can be selected from the group consisting a $C_1$-$C_8$ alkylene group, a $C_2$-$C_8$ alkenylene group, and a $C_2$-$C_8$ alkynylene group. Additionally or alternatively, R optionally can be a nitrogen-containing $C_1$-$C_{10}$ alkylene group, an optionally substituted $C_6$-$C_{20}$ aralkyl and/or an optionally substituted $C_4$-$C_{20}$ heterocycloalkyl group.

In various aspects, each $Z^9$ can be a hydroxyl group.

Additionally or alternatively, each $Z^9$ can be a $C_1$-$C_4$ alkoxy group, a $C_1$-$C_3$ alkoxy group, a $C_1$-$C_2$ alkoxy group or methoxy.

Additionally or alternatively, each $Z^9$ can be a hydroxyl group or a $C_1$-$C_2$ alkoxy group.

Additionally or alternatively, each $Z^9$ can be an oxygen atom bonded to a silicon atom of another comonomer.

Additionally or alternatively, each $Z^9$ can be a hydroxyl group, a $C_1$-$C_2$ alkoxy group or an oxygen atom bonded to a silicon atom of another comonomer.

Additionally or alternatively, each $Z^9$ can be a hydroxyl group or an oxygen atom bonded to a silicon atom of another comonomer.

Additionally or alternatively, $Z^{10}$ and $Z^{11}$ each independently can be a hydroxyl group.

Additionally or alternatively, $Z^{10}$ and $Z^{11}$ each independently can be a $C_1$-$C_4$ alkoxy group, a $C_1$-$C_3$ alkoxy group, a $C_1$-$C_2$ alkoxy group or methoxy.

Additionally or alternatively, $Z^{10}$ and $Z^{11}$ each independently can be a hydroxyl group or a $C_1$-$C_2$ alkoxy group.

Additionally or alternatively, $Z^{10}$ and $Z^{11}$ each independently can be a $C_1$-$C_4$ alkyl group, a $C_1$-$C_3$ alkyl group, a $C_1$-$C_2$ alkyl group or methyl.

Additionally or alternatively, $Z^{10}$ and $Z^{11}$ each independently can be a hydroxyl group, a $C_1$-$C_2$ alkoxy group, or a $C_1$-$C_2$ alkyl group.

Additionally or alternatively, $Z^{10}$ and $Z^{11}$ each independently can be an oxygen atom bonded to a silicon atom of another comonomer.

Additionally or alternatively, $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another comonomer.

Additionally or alternatively, $Z^{10}$ and $Z^{11}$ each independently can be a hydroxyl group, a $C_1$-$C_2$ alkyl group, or an oxygen atom bonded to a silicon atom of another comonomer.

Additionally or alternatively, each $Z^9$ can be a hydroxyl group, a $C_1$-$C_2$ alkoxy group or an oxygen atom bonded to a silicon atom of another comonomer; and $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another comonomer.

Additionally or alternatively, each $Z^9$ can be a hydroxyl group, ethoxy, methoxy or an oxygen atom bonded to a silicon atom of another comonomer; and $Z^{10}$ and $Z^{11}$ each independently can be a hydroxyl group, ethoxy, methyl, or an oxygen atom bonded to a silicon atom of another comonomer.

Additionally or alternatively, each $Z^9$ can be a hydroxyl group or an oxygen atom bonded to a silicon atom of another comonomer; and $Z^{10}$ and $Z^{11}$ each independently can be a hydroxyl group, methyl, or an oxygen atom bonded to a silicon atom of another comonomer.

Additionally or alternatively, each R can be a $C_1$-$C_8$ alkylene group, a $C_1$-$C_7$ alkylene group, a $C_1$-$C_6$ alkylene group, a $C_1$-$C_5$ alkylene group, a $C_1$-$C_4$ alkylene group, a $C_1$-$C_3$ alkylene group, a $C_1$-$C_2$ alkylene group or —$CH_2$—.

Additionally or alternatively, each $Z^9$ can be a hydroxyl group, a $C_1$-$C_2$ alkoxy group or an oxygen atom bonded to a silicon atom of another comonomer; $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another comonomer; and each R can be a $C_1$-$C_4$ alkylene group.

Additionally or alternatively, each R can be a $C_2$-$C_8$ alkenylene group, a $C_2$-$C_7$ alkenylene group, a $C_2$-$C_6$ alkenylene group, a $C_2$-$C_5$ alkenylene group, a $C_2$-$C_4$ alkenylene group, a $C_2$-$C_3$ alkenylene group, or —HC=CH—.

Additionally or alternatively, each $Z^9$ can be a hydroxyl group, a $C_1$-$C_2$ alkoxy group or an oxygen atom bonded to a silicon atom of another comonomer; $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another comonomer; and each R can be selected from the group consisting of a $C_1$-$C_4$ alkylene group and a $C_2$-$C_4$ alkenylene group.

Additionally or alternatively, each R can be a $C_2$-$C_8$ alkynylene group, a $C_2$-$C_7$ alkynylene group, a $C_2$-$C_6$ alkynylene group, a $C_2$-$C_5$ alkynylene group, a $C_2$-$C_4$ alkynylene group, a $C_2$-$C_3$ alkynylene group, or —C≡C—.

Additionally or alternatively, each $Z^9$ can be a hydroxyl group, a $C_1$-$C_2$ alkoxy group or an oxygen atom bonded to a silicon atom of another comonomer; $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another comonomer; and each R can be selected from the group consisting of a $C_1$-$C_4$ alkylene group, a $C_2$-$C_4$ alkenylene group and a $C_2$-$C_4$ alkynylene group.

Additionally or alternatively, each R can be a nitrogen-containing $C_2$-$C_{10}$ alkylene group, a nitrogen-containing $C_3$-$C_{10}$ alkylene group, a nitrogen-containing $C_4$-$C_{10}$ alkylene group, a nitrogen-containing $C_4$-$C_9$ alkylene group, a nitrogen-containing $C_4$-$C_8$ alkylene group, or nitrogen containing $C_3$-$C_8$ alkylene group. The aforementioned nitrogen-containing alkylene groups may have one or more nitrogen atoms (e.g., 2, 3, etc.). Examples of nitrogen-containing alkylene groups include, but are not limited to,

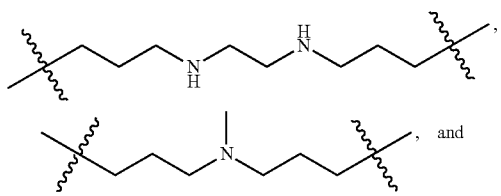

-continued

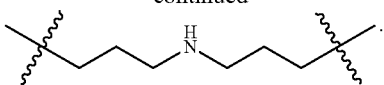

Additionally or alternatively, each $Z^9$ can be a hydroxyl group, a $C_1$-$C_2$ alkoxy group or an oxygen atom bonded to a silicon atom of another comonomer; $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another comonomer; and each R can be selected from the group consisting of a $C_1$-$C_4$ alkylene group, a $C_2$-$C_4$ alkenylene group, a $C_2$-$C_4$ alkynylene group and a nitrogen-containing $C_4$-$C_{10}$ alkylene group.

Additionally or alternatively, each R can be an optionally substituted $C_6$-$C_{20}$ aralkyl, an optionally substituted $C_6$-$C_{14}$ aralkyl, or an optionally substituted $C_6$-$C_{10}$ aralkyl. Examples of $C_6$-$C_{20}$ aralkyls include, but are not limited to, phenylmethyl, phenylethyl, and naphthylmethyl. The aralkyl may be optionally substituted with a $C_1$-$C_6$ alkyl group, particularly a $C_1$-$C_4$ alkyl group.

Additionally or alternatively, each $Z^9$ can be a hydroxyl group, a $C_1$-$C_2$ alkoxy group or an oxygen atom bonded to a silicon atom of another comonomer; $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another comonomer; and R can be selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group and an optionally substituted $C_6$-$C_{10}$ aralkyl.

Additionally or alternatively, each R can be an optionally substituted $C_4$-$C_{20}$ heterocycloalkyl group, an optionally substituted $C_4$-$C_{16}$ heterocycloalkyl group, an optionally substituted $C_4$-$C_{12}$ heterocycloalkyl group, or an optionally substituted $C_4$-$C_{10}$ heterocycloalkyl group. Examples of $C_4$-$C_{20}$ heterocycloalkyl groups include, but are not limited to, thienylmethyl, furylethyl, pyrrolylmethyl, piperazinylethyl, pyridylmethyl, benzoxazolylethyl, quinolinylpropyl, and imidazolylpropyl. The heterocycloalkyl may be optionally substituted with a $C_1$-$C_6$ alkyl group, particularly a $C_1$-$C_4$ alkyl group.

Additionally or alternatively, each $Z^9$ can be a hydroxyl group, a $C_1$-$C_2$ alkoxy group or an oxygen atom bonded to a silicon atom of another comonomer; $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another comonomer; and R can be selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl and an optionally substituted $C_4$-$C_{10}$ heterocycloalkyl group.

Additionally or alternatively, each $Z^9$ can be a hydroxyl group, ethoxy, methoxy or an oxygen atom bonded to a silicon atom of another comonomer; $Z^{10}$ and $Z^{11}$ each independently can be a hydroxyl group, ethoxy, methoxy, methyl, or an oxygen atom bonded to a silicon atom of another comonomer; and R can be selected from the group consisting of —$CH_2$—, —$CH_2CH_2$—, —HC=CH—,

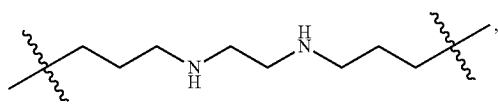

-continued

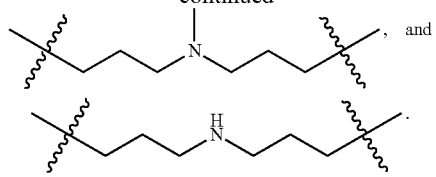

Additionally or alternatively, each $Z^9$ can be a hydroxyl group or an oxygen atom bonded to a silicon atom of another comonomer; $Z^{10}$ and $Z^{11}$ each independently can be a hydroxyl group, methyl, or an oxygen atom bonded to a silicon atom of another comonomer; and each R can be selected from the group consisting of —$CH_2$—, —$CH_2CH_2$—, —HC=CH—,

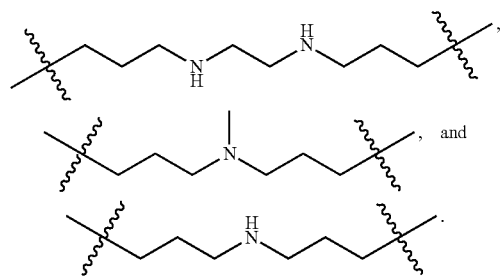

In a particular embodiment, each $Z^9$ can be a hydroxyl group, ethoxy or an oxygen atom bonded to a silicon atom of another comonomer; each $Z^{10}$ can be a hydroxyl group, ethoxy, and an oxygen atom bonded to a silicon atom of another monomer; each $Z^{11}$ can be methyl; and each R can be —$CH_2CH_2$—.

In another particular embodiment, each $Z^9$ can be a hydroxyl group, ethoxy or an oxygen atom bonded to a silicon atom of another comonomer; $Z^{10}$ and $Z^{11}$ each independently can be selected from the group consisting of a hydroxyl group, ethoxy, and an oxygen atom bonded to a silicon atom of another monomer; and R can be —$CH_2$—.

In another particular embodiment, each $Z^9$ can be a hydroxyl group, ethoxy or an oxygen atom bonded to a silicon atom of another comonomer; $Z^{10}$ and $Z^{11}$ each independently can be selected from the group consisting of a hydroxyl group, ethoxy, and an oxygen atom bonded to a silicon atom of another monomer; and R can be —HC=CH—.

In another particular embodiment, each $Z^9$ can be a hydroxyl group, methoxy or an oxygen atom bonded to a silicon atom of another comonomer; $Z^{10}$ and $Z^{11}$ each independently can be selected from the group consisting of a hydroxyl group, methoxy, and an oxygen atom bonded to a silicon atom of another monomer; and each R can be

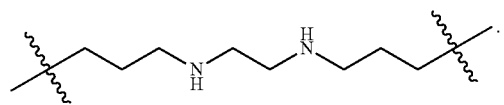 [SMILES: *CCCNCCNCCC*]

In another particular embodiment, each $Z^9$ can be a hydroxyl group, ethoxy or an oxygen atom bonded to a silicon atom of another comonomer; $Z^{10}$ can be a hydroxyl group, ethoxy, and an oxygen atom bonded to a silicon atom of another monomer; $Z^{11}$ can be methyl; and each R can be

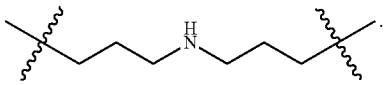 [SMILES: *CCCNCCC*]

In another particular embodiment, each $Z^9$ can be a hydroxyl group, methoxy or an oxygen atom bonded to a silicon atom of another comonomer; $Z^{10}$ can be a hydroxyl group, methoxy, and an oxygen atom bonded to a silicon atom of another monomer; $Z^{11}$ can be methyl; and each R can be

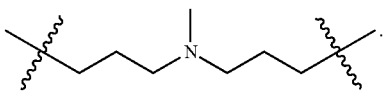 [SMILES: *CCCN(C)CCC*]

In another embodiment, the organosilica material support may comprise independent units of Formula (IV) as described herein and independent units of Formula (V) as described herein and not independent units of Formula (I) or Formula (II) as described herein. In particular, each $Z^5$ can be a hydrogen atom, ethyl or a bond to a silicon atom of another monomer; $Z^6$, $Z^7$ and $Z^8$ each independently can be selected from the group consisting of a hydroxyl group, ethoxy, and an oxygen atom bonded to a silicon atom of another monomer and each $Z^9$ can be a hydroxyl group, ethoxy or an oxygen atom bonded to a silicon atom of another comonomer; $Z^{10}$ and $Z^{11}$ each independently can be selected from the group consisting of a hydroxyl group, ethoxy, and an oxygen atom bonded to a silicon atom of another monomer; and R can be —$CH_2$—.

II.H. Monomers of Formula (VI)

In various embodiments, the organosilica material may further comprise another monomer in combination with independent units of Formula (I) and/or Formula (II) and optionally independent units Formula (III), (IV) and/or Formula (V), such as another monomer having at least one independent unit of Formula $M^1(OZ^{12})_3$ (VI), wherein $M^1$ represents a Group 13 metal and each $Z^{12}$ independently represents a hydrogen atom, a $C_1$-$C_6$ alkyl or a bond to a silicon atom of another monomer.

Additionally or alternatively, $M^1$ can be B, Al, Ga, IN Tl, or Uut. In particular, $M^1$ can be Al or B.

Additionally or alternatively, each $Z^{12}$ can be a hydrogen atom.

Additionally or alternatively, $M^1$ can be Al or B and $Z^3$ can be a hydrogen atom.

Additionally or alternatively, each $Z^{12}$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^3$ can be methyl, ethyl, propyl or butyl.

Additionally or alternatively, $M^1$ can be Al or B and $Z^{12}$ can be a hydrogen atom, methyl, ethyl, propyl or butyl.

Additionally or alternatively, each $Z^{12}$ can be a bond to a silicon atom of another monomer.

Additionally or alternatively, $M^1$ can be Al or B and each $Z^{12}$ can be a hydrogen atom, methyl, ethyl, propyl, butyl or a bond to a silicon atom of another monomer.

Additionally or alternatively, $M^1$ can be Al or B and each $Z^{12}$ can be a hydrogen atom or a bond to a silicon atom of another monomer.

Additionally or alternatively, $M^1$ can be Al and each $Z^{12}$ can be a hydrogen atom, methyl, ethyl, propyl, butyl or a bond to a silicon atom of another monomer.

In a particular embodiment, $M^1$ can be Al and each $Z^{12}$ can be a hydrogen atom, methyl or a bond to a silicon atom of another monomer.

In another particular embodiment, $M^1$ can be Al and each $Z^{12}$ can be a hydrogen atom, ethyl or a bond to a silicon atom of another monomer.

In another particular embodiment, $M^1$ can be Al and each $Z^{12}$ can be a hydrogen atom, propyl or a bond to a silicon atom of another monomer.

In another particular embodiment, $M^1$ can be Al and each $Z^{12}$ can be a hydrogen atom, butyl or a bond to a silicon atom of another monomer.

In another particular embodiment, $M^1$ can be Al or B; and each $Z^{12}$ can be a hydrogen atom or a bond to a silicon atom of another monomer.

II.I. Monomers of Formula (VI)

In various embodiments, the organosilica material may further comprise another monomer in combination with independent units of Formula (I) and/or Formula (II) and optionally independent units Formula (III), (IV), (V) and/or Formula (VI), such as another monomer having at least one independent unit of Formula$(Z^{13}O)_2M^2$-O—Si$(OZ^{14})_3$ (VII), wherein $M^2$ represents a Group 13 metal and $Z^{13}$ and $Z^{14}$ each independently represent a hydrogen atom, a $C_1$-$C_6$ alkyl group or a bond to a silicon atom of another monomer.

Additionally or alternatively, $M^2$ can be B, Al, Ga, IN Tl, or Uut. In particular, $M^2$ can be Al or B.

Additionally or alternatively, $Z^{13}$ and/or $Z^{14}$ each can be a hydrogen atom.

Additionally or alternatively, $M^2$ can be Al or B and $Z^{13}$ and/or $Z^{14}$ each can be a hydrogen atom.

Additionally or alternatively, $Z^{13}$ and/or $Z^{14}$ each can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^{13}$ and/or $Z^{14}$ can be methyl, ethyl, propyl or butyl.

Additionally or alternatively, $M^2$ can be Al or B; and $Z^{13}$ and/or $Z^{14}$ each independently can be a hydrogen atom, methyl, ethyl, propyl or butyl.

Additionally or alternatively, $Z^{13}$ and/or $Z^{14}$ each can be a bond to a silicon atom of another monomer.

Additionally or alternatively, $M^2$ can be Al or B; and $Z^{13}$ and $Z^{14}$ each independently can be a hydrogen atom, methyl, ethyl, propyl, butyl or a bond to a silicon atom of another monomer.

Additionally or alternatively, $M^2$ can be Al or B; and $Z^{13}$ and $Z^{14}$ each independently can be a hydrogen atom or a bond to a silicon atom of another monomer.

Additionally or alternatively, $M^2$ can be Al; and $Z^{13}$ and $Z^{14}$ each independently can be a hydrogen atom, methyl, ethyl, propyl, butyl or a bond to a silicon atom of another monomer.

In a particular embodiment, $M^2$ can be Al; and $Z^{13}$ and $Z^{14}$ each independently can be a hydrogen atom, methyl or a bond to a silicon atom of another monomer.

In another particular embodiment, $M^2$ can be Al; and $Z^{13}$ and $Z^{14}$ each independently can be a hydrogen atom, ethyl or a bond to a silicon atom of another monomer.

In another particular embodiment, $M^2$ can be Al; and $Z^{13}$ and $Z^{14}$ each independently can be a hydrogen atom, propyl or a bond to a silicon atom of another monomer.

In another particular embodiment, $M^2$ can be Al; and $Z^{13}$ and $Z^{14}$ each independently can be a hydrogen atom, butyl or a bond to a silicon atom of another monomer.

In another particular embodiment, $M^2$ can be Al or B; and $Z^{13}$ and $Z^{14}$ each independently can be a hydrogen atom or a bond to a silicon atom of another monomer.

The organosilica materials described herein can be characterized as described in the following sections.

II.J. X-Ray Diffraction Peaks

The organosilica materials described herein can exhibit powder X-ray diffraction patterns with one broad peak between about 1 and about 4 degrees 2θ, particularly one broad peak between about 1 and about 3 degrees 2θ. Additionally or alternatively, the organosilica materials can exhibit substantially no peaks in the range of about 0.5 to about 10 degrees 2θ, about 0.5 to about 12 degrees 2θ range, about 0.5 to about 15 degrees 2θ, about 0.5 to about 20 degrees 2θ, about 0.5 to about 30 degrees 2θ, about 0.5 to about 40 degrees 2θ, about 0.5 to about 50 degrees 2θ, about 0.5 to about 60 degrees 2θ, about 0.5 to about 70 degrees 2θ, about 2 to about 10 degrees 2θ, about 2 to about 12 degrees 2θ range, about 2 to about 15 degrees 2θ, about 2 to about 20 degrees 2θ, about 2 to about 30 degrees 2θ, about 2 to about 40 degrees 2θ, about 2 to about 50 degrees 2θ, about 2 to about 60 degrees 2θ, about 2 to about 70 degrees 2θ, about 3 to about 10 degrees 2θ, about 3 to about 12 degrees 2θ range, about 3 to about 15 degrees 2θ, about 3 to about 20 degrees 2θ, about 3 to about 30 degrees 2θ, about 3 to about 40 degrees 2θ, about 3 to about 50 degrees 2θ, about 3 to about 60 degrees 2θ, or about 3 to about 70 degrees 2θ.

II.K. Silanol Content

The organosilica material support described can have a silanol content that varies within wide limits, depending on the composition of the synthesis solution. The silanol content can conveniently be determined by solid state silicon NMR.

In various aspects, the organosilica materials can have a silanol content of greater than about 5%, greater than about 10%, greater than about 15%, greater than about 20%, greater than about 25%, greater than about 30%, greater than about 33%, greater than 35%, greater than about 40%, greater than about 41%, greater than about 44%, greater than about 45%, greater than about 50%, greater than about 55%, greater than about 60%, greater than about 65%, greater than about 70%, greater than about 75%, or about 80%. In certain embodiments, the silanol content can be greater than about 30% or greater than about 41%.

Additionally or alternatively, the organosilica materials may have a silanol content of about 5% to about 80%, about 5% to about 75%, about 5% to about 70%, about 5% to about 65%, about 5% to about 60%, about 5% to about 55%, about 5% to about 50%, about 5% to about 45%, about 5% to about 44%, about 5% to about 41%, about 5% to about 40%, about 5% to about 35%, about 5% to about 33%, about 5% to about 30%, about 5% to about 25%, about 5% to about 20%, about 5% to about 15%, about 5% to about 10%, about 10% to about 80%, about 10% to about 75%, about 10% to about 70%, about 10% to about 65%, about 10% to about 60%, about 10% to about 55%, about 10% to about 50%, about 10% to about 45%, about 10% to about 44%, about 10% to about 41%, about 10% to about 40%, about 10% to about 35%, about 10% to about 33%, about 10% to about 30%, about 10% to about 25%, about 10% to about 20%, about 20% to about 80%, about 20% to about 75%, about 20% to about 70%, about 20% to about 65%, about 20% to about 60%, about 20% to about 55%, about 20% to about 50%, about 20% to about 45%, about 20% to about 44%, about 20% to about 41%, about 20% to about 40%, about 20% to about 35%, about 20% to about 33%, about 20% to about 30%, about 20% to about 25%, about 30% to about 80%, about 30% to about 75%, about 30% to about 70%, about 30% to about 65%, about 30% to about 60%, about 30% to about 55%, about 30% to about 50%, about 30% to about 45%, about 30% to about 44%, about 30% to about 41%, about 30% to about 40%, about 30% to about 35%, about 30% to about 33%, about 40% to about 80%, about 40% to about 75%, about 40% to about 70%, about 40% to about 65%, about 40% to about 60%, about 40% to about 55%, about 40% to about 50%, about 40% to about 45%, about 40% to about 44%, or about 40% to about 41%.

II.L. Pore Size

The organosilica materials described herein are advantageously in a mesoporous form. As indicated previously, the term mesoporous refers to solid materials having pores with a diameter within the range of from about 2 nm to about 50 nm. The average pore diameter of the organosilica material can be determined, for example, using nitrogen adsorption-desorption isotherm techniques within the expertise of one of skill in the art, such as the BET (Brunauer Emmet Teller) method.

The organosilica materials can have an average pore diameter of about 0.2 nm, about 0.4 nm, about 0.5 nm, about 0.6 nm, about 0.8 nm, about 1.0 nm, about 1.5 nm, about 1.8 nm or less than about 2.0 nm.

Additionally or alternatively, the organosilica materials can advantageously have an average pore diameter within the mesopore range of about 2.0 nm, about 2.5 nm, about 3.0 nm, about 3.1 nm, about 3.2 nm, about 3.3 nm, about 3.4 nm, about 3.5 nm, about 3.6 nm, about 3.7 nm, about 3.8 nm, about 3.9 nm about 4.0 nm, about 4.1 nm, about 4.5 nm, about 5.0 nm, about 6.0 nm, about 7.0 nm, about 7.3 nm, about 8 nm, about 8.4 nm, about 9 nm, about 10 nm, about 11 nm, about 13 nm, about 15 nm, about 18 nm, about 20 nm, about 23 nm, about 25 nm, about 30 nm, about 40 nm, about 45 nm, or about 50 nm.

Additionally or alternatively, the organosilica materials can have an average pore diameter of 0.2 nm to about 50 nm, about 0.2 nm to about 40 nm, about 0.2 nm to about 30 nm, about 0.2 nm to about 25 nm, about 0.2 nm to about 23 nm, about 0.2 nm to about 20 nm, about 0.2 nm to about 18 nm, about 0.2 nm to about 15 nm, about 0.2 nm to about 13 nm, about 0.2 nm to about 11 nm, about 0.2 nm to about 10 nm, about 0.2 nm to about 9 nm, about 0.2 nm to about 8.4 nm, about 0.2 nm to about 8 nm, about 0.2 nm to about 7.3 nm, about 0.2 nm to about 7.0 nm, about 0.2 nm to about 6.0 nm, about 0.2 nm to about 5.0 nm, about 0.2 nm to about 4.5 nm, about 0.2 nm to about 4.1 nm, about 0.2 nm to about 4.0 nm, about 0.2 nm to about 3.9 nm, about 0.2 nm to about 3.8 nm, about 0.2 nm to about 3.7 nm, about 0.2 nm to about 3.6 nm, about 0.2 nm to about 3.5 nm, about 0.2 nm to about 3.4 nm, about 0.2 nm to about 3.3 nm, about 0.2 nm to about 3.2 nm, about 0.2 nm to about 3.1 nm, about 0.2 nm to about 3.0 nm, about 0.2 nm to about 2.5 nm, about 0.2 nm to about 2.0 nm, about 0.2 nm to about 1.0 nm, about 1.0 nm to about 50 nm, about 1.0 nm to about 40 nm, about 1.0 nm to about 30 nm, about 1.0 nm to about 25 nm, about 1.0 nm to about 23 nm, about 1.0 nm to about 20 nm, about 1.0 nm to about 18 nm, about 1.0 nm to about 15 nm, about 1.0 nm to about 13 nm, about 1.0 nm to about 11 nm, about 1.0 nm to about 10 nm, about 1.0 nm to about 9 nm, about 1.0 nm to about 8.4 nm, about 1.0 nm to about 8 nm, about 1.0 nm to about 7.3 nm, about 1.0 nm to about 7.0 nm, about 1.0 nm to about 6.0 nm, about 1.0 nm to about 5.0 nm, about 1.0 nm to about 4.5 nm, about 1.0 nm to about 4.1 nm, about 1.0 nm to about 4.0 nm, about 1.0 nm to about 3.9 nm, about 1.0 nm to about 3.8 nm, about 1.0 nm to about 3.7 nm, about 1.0 nm to about 3.6 nm, about 1.0 nm to about 3.5 nm, about 1.0 nm to about 3.4 nm, about 1.0 nm to about 3.3 nm, about 1.0 nm to about 3.2 nm, about 1.0 nm to about 3.1 nm, about 1.0 nm to about 3.0 nm or about 1.0 nm to about 2.5 nm.

In particular, the organosilica materials can advantageously have an average pore diameter in the mesopore range of about 2.0 nm to about 50 nm, about 2.0 nm to about 40 nm, about 2.0 nm to about 30 nm, about 2.0 nm to about 25 nm, about 2.0 nm to about 23 nm, about 2.0 nm to about 20 nm, about 2.0 nm to about 18 nm, about 2.0 nm to about 15 nm, about 2.0 nm to about 13 nm, about 2.0 nm to about 11 nm, about 2.0 nm to about 10 nm, about 2.0 nm to about 9 nm, about 2.0 nm to about 8.4 nm, about 2.0 nm to about 8 nm, about 2.0 nm to about 7.3 nm, about 2.0 nm to about 7.0 nm, about 2.0 nm to about 6.0 nm, about 2.0 nm to about 5.0 nm, about 2.0 nm to about 4.5 nm, about 2.0 nm to about 4.1 nm, about 2.0 nm to about 4.0 nm, about 2.0 nm to about 3.9 nm, about 2.0 nm to about 3.8 nm, about 2.0 nm to about 3.7 nm, about 2.0 nm to about 3.6 nm, about 2.0 nm to about 3.5 nm, about 2.0 nm to about 3.4 nm, about 2.0 nm to about 3.3 nm, about 2.0 nm to about 3.2 nm, about 2.0 nm to about 3.1 nm, about 2.0 nm to about 3.0 nm, about 2.0 nm to about 2.5 nm, about 2.5 nm to about 50 nm, about 2.5 nm to about 40 nm, about 2.5 nm to about 30 nm, about 2.5 nm to about 25 nm, about 2.5 nm to about 23 nm, about 2.5 nm to about 20 nm, about 2.5 nm to about 18 nm, about 2.5 nm to about 15 nm, about 2.5 nm to about 13 nm, about 2.5 nm to about 11 nm, about 2.5 nm to about 10 nm, about 2.5 nm to about 9 nm, about 2.5 nm to about 8.4 nm, about 2.5 nm to about 8 nm, about 2.5 nm to about 7.3 nm, about 2.5 nm to about 7.0 nm, about 2.5 nm to about 6.0 nm, about 2.5 nm to about 5.0 nm, about 2.5 nm to about 4.5 nm, about 2.5 nm to about 4.1 nm, about 2.5 nm to about 4.0 nm, about 2.5 nm to about 3.9 nm, about 2.5 nm to about 3.8 nm, about 2.5 nm to about 3.7 nm, about 2.5 nm to about 3.6 nm, about 2.5 nm to about 3.5 nm, about 2.5 nm to about 3.4 nm, about 2.5 nm to about 3.3 nm, about 2.5 nm to about 3.2 nm, about 2.5 nm to about 3.1 nm, about 2.5 nm to about 3.0 nm, about 3.0 nm to about 50 nm, about 3.0 nm to about 40 nm, about 3.0 nm to about 30 nm, about 3.0 nm to about 25 nm, about 3.0 nm to about 23 nm, about 3.0 nm to about 20 nm, about 3.0 nm to about 18 nm, about 3.0 nm to about 15 nm, about 3.0 nm to about 13 nm, about 3.0 nm to about 11 nm, about 3.0 nm to about 10 nm, about 3.0 nm to about 9 nm, about 3.0 nm to about 8.4 nm, about 3.0 nm to about 8 nm, about 3.0 nm to about 7.3 nm, about 3.0 nm to about 7.0 nm, about 3.0 nm to about 6.0 nm, about 3.0 nm to about 5.0 nm, about 3.0 nm to about 4.5 nm, about 3.0 nm to about 4.1 nm, or about 3.0 nm to about 4.0 nm.

In one particular embodiment, the organosilica materials described herein can have an average pore diameter of about 1.0 nm to about 30.0 nm, particularly about 1.0 nm to about 25.0 nm, particularly about 2.0 nm to about 25.0 nm, particularly about 2.0 nm to about 20.0 nm, particularly about 2.0 nm to about 15.0 nm, particularly about 2.0 nm to about 10.0 nm, or particularly about 3.0 nm to about 10.0 nm.

Using surfactant as a template to synthesize mesoporous materials can create highly ordered structure, e.g. well-defined cylindrical-like pore channels. In some circumstances, there may be no hysteresis loop observed from $N_2$ adsorption isotherm. In other circumstances, for instance where mesoporous materials can have less ordered pore structures, a hysteresis loop may be observed from $N_2$ adsorption isotherm experiments. In such circumstances, without being bound by theory, the hysteresis can result from the lack of regularity in the pore shapes/sizes and/or from bottleneck constrictions in such irregular pores.

II.M. Surface Area

The surface area of the organosilica materials can be determined, for example, using nitrogen adsorption-desorption isotherm techniques within the expertise of one of skill in the art, such as the BET (Brunauer Emmet Teller) method. This method may determine a total surface area, an external surface area, and a microporous surface area. As used herein, and unless otherwise specified, "total surface area" refers to the total surface area as determined by the BET method. As used herein, and unless otherwise specified, "microporous surface area" refers to microporous surface are as determined by the BET method.

In various embodiments, the organosilica materials can have a total surface area greater than or equal to about 100 $m^2/g$, greater than or equal to about 200 $m^2/g$, greater than or equal to about 300 $m^2/g$, greater than or equal to about 400 $m^2/g$, greater than or equal to about 450 $m^2/g$, greater than or equal to about 500 $m^2/g$, greater than or equal to about 550 $m^2/g$, greater than or equal to about 600 $m^2/g$, greater than or equal to about 700 $m^2/g$, greater than or equal to about 800 $m^2/g$, greater than or equal to about 850 $m^2/g$, greater than or equal to about 900 $m^2/g$, greater than or equal to about 1,000 $m^2/g$, greater than or equal to about 1,050 $m^2/g$, greater than or equal to about 1,100 $m^2/g$, greater than or equal to about 1,150 $m^2/g$, greater than or equal to about 1,200 $m^2/g$, greater than or equal to about 1,250 $m^2/g$, greater than or equal to about 1,300 $m^2/g$, greater than or equal to about 1,400 $m^2/g$, greater than or equal to about 1,450 $m^2/g$, greater than or equal to about 1,500 $m^2/g$, greater than or equal to about 1,550 $m^2/g$, greater than or equal to about 1,600 $m^2/g$, greater than or equal to about 1,700 $m^2/g$, greater than or equal to about 1,800 $m^2/g$, greater than or equal to about 1,900 $m^2/g$, greater than or equal to about 2,000 $m^2/g$, greater than or equal to greater than or equal to about 2,100 $m^2/g$, greater than or equal to about 2,200 $m^2/g$, greater than or equal to about 2,300 $m^2/g$ or about 2,500 $m^2/g$.

Additionally or alternatively, the organosilica materials may have a total surface area of about 50 $m^2/g$ to about 2,500 $m^2/g$, about 50 $m^2/g$ to about 2,000 $m^2/g$, about 50 $m^2/g$ to about 1,500 $m^2/g$, about 50 $m^2/g$ to about 1,000 $m^2/g$, about 100 $m^2/g$ to about 2,500 $m^2/g$, about 100 $m^2/g$ to about 2,300 $m^2/g$, about 100 $m^2/g$ to about 2,200 $m^2/g$, about 100 $m^2/g$ to about 2,100 $m^2/g$, about 100 $m^2/g$ to about 2,000 $m^2/g$, about 100 $m^2/g$ to about 1,900 $m^2/g$, about 100 $m^2/g$ to about 1,800 $m^2/g$, about 100 $m^2/g$ to about 1,700 $m^2/g$, about 100 $m^2/g$ to about 1,600 $m^2/g$, about 100 $m^2/g$ to about 1,550 $m^2/g$, about 100 $m^2/g$ to about 1,500 $m^2/g$, about 100 $m^2/g$ to about 1,450 $m^2/g$, about 100 $m^2/g$ to about 1,400 $m^2/g$, about 100 $m^2/g$ to about 1,300 $m^2/g$, about 100 $m^2/g$ to about 1,250 $m^2/g$, about 100 $m^2/g$ to about 1,200 $m^2/g$, about 100 $m^2/g$ to about 1,150 $m^2/g$, about 100 $m^2/g$ to about 1,100 $m^2/g$, about 100 $m^2/g$ to about 1,050 $m^2/g$, about 100 $m^2/g$ to about 1,000 $m^2/g$, about 100 $m^2/g$ to about 900 $m^2/g$, about 100 $m^2/g$ to about 850 $m^2/g$, about 100 $m^2/g$ to about 800 $m^2/g$, about 100 $m^2/g$ to about 700 $m^2/g$, about 100 $m^2/g$ to about 600 $m^2/g$, about 100 $m^2/g$ to about 550 $m^2/g$, about 100 $m^2/g$ to about 500 $m^2/g$, about 100 $m^2/g$ to about 450 $m^2/g$, about 100 $m^2/g$ to about 400 $m^2/g$, about 100 $m^2/g$ to about 300 $m^2/g$, about 100 $m^2/g$ to about 200 $m^2/g$, about 200 $m^2/g$ to about 2,500 $m^2/g$, about 200 $m^2/g$ to about 2,300 $m^2/g$, about 200 $m^2/g$ to about 2,200 $m^2/g$, about 200 $m^2/g$ to about 2,100 $m^2/g$, about 200 $m^2/g$ to about 2,000 $m^2/g$, about 200 $m^2/g$ to about 1,900 $m^2/g$, about 200 $m^2/g$ to about 1,800 $m^2/g$, about 200 $m^2/g$ to about 1,700 $m^2/g$, about 200 $m^2/g$ to about 1,600 $m^2/g$, about 200 $m^2/g$ to about 1,550 $m^2/g$, about 200 $m^2/g$ to about 1,500 $m^2/g$, about 200 $m^2/g$ to about 1,450 $m^2/g$, about 200 $m^2/g$ to about 1,400 $m^2/g$, about 200 $m^2/g$ to about 1,300 $m^2/g$, about 200 $m^2/g$ to about 1,250 $m^2/g$, about 200 $m^2/g$ to about 1,200 m²/g, about 200 m²/g to about 1,150 m²/g, about 200 m²/g to about 1,100 m²/g, about 200 m²/g to about 1,050 m²/g, about 200 m²/g to about 1,000 m²/g, about 200 m²/g to about 900 m²/g, about 200 m²/g to about 850 m²/g, about 200 m²/g to about 800 m²/g, about 200 m²/g to about 700 m²/g, about 200 m²/g to about 600 m²/g, about 200 m²/g to about 550 m²/g, about 200 m²/g to about 500 m²/g, about 200 m²/g to about 450 m²/g, about 200 m²/g to about 400 m²/g, about 200 m²/g to about 300 m²/g, about 500 m²/g to about 2,500 m²/g, about 500 m²/g to about 2,300 m²/g, about 500 m²/g to about 2,200 m²/g, about 500 m²/g to about 2,100 m²/g, about 500 m²/g to about 2,000 m²/g, about 500 m²/g to about 1,900 m²/g, about 500 m²/g to about 1,800 m²/g, about 500 m²/g to about 1,700 m²/g, about 500 m²/g to about 1,600 m²/g, about 500 m²/g to about 1,550 m²/g, about 500 m²/g to about 1,500 m²/g, about 500 m²/g to about 1,450 m²/g, about 500 m²/g to about 1,400 m²/g, about 500 m²/g to about, 300 m²/g, about 500 m²/g to about 1,250 m²/g, about 500 m²/g to about 1,200 m²/g, about 500 m²/g to about 1,150 m²/g, about 500 m²/g to about 1,100 m²/g, about 500 m²/g to about 1,050 m²/g, about 500 m²/g to about 1,000 m²/g, about 500 m²/g to about 900 m²/g, about 500 m²/g to about 850 m²/g, about 500 m²/g to about 800 m²/g, about 500 m²/g to about 700 m²/g, about 500 m²/g to about 600 m²/g, about 500 m²/g to about 550 m²/g, about 1,000 m²/g to about 2,500 m²/g, about 1,000 m²/g to about 2,300 m²/g, about 1,000 m²/g to about 2,200 m²/g, about 1,000 m²/g to about 2,100 m²/g, about 1,000 m²/g to about 2,000 m²/g, about 1,000 m²/g to about 1,900 m²/g, about 1,000 m²/g to about 1,800 m²/g, about 1,000 m²/g to about 1,700 m²/g, about 1,000 m²/g to about 1,600 m²/g, about 1,000 m²/g to about 1,550 m²/g, about 1,000 m²/g to about 1,500 m²/g, about 1,000 m²/g to about 1,450 m²/g, about 1,000 m²/g to about 1,400 m²/g, about 1,000 m²/g to about 1,300 m²/g, about 1,000 m²/g to about 1,250 m²/g, about 1,000 m²/g to about 1,200 m²/g, about 1,000 m²/g to about 1,150 m²/g, about 1,000 m²/g to about 1,100 m²/g, or about 1,000 m²/g to about 1,050 m²/g.

In one particular embodiment, the organosilica materials described herein may have a total surface area of about 200 m²/g to about 2,500 m² g, particularly about 400 m²/g to about 2,500 m² g, particularly about 400 m²/g to about 2,000 m²/g, particularly about 500 m²/g to about 2,000 m²/g, or particularly about 400 m²/g to about 1,500 m²/g.

II.N. Pore Volume

The pore volume of the organosilica materials made described herein can be determined, for example, using nitrogen adsorption-desorption isotherm techniques within the expertise of one of skill in the art, such as the BET (Brunauer Emmet Teller) method.

In various embodiments, the organosilica material can have a pore volume greater than or equal to about 0.1 cm³/g, greater than or equal to about 0.2 cm³/g, greater than or equal to about 0.3 cm³/g, greater than or equal to about 0.4 cm³/g, greater than or equal to about 0.5 cm³/g, greater than or equal to about 0.6 cm³/g, greater than or equal to about 0.7 cm³/g, greater than or equal to about 0.8 cm³/g, greater than or equal to about 0.9 cm³/g, greater than or equal to about 1.0 cm³/g, greater than or equal to about 1.1 cm³/g, greater than or equal to about 1.2 cm³/g, greater than or equal to about 1.3 cm³/g, greater than or equal to about 1.4 cm³/g, greater than or equal to about 1.5 cm³/g, greater than or equal to about 1.6 cm³/g, greater than or equal to about 1.7 cm³/g, greater than or equal to about 1.8 cm³/g, greater than or equal to about 1.9 cm³/g, greater than or equal to about 2.0 cm³/g, greater than or equal to about 2.5 cm³/g, greater than or equal to about 3.0 cm³/g, greater than or equal to about 3.5 cm³/g, greater than or equal to about 4.0 cm³/g, greater than or equal to about 5.0 cm³/g, greater than or equal to about 6.0 cm³/g, greater than or equal to about 7.0 cm³/g, or about 10.0 cm³/g.

Additionally or alternatively, the organosilica materials can have a pore volume of about 0.1 cm³/g to about 10.0 cm³/g, about 0.1 cm³/g to about 7.0 cm³/g, about 0.1 cm³/g to about 6.0 cm³/g, about 0.1 cm³/g to about 5.0 cm³/g, about 0.1 cm³/g to about 4.0 cm³/g, about 0.1 cm³/g to about 3.5 cm³/g, about 0.1 cm³/g to about 3.0 cm³/g, about 0.1 cm³/g to about 2.5 cm³/g, about 0.1 cm³/g to about 2.0 cm³/g, about 0.1 cm³/g to about 1.9 cm³/g, about 0.1 cm³/g to about 1.8 cm³/g, about 0.1 cm³/g to about 1.7 cm³/g, about 0.1 cm³/g to about 1.6 cm³/g, about 0.1 cm³/g to about 1.5 cm³/g, about 0.1 cm³/g to about 1.4 cm³/g, about 0.1 cm³/g to about 1.3 cm³/g, about 0.1 cm³/g to about 1.2 cm³/g, about 0.1 cm³/g to about 1.1, about 0.1 cm³/g to about 1.0 cm³/g, about 0.1 cm³/g to about 0.9 cm³/g, about 0.1 cm³/g to about 0.8 cm³/g, about 0.1 cm³/g to about 0.7 cm³/g, about 0.1 cm³/g to about 0.6 cm³/g, about 0.1 cm³/g to about 0.5 cm³/g, about 0.1 cm³/g to about 0.4 cm³/g, about 0.1 cm³/g to about 0.3 cm³/g, about 0.1 cm³/g to about 0.2 cm³/g, 0.2 cm³/g to about 10.0 cm³/g, about 0.2 cm³/g to about 7.0 cm³/g, about 0.2 cm³/g to about 6.0 cm³/g, about 0.2 cm³/g to about 5.0 cm³/g, about 0.2 cm³/g to about 4.0 cm³/g, about 0.2 cm³/g to about 3.5 cm³/g, about 0.2 cm³/g to about 3.0 cm³/g, about 0.2 cm³/g to about 2.5 cm³/g, about 0.2 cm³/g to about 2.0 cm³/g, about 0.2 cm³/g to about 1.9 cm³/g, about 0.2 cm³/g to about 1.8 cm³/g, about 0.2 cm³/g to about 1.7 cm³/g, about 0.2 cm³/g to about 1.6 cm³/g, about 0.2 cm³/g to about 1.5 cm³/g, about 0.2 cm³/g to about 1.4 cm³/g, about 0.2 cm³/g to about 1.3 cm³/g, about 0.2 cm³/g to about 1.2 cm³/g, about 0.2 cm³/g to about 1.1, about 0.5 cm³/g to about 1.0 cm³/g, about 0.5 cm³/g to about 0.9 cm³/g, about 0.5 cm³/g to about 0.8 cm³/g, about 0.5 cm³/g to about 0.7 cm³/g, about 0.5 cm³/g to about 0.6 cm³/g, about 0.5 cm³/g to about 0.5 cm³/g, about 0.5 cm³/g to about 0.4 cm³/g, about 0.5 cm³/g to about 0.3 cm³/g, 0.5 cm³/g to about 10.0 cm³/g, about 0.5 cm³/g to about 7.0 cm³/g, about 0.5 cm³/g to about 6.0 cm³/g, about 0.5 cm³/g to about 5.0 cm³/g, about 0.5 cm³/g to about 4.0 cm³/g, about 0.5 cm³/g to about 3.5 cm³/g, about 0.5 cm³/g to about 3.0 cm³/g, about 0.5 cm³/g to about 2.5 cm³/g, about 0.5 cm³/g to about 2.0 cm³/g, about 0.5 cm³/g to about 1.9 cm³/g, about 0.5 cm³/g to about 1.8 cm³/g, about 0.5 cm³/g to about 1.7 cm³/g, about 0.5 cm³/g to about 1.6 cm³/g, about 0.5 cm³/g to about 1.5 cm³/g, about 0.5 cm³/g to about 1.4 cm³/g, about 0.5 cm³/g to about 1.3 cm³/g, about 0.5 cm³/g to about 1.2 cm³/g, about 0.5 cm³/g to about 1.1, about 0.5 cm³/g to about 1.0 cm³/g, about 0.5 cm³/g to about 0.9 cm³/g, about 0.5 cm³/g to about 0.8 cm³/g, about 0.5 cm³/g to about 0.7 cm³/g, or about 0.5 cm³/g to about 0.6 cm³/g.

In a particular embodiment, the organosilica material supports can have a pore volume of about 0.1 cm³/g to about 5.0 cm³/g, particularly about 0.1 cm³/g to about 3.0 cm³/g, particularly about 0.2 cm³/g to about 3.0 cm³/g, particularly about 0.2 cm³/g to about 2.5 cm³/g, or particularly about 0.2 cm³/g to about 1.5 cm³/g.

II.O. Adsorption Capacity and Selectivity

The approach for analyzing liquid-phase adsorption data can be demonstrated by using direct experimental measurements of total moles and composition of liquid before and after contact with adsorbent, adsorbent loading and temperature. Gurwitsch's rule may be used as a first approximation for total saturation capacity of aromatic molecules on adsorbents (J. Phys. Chem Soc. Russ, 47, 805,1915). The separation factor may be calculated assuming a binary system adsorption (aromatic and non-aromatic compounds) based on component mole fractions in bulk phase and adsorbed phase.

In various aspects, the organosilica materials may have an adsorption capacity (gram of aromatic adsorbed/100 grams of adsorbent) of at least about 1 g/100 g adsorbent, at least about 2 g/100 g adsorbent, at least about 3 g/100 g adsorbent, at least about 4 g/100 g adsorbent, at least about 5 g/100 g adsorbent, at least about 6 g/100 g adsorbent, at least about 7 g/100 g adsorbent, at least about 8 g/100 g adsorbent, at least about 9 g/100 g adsorbent, at least about 10 g/100 g adsorbent, at least about 15 g/100 g adsorbent, or at least about 20 g/100 g. In particular, the organosilica materials may have an adsorption capacity of at least about 3 g/100 g adsorbent. Additionally or alternatively, the organosilica materials may have an adsorption capacity of about 1 to about 20 g/100 g adsorbent, about 1 to about 10 g/100 g adsorbent, about 1 to about 6 g/100 g adsorbent, about 2 to about 10 g/100 g adsorbent or about 2 to about 6 g/100 g adsorbent.

Additionally or alternatively, the organosilica materials may have a single ring aromatic separation factor (S12) and/or selectivity of at least about 2, at least about 4, at least about 6, at least about 8, at least about 10, at least about 12, at least about 14, at least about 15 or at least about 20. In particular, the organosilica materials may have a S12 of at least about 6. Additionally or alternatively, the organosilica materials may have a S12 and/or selectivity of about 2 to about 20, about 2 to about 15, 2 about to about 12 or about 4 to about 12.

II.P. Catalyst Metal

The organosilica material may further comprise at least one catalyst metal. The at least one catalyst metal may be incorporated within the pores of the organosilica material. Exemplary catalyst metals can include, but are not limited to, a Group 6 metal, a Group 8 metal, a Group 9 metal, a Group 10 metal or a combination thereof. Exemplary Group 6 metals can include, but are not limited to, chromium, molybdenum, and/or tungsten, particularly including molybdenum and/or tungsten. Exemplary Group 8 metals can include, but are not limited to, iron, ruthenium, and/or osmium. Exemplary Group 9 metals can include, but are not limited to, cobalt, rhodium, and/or iridium, particularly including cobalt. Exemplary Group 10 metals can include, but are not limited to, nickel, palladium and/or platinum.

In a particular embodiment, the catalyst metal may be selected from the group consisting of a Group 8 metal, a Group 9 metal, a Group 10 metal and a combination thereof. Additionally or alternatively, the at least one catalyst metal may be selected from the group consisting of platinum (Pt), palladium (Pd), iridium (Ir), rhodium (Rh) or a combination thereof, particularly, platinum (Pt), palladium (Pd), and a mixture thereof.

Additionally or alternatively, the catalyst metal may be present in an amount of at least about 0.010 wt. %, at least about 0.050 wt. %, at least about 0.10 wt. %, at least about 0.20 wt. %, at least about 0.40 wt. %, at least about 0.50 wt. %, at least about 0.60 wt. %, at least about 0.80 wt. %, at least about 1.0 wt. %, at least about 1.2 wt. %, at least about 1.4 wt. %, at least about 1.5 wt. %, at least about 1.6 wt. %, at least about 1.8 wt. %, at least about 2.0 wt. %, at least about 2.2 wt. %, at least about 2.4 wt. %, at least about 2.6 wt. %, at least about 2.8 wt. %, at least about 3.0 wt. %, at least about 3.5 wt. %, or at least about 4.0 wt. %. All metals weight percents are on support. By "on support" it is meant that the percents are based on the weight of the support, i.e., the organosilica material and optionally, binder material. For example, if the support were to weigh 100 grams, then 20 wt. % catalyst metal would mean that 20 grams of the catalyst metal was on the support.

Additionally or alternatively, the catalyst metal may be present in an amount of about 0.010 wt. % to about 4.0 wt. %, about 0.010 wt. % to about 3.5 wt. %, about 0.010 wt. % to about 3.0 wt. %, about 0.010 wt. % to about 2.8 wt. %, about 0.010 wt. % to about 2.6 wt. %, about 0.010 wt. % to about 2.4 wt. %, about 0.010 wt. % to about 2.2 wt. %, about 0.010 wt. % to about 2.0 wt. %, about 0.010 wt. % to about 1.8 wt. %, about 0.010 wt. % to about 1.6 wt. %, about 0.010 wt. % to about 1.5 wt. %, about 0.010 wt. % to about 1.4 wt. %, about 0.010 wt. % to at least about 1.2 wt. %, about 0.010 wt. % to about 1.0 wt. %, about 0.010 wt. % to about 0.80 wt. %, about 0.010 wt. % to about 0.60 wt. %, about 0.010 wt. % to about 0.50 wt. %, about 0.010 wt. % to about 0.40 wt. %, about 0.010 wt. % to about 0.20 wt. %, about 0.010 wt. % to about 0.10 wt. %, about 0.10 wt. % to about 4.0 wt. %, about 0.10 wt. % to about 3.5 wt. %, about 0.10 wt. % to about 3.0 wt. %, about 0.10 wt. % to about 2.8 wt. %, about 0.10 wt. % to about 2.6 wt. %, about 0.10 wt. % to about 2.4 wt. %, about 0.10 wt. % to about 2.2 wt. %, about 0.10 wt. % to about 2.0 wt. %, about 0.10 wt. % to about 1.8 wt. %, about 0.10 wt. % to about 1.6 wt. %, about 0.10 wt. % to about 1.5 wt. %, about 0.10 wt. % to about 1.4 wt. %, about 0.10 wt. % to at least about 1.2 wt. %, about 0.10 wt. % to about 1.0 wt. %, about 0.10 wt. % to about 0.80 wt. %, about 0.10 wt. % to about 0.60 wt. %, about 0.10 wt. % to about 0.50 wt. %, about 0.10 wt. % to about 0.40 wt. %, about 0.10 wt. % to about 0.20 wt. %, about 1.0 wt. % to about 4.0 wt. %, about 1.0 wt. % to about 3.5 wt. %, about 1.0 wt. % to about 3.0 wt. %, about 1.0 wt. % to about 2.8 wt. %, about 1.0 wt. % to about 2.6 wt. %, about 1.0 wt. % to about 2.4 wt. %, about 1.0 wt. % to about 2.2 wt. %, about 1.0 wt. % to about 2.0 wt. %, about 1.0 wt. % to about 1.8 wt. %, about 1.0 wt. % to about 1.6 wt. %, about 1.0 wt. % to about 1.5 wt. %, about 1.0 wt. % to about 1.4 wt. %, or about 1.0 wt. % to at least about 1.2 wt. %.

In particular, the catalyst metal may be present in an amount of about 0.010 wt. % to about 4.0 wt. %, about 0.05 wt. % to about 3.5 wt. %, about 0.1 wt. % to about 2.0 wt. %, or about 0.1 wt. % to about 1.4 wt. %.

The catalyst metal can be incorporated into the organosilica material by any convenient method, such as by impregnation, by ion exchange, by complexation to surface sites or physically admixed with the organosilica material. If the catalyst metal is to be impregnated into or exchanged onto the organosilica material and optionally, binder, it may be done, for example, by treating the organosilica material with a suitable ion containing the catalyst metal. If the catalyst metal is platinum, suitable platinum compounds include chloroplatinic acid, platinous chloride and various compounds containing the platinum amine complex. The catalyst metal may also be incorporated into, onto, or with the composited support and binder material by utilizing a compound(s) wherein the catalyst metal is present in the cation of the compound and/or compounds or in which it is present in the anion of the compound(s). It should be noted that both cationic and anionic compounds can be used. Non-limiting examples of suitable palladium or platinum compounds in which the metal is in the form of a cation or cationic complex are $Pd(NH_3)_4Cl_2$ or $Pt(NH_3)_4Cl_2$ are particularly useful, as are anionic complexes such as the vanadate and metatungstate ions. Cationic forms of other metals are also very useful since they may be exchanged onto the crystalline material or impregnated into it.

The catalyst metal so incorporated may be employed to promote any one of a number of catalytic tranformations commonly conducted in petroleum refining or petrochemicals production. Examples of such catalytic processes can include, but are not limited to, hydrogenation, dehydrogenation, aromatization, aromatic saturation, hydrodesulfurization, olefin oligomerization, polymerization, hydrodenitrogenation, hydrocracking, naphtha reforming, paraffin isomerization, aromatic transalkylation, saturation of double/triple bonds, and the like, as well as combinations thereof. In particular, the catalyst metal may be employed for aromatic hydrogenation and/or saturation.

Additionally or alternatively, the incorporation of a catalyst metal can also improve the adsorption capacity and selectivity of adsorbents for aromatics, sulfur-containing species, and nitrogen-containing species.

II.Q. Binder

In various aspects, the organosilica material may further comprise a binder or be self-bound. Suitable binders, include but are not limited to active and inactive materials, synthetic or naturally occurring zeolites, as well as inorganic materials such as clays and/or oxides such as silica, alumina, zirconia, titania, silica-alumina, cerium oxide, magnesium oxide, or combinations thereof. In particular, the binder may be selected from the group consisting of active and inactive materials, inorganic materials, clays, alumina, silica, silica-alumina, titania, zirconia, or a combination thereof. Particularly, the binder may comprise silica-alumina, alumina and/or zirconia, particularly alumina. Silica-alumina may be either naturally occurring or in the form of gelatinous precipitates or gels including mixtures of silica and metal oxides. It should be noted it is recognized herein that the use of a material in conjunction with a zeolite binder material, i.e., combined therewith or present during its synthesis, which itself is catalytically active may change the conversion and/or selectivity of the finished product. It is also recognized herein that inactive materials can suitably serve as diluents to control the amount of conversion if the present disclosure is employed in alkylation processes so that alkylation products can be obtained economically and orderly without employing other means for controlling the rate of reaction. These inactive materials may be incorporated into naturally occurring clays, e.g., bentonite and kaolin, to improve the crush strength of the catalyst under commercial operating conditions and function as binders or matrices for the catalyst. The adsorbents described herein typically can comprise, in a composited form, a ratio of support material to binder material of about 100 parts support material to about zero parts binder material; about 99 parts support material to about 1 parts binder material; about 95 parts support material to about 5 parts binder material. Additionally or alternatively, the adsorbents described herein typically can comprise, in a composited form, a ratio of support material to binder material ranging from about 90 parts support material to about 10 parts binder material to about 10 parts support material to about 90 parts binder material; about 85 parts support material to about 15 parts binder material to about 15 parts support material to about 85 parts binder material; about 80 parts support material to 20 parts binder material to 20 parts support material to 80 parts binder material, all ratios being by weight, typically from 80:20 to 50:50 support material:binder material, preferably from 65:35 to 35:65. Compositing may be done by conventional means including mulling the materials together followed by extrusion of pelletizing into the desired finished catalyst particles.

II.R. Further Metals

In some embodiments, the organosilica material can further comprise cationic metal sites incorporated into the network structure. Such cationic metal sites may be incorporated by any convenient method, such as impregnation or complexation to the surface, through an organic precursor, or by some other method. This organometallic material may be employed in a number of hydrocarbon separations conducted in petroleum refining or petrochemicals production. Examples of such compounds to be desirably separated from petrochemicals/fuels can include olefins, paraffins, aromatics, and the like.

Additionally or alternatively, the organosilica material can further comprise a surface metal incorporated within the pores of the organosilica material. The surface metal can be selected from a Group 1 element, a Group 2 element, a Group 11 element, a Group 12 element, a Group 13 element, and a combination thereof. When a Group 1 element is present, it can preferably comprise or be sodium and/or potassium. When a Group 2 element is present, it can include, but may not be limited to, magnesium and/or calcium. When a Group 11 element is present, it can include, but may not be limited to, copper, silver and/or gold. When a Group 12 element is present, it can include, but may not be limited to, zinc and/or cadmium. When a Group 13 element is present, it can include, but may not be limited to, boron and/or aluminum.

One or more of the Group 1, 2, 6, 8-13 elements may be present on an exterior and/or interior surface of the organosilica material. For example, one or more of the Group 1, 2 and/or 11-13 elements may be present in a first layer on the organosilica material and one or more of the Group 6, 8, 9 and/or 10 elements may be present in a second layer, e.g., at least partially atop the Group 1, 2 and/or 13 elements. Additionally or alternatively, only one or more Group 6, 8, 9 and/or 10 elements may present on an exterior and/or interior surface of the organosilica material. The surface metal(s) can be incorporated into/onto the organosilica material by any convenient method, such as by impregnation, deposition, grafting, co-condensation, by ion exchange, and/or the like. In particular, a Group 13 metal, such as, but not limited to, aluminum may be grafted onto a surface of the organo silica material support. Additionally or alternatively, a Group 4 metal, such as, but not limited to, titanium, zirconium and hafnium, may be grafted onto a surface of the organosilica material support.

II.S. Separating Conditions

In general, the organosilica material may be loaded into a vessel and/or bed. The organosilica material may be treated to make active, e.g., water may be removed and metal, if present, may be reduced. The organosilica material may be inerted to minimize exposure to water and other species that may adsorb onto the organosilica material. Typically a feedstream may be contacted with the organosilica material in the vessel for a specified time just prior to contaminant phases breaking through the bed and ending up in a product stream. At this point, the organosilica material may be regenerated. During regeneration, the feedstream may be halted and the adsorbed species may be removed through temperature, pressure, or a cleaning fluid until the majority of the adsorbed species is removed. Typically, regeneration flow may be counter-current (in an opposite direction) to a flow of the feedstream through the bed and/or vessel. Once regenerated the bed and/or vessel may be contacted with the feedstream. In some embodiments, multiple beds and/or vessels (e.g., at least 2-12 or more) may be used in the process with each of them at different stages of adsorbing and regenerating to ensure that aromatics are continually being separated from the feedstream.

Advantageously, separation of aromatic compound from a hydrocarbon feedstream (e.g. lube base stock) in the methods described herein can occur at room temperature and atmospheric pressure. Effective separation conditions can include temperatures of about 15° C. to about 30° C. and pressures of from about 5 psig to about 25 psig. In particular, separation can be performed at a temperature below about 100° C., below about 80° C., below about 60° C. or below about 50° C. Additionally or alternatively, separation can be performed at higher temperatures of about 20° C. to about 200° C., about 20° C. to about 150° C. or about 20° C. to about 100° C. and/or at higher pressures of about 5 psig to about 200 psig, about 5 psig to about 150 psig, 5 psig to about 100 psig, about 10 psig to about 100 psig, or about 10 psig to about 50 pisg. Particularly, separation can be performed at a temperature of about 20° C. to about 200° C. and a pressure of about 5 psig to about 100 psig.

II.S. Another Porous Material

The methods described herein can further comprise contacting a hydrocarbon feedstream (e.g. lube base stock) containing an aromatic compound with another porous material in combination with the organosilica material.

The another porous material may be any suitable microporous material, mesoporous material, analogous periodic mesoporous material (e.g. MCM-41, MCM-48, SBA-15, SBA-16, and KIT-6) metal oxide, carbon and combinations thereof. Examples of microporous materials include, but are not limited to, zeolites, titanosilicates, aluminophosphates (i.e., AlPO), MeAlPO (Me=Si, Ti, or Zr), silicoaluminophosphates (i.e., SAPO), metal-organic frameworks (MOFs) (e.g., zeolitic imidazolate frameworks (ZIFs)). Examples of ALPO Family members include, but are not limited to: ALPO-5, ALPO-11, ALPO-16, ALPO-18, ALPO-22, ALPO-34, ALPO-35, ALPO-47, ALPO-52, ALPO-61, ALPO-AFI, ALPO-kanemite, ALPO4-ZON, ALPO4-L, ALPO4-5, ALPO4-34, and meso-ALPO. Examples of SAPO family members include, but are not limited to: SAPO-5, SAPO-8, SAPO-11, SAPO-18, SAPO-23, SAPO-31, SAPO-34, SAPO-35, SAPO-37, SAPO-40, SAPO-44, SAPO-47, SAPO-SOD, SAPO4-L, meso-SAPO. Examples of MOF Family members include, but are not limited to: MOF-5, MOF-7, MIL-100, MIL101, ZIF-8, ZIF-11 etc. Examples of mesoporous materials include, but are not limited to M41S family materials (e.g., MCM-41, MCM-48, SBA-15, KIT-6). Examples of metal oxides include, but are not limited to silica (e.g., $SiO_2$), alumina (e.g., $Al_2O_3$), titanias (e.g., $TiO_2$, $Ti_2O_3$, TiO), magnesia (e.g., MgO), boria (e.g., $B_2O$, $B_2O3$, $B_6O$), clay, and combinations thereof. Examples of carbons include activated carbon, carbon molecular sieves, carbon nanotubes and combinations thereof.

In particular, the another porous material is a zeolite. The zeolite may have a framework type selected from the following group of framework types: ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAG, CAN, CAS, CDO, CFI, CGF, CGS, CHA, CHI, CLO, CON, CRB, CZP, DAC, DDR, DFO, DFT, DIA, DOH, DON, EAB, EDI, EMT, EON, EPI, ERI, ESV, ETR, EUO, EZT, FAR, FAU, FER, FRA, FRL, GIS, GIU, GME, GON, GOO, HEU, IFR, THW, ISV, ITE, ITH, ITW, TWR, IWV, IWW, JBW, KFI, LAU, LCS, LEV, LIO, LIT, LOS, LOV, LTA, LTL, LTN, MAR, MAZ, MEI, MEL, MEP, MER, MFI, MFS, MON, MOR, MOZ, MSE, MSO, MTF, MTN, MTT, MTW, MWW, NAB, NAT, NES, NON, NPO, NSI, OBW, OFF, OSI, OSO, OWE, PAR, PAU, PHI, PON, POZ, RHO, RON, RRO, RSN, RTE, RTH, RUT, RWR, RWY, SAO, SAS, SAT, SAV, SBE, SBS, SBT, SFE, SFF, SFG, SFH, SFN, SFO, SGT, SIV, SOD, SOS, SSY, STF, STI, STT, SZR, TER, THO, TON, TSC, TUN, UEI, UFI, UOZ, USI, UTL, VET, VFI, VNI, VSV, WEI, WEN, YUG, ZNI, and ZON. Particular examples of these framework types can include BEA, CHA, CFI, CLO, DDR, DON, EMT, ERI, FER, FAU, LTL, LTA, MWW, MOZ, MFI, MFS, MEL, MEI, MTW, MOR, MTT, MAZ, MFS, MTN, NES and combinations and intergrowths thereof.

AEL, AFO, AHT, ATO, CAN, EUO, FER, HEU, IMF, ITH, LAU, MEL, MFI, MFS, MRE, MSE, MTT, MTW, MWW, NES, OBW, OSI, PON, RRO, SFF, SFG, STF, STI, SZR, TON, TUN and VET. A person of ordinary skill in the art knows how to make the aforementioned frameworks. For example, see the references provided in the International Zeolite Association's database of zeolite structures found at www.iza-structure.org/databases.

Generally, the zeolite employed in the present method as another porous material can typically have a silica to alumina molar ratio of at least 2, e.g., from about 2 to about 500, or about 20 to about 200. In some cases, $SiO_2:Al_2O_3$ ratios can be from 2 to greater than 500, and essentially to pure $SiO_2$. Suitable zeolites can include, but are not necessarily limited to, ZSM-5, ZSM-11, ZSM-12, ZSM-23, ZSM-48, ZSM-57, ZSM-58 (DDR, Sigma 1, SSZ-28), MCM-22, MCM-49, NU-87, UTD-1, CIT-5, EMC-2, zeolite A (3A, 4A, 5A and intermediate sizes), zeolite Y, dealuminized Y, zeolite L (Linde Type L), mordenite, erionite, chabazite (including natural forms), zeolite beta, ITQ-29 ([Si]LTA), and the like, as well as intergrowths and combinations thereof. In certain embodiments, the zeolite can comprise, consist essentially of, or be 13X.

Additionally or alternatively, the zeolite may be present at least partly in hydrogen form in the adsorbent material (e.g., HZSM-5). Depending on the conditions used to synthesize the zeolite, this may implicate converting the zeolite from, for example, the alkali (e.g., sodium) form. This can readily be achieved, e.g., by ion exchange to convert the zeolite to the ammonium form, followed by calcination in air or an inert atmosphere at a temperature from about 400° C. to about 700° C. to convert the ammonium form to the active hydrogen form. If an organic structure directing agent is used in the synthesis of the zeolite, additional calcination may be desirable to remove the organic structure directing agent.

In various aspects, the organosilica material described herein and optionally, the another porous material described herein may be packed into one or more columns and/or one or more adsorbent beds. FIG. 1 provides an example of flow scheme for aromatic separation using Adsorbers A and B, e.g., in a liquid phase swing adsorption process including absorbent regeneration. Additionally or alternatively, the organosilica material and optional porous material may be present in a fixed bed, a moving bed or a fluidized bed.

Additionally or alternatively, the method can further comprise regenerating the organosilica material and optional porous material once it becomes saturated with the aromatic compounds, so that the organosilica material and optional porous material adsorbent material can be re-used. Regeneration can comprise reheating the organosilica material and optional porous material at temperature of about 50° C. to about 400° C. for a suitable duration of time. Additionally or alternatively, regeneration can comprise use of solvents (e.g., toluene, reformate, diesel), feedstreams, and product streams.

For example, a separated or adsorbed species (e.g., aromatic compounds) can be reversibly removed from the organosilica material and optional porous material either by thermal treatments ranging in temperature from 50° C. to 400° C. using inert purges, air purges, or oxidative gases. Additionally or alternatively, the separated or adsorbed species (e.g., aromatic compounds) can be reversibly removed by lowering the pressure to less than atmospheric pressure, i.e. vacuum. Additionally or alternatively, the separated or adsorbed species (e.g., aromatic compounds) can be removed by cleaning/washing the organosilica material and optional porous material with organic solvents (e.g., aromatic, alcohol, glycol, diols, etheres, glycol ether, surfactant containing solvents, amines, alcohol amines), super critical fluids, the feedstream, the product, or combinations of the cleaning liquid. Combinations of the aforementioned regeneration processes may be used as well.

Additionally or alternatively, the separating methods described herein may be used in combination with hydrogenation, dehydrogenation, cracking, isomerization processes of the hydrocarbon feedstream.

In various aspects, an at least partially purified lube base stock made by the methods of separating an aromatic compound described herein is provided herein.

II. Methods of Making the Organosilica Materials

In another embodiment, methods of making the organosilica materials described herein for separation of aromatic compounds are provided. The method comprises:

(a) providing an aqueous mixture that contains essentially no structure directing agent and/or porogen;

(b) adding at least one compound into the aqueous mixture to form a solution, wherein the at least one compound is selected from the group consisting of:

(i) a compound of Formula $[Z^{15}Z^{16}SiCH_2]_3$ (VIII), wherein each $Z^{15}$ can be a $C_1$-$C_4$ alkoxy group and $Z^{15}$ can be a $C_1$-$C_4$ alkoxy group or a $C_1$-$C_4$ alkyl group; and (ii) a cyclic compound of Formula

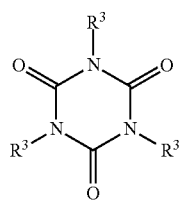

(IX)

wherein each $R^3$ independently can be a $X^5OX^6X^7SiX^8$ group, wherein each $X^5$ can be a $C_1$-$C_4$ alkyl group; $X^6$ and $X^7$ each independently can be a $C_1$-$C_4$ alkyl group or a $C_1$-$C_4$ alkoxy group; and each $X^8$ can be a $C_1$-$C_8$ alkylene group bonded to a nitrogen atom of the cyclic compound;

(c) aging the solution to produce a pre-product; and (d) drying the pre-product to obtain an organosilica material which is a polymer comprising independent units of a monomer of Formula (I) and/or a monomer of Formula (II), as described herein.

III.A. Aqueous Mixture

The organosilica materials described herein may be made using essentially no structure directing agent or porogen. Thus, the aqueous mixture contains essentially no added structure directing agent and/or no added porogen.

As used herein, "no added structure directing agent," and "no added porogen" means either (i) there is no component present in the synthesis of the organosilica material that aids in and/or guides the polymerization and/or polycondensing and/or organization of the building blocks that form the framework of the organosilica material; or (ii) such component is present in the synthesis of the organosilica material in a minor, or a non-substantial, or a negligible amount such that the component cannot be said to aid in and/or guide the polymerization and/or polycondensing and/or organization of the building blocks that form the framework of the organosilica material. Further, "no added structure directing agent" is synonymous with "no added template" and "no added templating agent."

1. Structure Directing Agent

Examples of a structure directing agent can include, but are not limited to, non-ionic surfactants, ionic surfactants, cationic surfactants, silicon surfactants, amphoteric surfactants, polyalkylene oxide surfactants, fluorosurfactants, colloidal crystals, polymers, hyper branched molecules, star-shaped molecules, macromolecules, dendrimers, and combinations thereof. Additionally or alternatively, the surface directing agent can comprise or be a poloxamer, a triblock polymer, a tetraalkylammonium salt, a nonionic polyoxyethylene alkyl, a Gemini surfactant, or a mixture thereof. Examples of a tetraalkylammonium salt can include, but are not limited to, cetyltrimethylammonium halides, such as cetyltrimethylammonium chloride (CTAC), cetyltrimethylammonium bromide (CTAB), and octadecyltrimethylammonium chloride. Other exemplary surface directing agents can additionally or alternatively include hexadecyltrimethylammonium chloride and/or cetylpyridinium bromide.

Poloxamers are block copolymers of ethylene oxide and propylene oxide, more particularly nonionic triblock copolymers composed of a central hydrophobic chain of polyoxypropylene (poly(propylene oxide)) flanked by two hydrophilic chains of polyoxyethylene (poly(ethylene oxide)). Specifically, the term "poloxamer" refers to a polymer having the formula $HO(C_2H_4)a(C_3H_6O)_b(C_2H_4O)_aH$ in which "a" and "b" denote the number of polyoxyethylene and polyoxypropylene units, respectively. Poloxamers are also known by the trade name Pluronic®, for example Pluronic® 123 and Pluronic® F127. An additional triblock polymer is B50-6600.

Nonionic polyoxyethylene alkyl ethers are known by the trade name Brij®, for example Brij® 56, Brij® 58, Brij® 76, Brij® 78. Gemini surfactants are compounds having at least two hydrophobic groups and at least one or optionally two hydrophilic groups per molecule have been introduced.

2. Porogen

A porogen material is capable of forming domains, discrete regions, voids and/or pores in the organosilica material. An example of a porogen is a block copolymer (e.g., a di-block polymer). As used herein, porogen does not include water. Examples of polymer porogens can include, but are not limited to, polyvinyl aromatics, such as polystyrenes, polyvinylpyridines, hydrogenated polyvinyl aromatics, polyacrylonitriles, polyalkylene oxides, such as polyethylene oxides and polypropylene oxides, polyethylenes, polylactic acids, polysiloxanes, polycaprolactones, polycaprolactams, polyurethanes, polymethacrylates, such as polymethylmethacrylate or polymethacrylic acid, polyacrylates, such as polymethylacrylate and polyacrylic acid, polydienes such as polybutadienes and polyisoprenes, polyvinyl chlorides, polyacetals, and amine-capped alkylene oxides, as well as combinations thereof.

Additionally or alternatively, porogens can be thermoplastic homopolymers and random (as opposed to block) copolymers. As used herein, "homopolymer" means compounds comprising repeating units from a single monomer. Suitable thermoplastic materials can include, but are not limited to, homopolymers or copolymers of polystyrenes, polyacrylates, polymethacrylates, polybutadienes, polyisoprenes, polyphenylene oxides, polypropylene oxides, polyethylene oxides, poly(dimethylsiloxanes), polytetrahydrofurans, polyethylenes, polycyclohexylethylenes, polyethyloxazolines, polyvinylpyridines, polycaprolactones, polylactic acids, copolymers of these materials and mixtures of these materials. Examples of polystyrene include, but are not limited to anionic polymerized polystyrene, syndiotactic polystyrene, unsubstituted and substituted polystyrenes (for example, poly(α-methyl styrene)). The thermoplastic materials may be linear, branched, hyperbranched, dendritic, or star like in nature.

Additionally or alternatively, the porogen can be a solvent. Examples of solvents can include, but are not limited to, ketones (e.g., cyclohexanone, cyclopentanone, 2-heptanone, cycloheptanone, cyclooctanone, cyclohexylpyrrolidinone, methyl isobutyl ketone, methyl ethyl ketone, acetone), carbonate compounds (e.g., ethylene carbonate, propylene carbonate), heterocyclic compounds (e.g., 3-methyl-2-oxazolidinone, dimethylimidazolidinone, N-methylpyrrolidone, pyridine), cyclic ethers (e.g., dioxane, tetrahydrofuran), chain ethers (e.g., diethyl ether, ethylene glycol dimethyl ether, propylene glycol dimethyl ether, tetraethylene glycol dimethyl ether, polyethylene glycol dimethyl ether, ethylene glycol monomethyl ether, ethylene glycol monoethyl ether, propylene glycol monomethyl ether (PGME), triethylene glycol monobutyl ether, propylene glycol monopropyl ether, triethylene glycol monomethyl ether, diethylene glycol ethyl ether, diethylene glycol methyl ether, dipropylene glycol methyl ether, dipropylene glycol dimethyl ether, propylene glycol phenyl ether, tripropylene glycol methyl ether), alcohols (e.g., methanol, ethanol), polyhydric alcohols (e.g., ethylene glycol, propylene glycol, polyethylene glycol, polypropylene glycol, glycerin, dipropylene glycol), nitrile compounds (e.g., acetonitrile, glutarodinitrile, methoxyacetonitrile, propionitrile, benzonitrile), esters (e.g., ethyl acetate, butyl acetate, methyl lactate, ethyl lactate, methyl methoxypropionate, ethyl ethoxypropionate, methyl pyruvate, ethyl pyruvate, propyl pyruvate, 2-methoxyethyl acetate, ethylene glycol monoethyl ether acetate, propylene glycol monomethyl ether acetate (PGMEA), butyrolactone, phosphoric acid ester, phosphonic acid ester), aprotic polar substances (e.g., dimethyl sulfoxide, sulfolane, dimethylformamide, dimethylacetamide), nonpolar solvents (e.g., toluene, xylene, mesitylene), chlorine-based solvents (e.g., methylene dichloride, ethylene dichloride), benzene, dichlorobenzene, naphthalene, diphenyl ether, diisopropylbenzene, triethylamine, methyl benzoate, ethyl benzoate, butyl benzoate, monomethyl ether acetate hydroxy ethers such as dibenzylethers, diglyme, triglyme, and mixtures thereof.

3. Base/Acid

In various embodiments, the aqueous mixture used in methods provided herein can comprise a base and/or an acid.

In certain embodiments where the aqueous mixture comprises a base, the aqueous mixture can have a pH from about 8 to about 15, from about 8 to about 14.5, from about 8 to about 14, from about 8 to about 13.5, from about 8 to about 13, from about 8 to about 12.5, from about 8 to about 12, from about 8 to about 11.5, from about 8 to about 11, from about 8 to about 10.5, from about 8 to about 10, from about 8 to about 9.5, from about 8 to about 9, from about 8 to about 8.5, from about 8.5 to about 15, from about 8.5 to about 14.5, from about 8.5 to about 14, from about 8.5 to about 13.5, from about 8.5 to about 13, from about 8.5 to about 12.5, from about 8.5 to about 12, from about 8.5 to about 11.5, from about 8.5 to about 11, from about 8.5 to about 10.5, from about 8.5 to about 10, from about 8.5 to about 9.5, from about 8.5 to about 9, from about 9 to about 15, from about 9 to about 14.5, from about 9 to about 14, from about 9 to about 13.5, from about 9 to about 13, from about 9 to about 12.5, from about 9 to about 12, from about 9 to about 11.5, from about 9 to about 11, from about 9 to about 10.5, from about 9 to about 10, from about 9 to about 9.5, from about 9.5 to about 15, from about 9.5 to about 14.5, from about 9.5 to about 14, from about 9.5 to about 13.5, from about 9.5 to about 13, from about 9.5 to about 12.5, from about 9.5 to about 12, from about 9.5 to about 11.5, from about 9.5 to about 11, from about 9.5 to about 10.5, from about 9.5 to about 10, from about 10 to about 15, from about 10 to about 14.5, from about 10 to about 14, from about 10 to about 13.5, from about 10 to about 13, from about 10 to about 12.5, from about 10 to about 12, from about 10 to about 11.5, from about 10 to about 11, from about 10 to about 10.5, from about 10.5 to about 15, from about 10.5 to about 14.5, from about 10.5 to about 14, from about 10.5 to about 13.5, from about 10.5 to about 13, from about 10.5 to about 12.5, from about 10.5 to about 12, from about 10.5 to about 11.5, from about 10.5 to about 11, from about 11 to about 15, from about 11 to about 14.5, from about 11 to about 14, from about 11 to about 13.5, from about 11 to about 13, from about 11 to about 12.5, from about 11 to about 12, from about 11 to about 11.5, from about 11.5 to about 15, from about 11.5 to about 14.5, from about 11.5 to about 14, from about 11.5 to about 13.5, from about 11.5 to about 13, from about 11.5 to about 12.5, from about 11.5 to about 12, from about 12 to about 15, from about 12 to about 14.5, from about 12 to about 14, from about 12 to about 13.5, from about 12 to about 13, from about 12 to about 12.5, from about 12.5 to about 15, from about 12.5 to about 14.5, from about 12.5 to about 14, from about 12.5 to about 13.5, from about 12.5 to about 13, from about 12.5 to about 15, from about 12.5 to about 14.5, from about 12.5 to about 14, from about 12.5 to about 13.5, from about 12.5 to about 13, from about 13 to about 15, from about 13 to about 14.5, from about 13 to about 14, from about 13 to about 13.5, from about 13.5 to about 15, from about 13.5 to about 14.5, from about 13.5 to about 14, from about 14 to about 15, from about 14 to about 14.5, and from about 14.5 to about 15.

In a particular embodiment comprising a base, the pH can be from about 9 to about 15, from about 8 to about 15, from about 9 to about 14 or about 8 to about 14.

Exemplary bases can include, but are not limited to, sodium hydroxide, potassium hydroxide, lithium hydroxide, pyridine, pyrrole, piperazine, pyrrolidine, piperidine, picoline, monoethanolamine, diethanolamine, dimethylmonoethanolamine, monomethyldiethanolamine, triethanolamine, diazabicyclooctane, diazabicyclononane, diazabicycloundecene, tetramethylammonium hydroxide, tetraethylammonium hydroxide, tetrapropylammonium hydroxide, tetrabutylammonium hydroxide, ammonia, ammonium hydroxide, methylamine, ethylamine, propylamine, butylamine, pentylamine, hexylamine, octylamine, nonylamine, decylamine, N,N-dimethylamine, N,N-diethylamine, N,N-dipropylamine, N,N-dibutylamine, trimethylamine, triethylamine, tripropylamine, tributylamine, cyclohexylamine, trimethylimidine, 1-amino-3-methylbutane, 3-amino-3-methylamine, dimethylglycine, and the like. These bases may be used either singly or in combination. In a particular embodiment, the base can comprise or be sodium hydroxide and/or ammonium hydroxide.

In certain embodiments where the aqueous mixture comprises an acid, the aqueous mixture can have a pH from about 0.01 to about 6.0, from about 0.01 to about 5, from about 0.01 to about 4, from about 0.01 to about 3, from about 0.01 to about 2, from about 0.01 to about 1, 0.1 to about 6.0, about 0.1 to about 5.5, about 0.1 to about 5.0, from about 0.1 to about 4.8, from about 0.1 to about 4.5, from about 0.1 to about 4.2, from about 0.1 to about 4.0, from about 0.1 to about 3.8, from about 0.1 to about 3.5, from about 0.1 to about 3.2, from about 0.1 to about 3.0, from about 0.1 to about 2.8, from about 0.1 to about 2.5, from about 0.1 to about 2.2, from about 0.1 to about 2.0, from about 0.1 to about 1.8, from about 0.1 to about 1.5, from about 0.1 to about 1.2, from about 0.1 to about 1.0, from about 0.1 to about 0.8, from about 0.1 to about 0.5, from about 0.1 to about 0.2, about 0.2 to about 6.0, about 0.2 to about 5.5, from about 0.2 to about 5, from about 0.2 to about 4.8, from about 0.2 to about 4.5, from about 0.2 to about 4.2, from about 0.2 to about 4.0, from about 0.2 to about 3.8, from about 0.2 to about 3.5, from about 0.2 to about 3.2, from about 0.2 to about 3.0, from about 0.2 to about 2.8, from about 0.2 to about 2.5, from about 0.2 to about 2.2, from about 0.2 to about 2.0, from about 0.2 to about 1.8, from about 0.2 to about 1.5, from about 0.2 to about 1.2, from about 0.2 to about 1.0, from about 0.2 to about 0.8, from about 0.2 to about 0.5, about 0.5 to about 6.0, about 0.5 to about 5.5, from about 0.5 to about 5, from about 0.5 to about 4.8, from about 0.5 to about 4.5, from about 0.5 to about 4.2, from about 0.5 to about 4.0, from about 0.5 to about 3.8, from about 0.5 to about 3.5, from about 0.5 to about 3.2, from about 0.5 to about 3.0, from about 0.5 to about 2.8, from about 0.5 to about 2.5, from about 0.5 to about 2.2, from about 0.5 to about 2.0, from about 0.5 to about 1.8, from about 0.5 to about 1.5, from about 0.5 to about 1.2, from about 0.5 to about 1.0, from about 0.5 to about 0.8, about 0.8 to about 6.0, about 0.8 to about 5.5, from about 0.8 to about 5, from about 0.8 to about 4.8, from about 0.8 to about 4.5, from about 0.8 to about 4.2, from about 0.8 to about 4.0, from about 0.8 to about 3.8, from about 0.8 to about 3.5, from about 0.8 to about 3.2, from about 0.8 to about 3.0, from about 0.8 to about 2.8, from about 0.8 to about 2.5, from about 0.8 to about 2.2, from about 0.8 to about 2.0, from about 0.8 to about 1.8, from about 0.8 to about 1.5, from about 0.8 to about 1.2, from about 0.8 to about 1.0, about 1.0 to about 6.0, about 1.0 to about 5.5, from about 1.0 to about 5.0, from about 1.0 to about 4.8, from about 1.0 to about 4.5, from about 1.0 to about 4.2, from about 1.0 to about 4.0, from about 1.0 to about 3.8, from about 1.0 to about 3.5, from about 1.0 to about 3.2, from about 1.0 to about 3.0, from about 1.0 to about 2.8, from about 1.0 to about 2.5, from about 1.0 to about 2.2, from about 1.0 to about 2.0, from about 1.0 to about 1.8, from about 1.0 to about 1.5, from about 1.0 to about 1.2, about 1.2 to about 6.0, about 1.2 to about 5.5, from about 1.2 to about 5.0, from about 1.2 to about 4.8, from about 1.2 to about 4.5, from about 1.2 to about 4.2, from about 1.2 to about 4.0, from about 1.2 to about 3.8, from about 1.2 to about 3.5, from about 1.2 to about 3.2, from about 1.2 to about 3.0, from about 1.2 to about 2.8, from about 1.2 to about 2.5, from about 1.2 to about 2.2, from about 1.2 to about 2.0, from about 1.2 to about 1.8, from about 1.2 to about 1.5, about 1.5 to about 6.0, about 1.5 to about 5.5, from about 1.5 to about 5.0, from about 1.5 to about 4.8, from about 1.5 to about 4.5, from about 1.5 to about 4.2, from about 1.5 to about 4.0, from about 1.5 to about 3.8, from about 1.5 to about 3.5, from about 1.5 to about 3.2, from about 1.5 to about 3.0, from about 1.5 to about 2.8, from about 1.5 to about 2.5, from about 1.5 to about 2.2, from about 1.5 to about 2.0, from about 1.5 to about 1.8, about 1.8 to about 6.0, about 1.8 to about 5.5, from about 1.8 to about 5.0, from about 1.8 to about 4.8, from about 1.8 to about 4.5, from about 1.8 to about 4.2, from about 1.8 to about 4.0, from about 1.8 to about 3.8, from about 1.8 to about 3.5, from about 1.8 to about 3.2, from about 1.8 to about 3.0, from about 1.8 to about 2.8, from about 1.8 to about 2.5, from about 1.8 to about 2.2, from about 1.8 to about 2.0, about 2.0 to about 6.0, about 2.0 to about 5.5, from about 2.0 to about 5.0, from about 2.0 to about 4.8, from about 2.0 to about 4.5, from about 2.0 to about 4.2, from about 2.0 to about 4.0, from about 2.0 to about 3.8, from about 2.0 to about 3.5, from about 2.0 to about 3.2, from about 2.0 to about 3.0, from about 2.0 to about 2.8, from about 2.0 to about 2.5, from about 2.0 to about 2.2, about 2.2 to about 6.0, about 2.2 to about 5.5, from about 2.2 to about 5.0, from about 2.2 to about 4.8, from about 2.2 to about 4.5, from about 2.2 to about 4.2, from about 2.2 to about 4.0, from about 2.2 to about 3.8, from about 2.2 to about 3.5, from about 2.2 to about 3.2, from about 2.2 to about 3.0, from about 2.2 to about 2.8, from about 2.2 to about 2.5, about 2.5 to about 6.0, about 2.5 to about 5.5, from about 2.5 to about 5.0, from about 2.5 to about 4.8, from about 2.5 to about 4.5, from about 2.5 to about 4.2, from about 2.5 to about 4.0, from about 2.5 to about 3.8, from about 2.5 to about 3.5, from about 2.5 to about 3.2, from about 2.5 to about 3.0, from about 2.5 to about 2.8, from about 2.8 to about 6.0, about 2.8 to about 5.5, from about 2.8 to about 5.0, from about 2.8 to about 4.8, from about 2.8 to about 4.5, from about 2.8 to about 4.2, from about 2.8 to about 4.0, from about 2.8 to about 3.8, from about 2.8 to about 3.5, from about 2.8 to about 3.2, from about 2.8 to about 3.0, from about 3.0 to about 6.0, from about 3.5 to about 5.5, from about 3.0 to about 5.0, from about 3.0 to about 4.8, from about 3.0 to about 4.5, from about 3.0 to about 4.2, from about 3.0 to about 4.0, from about 3.0 to about 3.8, from about 3.0 to about 3.5, from about 3.0 to about 3.2, from about 3.2 to about 6.0, from about 3.2 to about 5.5, from about 3.2 to about 5, from about 3.2 to about 4.8, from about 3.2 to about 4.5, from about 3.2 to about 4.2, from about 3.2 to about 4.0, from about 3.2 to about 3.8, from about 3.2 to about 3.5, from about 3.5 to about 6.0, from about 3.5 to about 5.5, from about 3.5 to about 5, from about 3.5 to about 4.8, from about 3.5 to about 4.5, from about 3.5 to about 4.2, from about 3.5 to about 4.0, from about 3.5 to about 3.8, from about 3.8 to about 5, from about 3.8 to about 4.8, from about 3.8 to about 4.5, from about 3.8 to about 4.2, from about 3.8 to about 4.0, from about 4.0 to about 6.0, from about 4.0 to about 5.5, from about 4.0 to about 5, from about 4.0 to about 4.8, from about 4.0 to about 4.5, from about 4.0 to about 4.2, from about 4.2 to about 5, from about 4.2 to about 4.8, from about 4.2 to about 4.5, from about 4.5 to about 5, from about 4.5 to about 4.8, or from about 4.8 to about 5.

In a particular embodiment comprising an acid, the pH can be from about 0.01 to about 6.0, 0.2 to about 6.0, about 0.2 to about 5.0 or about 0.2 to about 4.5.

Exemplary acids can include, but are not limited to, inorganic acids such as hydrochloric acid, nitric acid, sulfuric acid, hydrofluoric acid, phosphoric acid, boric acid and oxalic acid; and organic acids such as acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, shikimic acid, 2-ethylhexanoic acid, oleic acid, stearic acid, linoleic acid, linolenic acid, salicylic acid, benzoic acid, p-amino-benzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, tartaric acid, succinic acid, itaconic acid, mesaconic acid, citraconic acid, malic acid, a hydrolysate of glutaric acid, a hydrolysate of maleic anhydride, a hydrolysate of phthalic anhydride, and the like. These acids may be used either singly or in combination. In a particular embodiment, the acid can comprise or be hydrochloric acid.

III.B. Compounds of Formula (VIII)

The methods provided herein comprise the step of adding at least one compound of Formula $[Z^{15}Z^{16}SiCH_2]_3$ (VIII) into the aqueous mixture to form a solution, wherein each $Z^{15}$ can be a $C_1$-$C_4$ alkoxy group and each $Z^{16}$ can be a $C_1$-$C_4$ alkoxy group or a $C_1$-$C_4$ alkyl group.

In one embodiment, each $Z^{15}$ can be a $C_1$-$C_3$ alkoxy or methoxy or ethoxy.

Additionally or alternatively, each $Z^{16}$ can be a $C_1$-$C_4$ alkoxy, a $C_1$-$C_3$ alkoxy or methoxy or ethoxy. Additionally or alternatively, each $Z^{16}$ can comprise methyl, ethyl or propyl, such as a methyl or ethyl.

Additionally or alternatively, each $Z^{15}$ can be a $C_1$-$C_2$ alkoxy group and $R^2$ can be a $C_1$-$C_2$ alkoxy group or a $C_1$-$C_2$ alkyl group.

Additionally or alternatively, each $Z^{15}$ can be methoxy or ethoxy and each $R^2$ can be methyl or ethyl.

In a particular embodiment, $Z^{15}$ and $Z^{16}$ can be ethoxy, such that the compound corresponding to Formula (VIII) can be 1,1,3,3,5,5-hexaethoxy-1,3,5-trisilacyclohexane, ($[(EtO)_2SiCH_2]_3$).

In a particular embodiment, $Z^{15}$ can be ethoxy and $Z^{16}$ can be methyl, such that compound corresponding to Formula (VIII) can be 1,3,5-trimethyl-1,3,5-triethoxy-1,3,5-trisilacyclohexane, ($[EtOCH_3SiCH_2]_3$).

Additionally or alternatively, the method can further comprise adding to the aqueous mixture a further compound Formula (VIII), which may be the same or different. In the case where different compounds of Formula (VIII) are added, an organosilica material support can be obtained which is a copolymer comprising at least one independent unit of Formula (I) as described herein and at least one independent unit of Formula (III) as described herein. For example, 1,1,3,3,5,5-hexaethoxy-1,3,5-trisilacyclohexane, ($[(EtO)_2SiCH_2]_3$) and 1,3,5-trimethyl-1,3,5-triethoxy-1,3,5-trisilacyclohexane, ($[EtOCH_3SiCH_2]_3$) may be added to the aqueous mixture.

When more than one compound of Formula (VIII) is used, the respective compounds may be used in a wide variety of molar ratios. For example, if two compounds of Formula (VIII) are used, the molar ratio of each compound may vary from 1:99 to 99:1, such as from 10:90 to 90:10. The use of different compounds of Formula (VIII) allows to tailor the properties of the organosilica materials made by the process of the disclosure, as will be further explained in the examples and in the section of this specification describing the properties of the organosilicas made by the present processes.

When more than one compound of Formula (VIII) is used, the respective compounds may be used in a wide variety of molar ratios. For example, if two compounds of Formula (VIII) are used, the molar ratio of each compound may vary from 1:99 to 99:1, such as from 10:90 to 90:10. The use of different compounds of Formula (VIII) allows to tailor the properties of the organosilica materials made by the process of the disclosure, as will be further explained in the examples and in the section of this specification describing the properties of the organosilicas made by the present processes.

III.C. Compounds of Formula (IX)

The methods provided herein can comprise the step of adding at least one cyclic compound of Formula

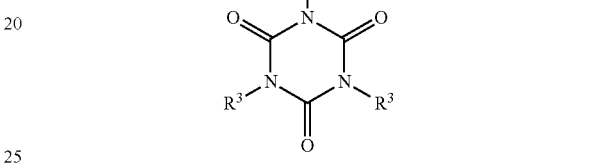

(IX)

into the aqueous mixture to form a solution, wherein each $R^3$ independently can be a $X^7OX^8X^9SiX^{10}$ group, wherein each $X^7$ can be a $C_1$-$C_4$ alkyl group; $X^8$ and $X^9$ each independently can be a $C_1$-$C_4$ alkyl group or a $C_1$-$C_4$ alkoxy group; and each $X^{10}$ can be a $C_1$-$C_8$ alkylene group bonded to a nitrogen atom of the cyclic compound.

In various embodiments, each $X^7$ can be a $C_1$-$C_4$ alkyl, a $C_1$-$C_3$ alkyl, a $C_1$-$C_2$ alkyl or methyl.

Additionally or alternatively, $X^8$ and $X^9$ each independently can be a $C_1$-$C_4$ alkyl group, a $C_1$-$C_3$ alkyl group, a $C_1$-$C_2$ alkyl group or methyl.

Additionally or alternatively, $X^8$ and $X^9$ each independently can be a $C_1$-$C_4$ alkoxy group, a $C_1$-$C_3$ alkoxy group, a $C_1$-$C_2$ alkoxy group or methoxy.

Additionally or alternatively, $X^8$ and $X^9$ each independently can be a $C_1$-$C_2$ alkyl group or a $C_1$-$C_2$ alkoxy group.

Additionally or alternatively, each $X^7$ can be $C_1$-$C_2$ alkyl group; and $X^8$ and $X^9$ each independently can be a $C_1$-$C_2$ alkyl group or a $C_1$-$C_2$ alkoxy group.

Additionally or alternatively, each $X^{10}$ can be a $C_1$-$C_7$ alkylene group bonded to a nitrogen atom of the cyclic compound, a $C_1$-$C_7$ alkylene group bonded to a nitrogen atom of the cyclic compound, a $C_1$-$C_6$ alkylene group bonded to a nitrogen atom of the cyclic compound, a $C_1$-$C_4$ alkylene group bonded to a nitrogen atom of the cyclic compound, a $C_1$-$C_3$ alkylene group bonded to a nitrogen atom of the cyclic compound, a $C_1$-$C_2$ alkylene group bonded to a nitrogen atom of the cyclic compound, or —$CH_2$— bonded to a nitrogen atom of the cyclic compound.

Additionally or alternatively, each $X^7$ can be a $C_1$-$C_2$ alkyl group; $X^8$ and $X^9$ each independently can be a $C_1$-$C_2$ alkyl group or a $C_1$-$C_2$ alkoxy group; and $X^{10}$ can be a $C_1$-$C_4$ alkylene group bonded to a nitrogen atom of the cyclic compound.

In a particular embodiment, each $X^7$ can be methyl; $X^8$ and $X^9$ each independently can be methoxy; and $X^{10}$ can be —$CH_2CH_2CH_2$—, such that the compound corresponding to Formula (IX) can be tris(3-trimethoxysilylpropyl)isocyanurate. In one embodiment, a compound of Formula (IX) (e.g., tris(3-trimethoxysilylpropyl)isocyanurate) can be added to the aqueous mixture and no compound of Formula (VIII) is added to obtain an organosilica material which is a polymer comprising independent units of Formula (II).

Additionally or alternatively, the method can further comprise adding to the aqueous mixture a further compound Formula (IX), which may be the same or different.

In another particular embodiment, a compound of Formula (VIII) and a compound of Formula (IX) may be added to the aqueous mixture to obtain an organosilica material which is a copolymer comprising at least one independent unit of Formula (I) as described herein and at least one independent unit of Formula (II) as described herein. For example, 1,1,3,3,5,5-hexaethoxy-1,3,5-trisilacyclohexane, ([(EtO)$_2$SiCH$_2$]$_3$) and tris(3-trimethoxysilylpropyl)isocyanurate may be added to the aqueous mixture.

The molar ratio of compound of Formula (VIII) to compound of Formula (IX) may vary within wide limits, such as from about 99:1 to about 1:99, from about 1:5 to about 5:1, from about 4:1 to about 1:4 or from about 3:2 to about 2:3. For example, a molar ratio of compound of Formula (VIII) to compound of Formula (IX) can be from about 4:1 to 1:4 or from about 2.5:1 to about 1:2.5, about 2:1 to about 1:2, such as about 1.5:1 to about 1.5:1.

III.D. Compounds of Formula (X)

In additional embodiments, the methods provided herein can comprise adding to the aqueous solution a compound of formula [X$^5$OX$^6$SiCH$_2$]$_3$ (X), to obtain an organosilica material which is a copolymer comprising at least one independent unit of Formula (I) and/or Formula (II) as described herein and at least one independent unit of Formula (III) as described herein, wherein each X$^5$ represents a C$_1$-C$_4$ alkyl group and each X$^6$ represents a C$_1$-C$_4$ alkyl group or a C$_1$-C$_4$ alkoxy group.

In various embodiments, each X$^5$ can be a C$_1$-C$_4$ alkyl group, a C$_1$-C$_3$ alkyl group, a C$_1$-C$_2$ alkyl group or methyl.

Additionally or alternatively, each X$^6$ can be a C$_1$-C$_4$ alkyl group, a C$_1$-C$_3$ alkyl group, a C$_1$-C$_2$ alkyl group or methyl.

Additionally or alternatively, each X$^6$ can be a C$_1$-C$_4$ alkoxy group, a C$_1$-C$_3$ alkoxy group, a C$_1$-C$_2$ alkoxy group or methoxy.

Additionally or alternatively, each X$^6$ can be a C$_1$-C$_2$ alkyl group or a C$_1$-C$_2$ alkoxy group.

Additionally or alternatively, each X$^5$ can be a C$_1$-C$_2$ alkyl group and each X$^6$ can be a C$_1$-C$_2$ alkyl group or a C$_1$-C$_2$ alkoxy group.

In a particular embodiment, each X$^5$ can be ethyl and each X$^6$ can be ethoxy, such that the compound corresponding to Formula (X) can be 1,1,3,3,5,5-hexaethoxy-1,3,5-trisilacyclohexane, ([(EtO)$_2$SiCH$_2$]$_3$).

In a particular embodiment, each X$^5$ can be ethyl and each X$^6$ can be methyl, such that compound corresponding to Formula (X) can be 1,3,5-trimethyl-1,3,5-triethoxy-1,3,5-trisilacyclohexane, ([EtOCH$_3$SiCH$_2$]$_3$).

In another particular embodiment, tris(3-trimethoxysilylpropyl)isocyanurate and 1,1,3,3,5,5-hexaethoxy-1,3,5-trisalacyclohexane can be added to aqueous mixture to obtain an organosilica material with is copolymer comprising independent units of Formula (II) and independent units of Formula (I) or (III).

When more than one compound of Formula (X) is used, the respective compounds may be used in a wide variety of molar ratios. For example, if two compounds of Formula (IIIa) are used, the molar ratio of each compound may vary from 1:99 to 99:1, such as from 10:90 to 90:10. The use of different compounds of Formula (IIIa) allows to tailor the properties of the organosilica materials made by the process of the disclosure, as will be further explained in the examples and in the section of this specification describing the properties of the organosilicas made by the present processes.

The molar ratio of compound of Formula (VIII) to compound of Formula (X) may vary within wide limits, such as from about 99:1 to about 1:99, from about 1:5 to about 5:1, from about 4:1 to about 1:4 or from about 3:2 to about 2:3. For example, a molar ratio of compound of Formula (VIII) to compound of Formula (X) can be from about 4:1 to 1:4 or from about 2.5:1 to about 1:2.5, about 2:1 to about 1:2, such as about 1.5:1 to about 1.5:1.

III.E. Compounds of Formula (XI)

In additional embodiments, the methods provided herein can further comprise adding to the aqueous solution a compound of Formula Z$^{17}$OZ$^{18}$Z$^{19}$Z$^{20}$Si (XI) to obtain an organosilica material which is a copolymer comprising at least one independent unit of Formula (I) and/or Formula (II) as described herein, at least one independent unit of Formula (IV) as described herein and optionally at least one independent unit of Formula (III) as described herein, wherein each Z$^{17}$ can be a C$_1$-C$_6$ alkyl group, and Z$^{18}$, Z$^{19}$ and Z$^{20}$ each independently can be selected from the group consisting of a C$_1$-C$_6$ alkyl group, a C$_1$-C$_6$ alkoxy group, a nitrogen-containing C$_1$-C$_{10}$ alkyl group, a nitrogen-containing heteroaralkyl group, and a nitrogen-containing optionally substituted heterocycloalkyl group.

Additionally or alternatively, each Z$^{17}$ can be a C$_1$-C$_6$ alkyl group, and Z$^{18}$, Z$^{19}$ and Z$^{20}$ each independently can be selected from the group consisting of a C$_1$-C$_6$ alkyl group and a C$_1$-C$_6$ alkoxy group. Additionally or alternatively, Z$^{18}$, Z$^{19}$ and Z$^{20}$ each independently optionally can be a nitrogen-containing C$_1$-C$_{10}$ alkyl group, a nitrogen-containing heteroaralkyl group, and a nitrogen-containing optionally substituted heterocycloalkyl group.

In various aspects, each Z$^{17}$ can be a C$_1$-C$_5$ alkyl group, a C$_1$-C$_4$ alkyl group, a C$_1$-C$_3$ alkyl group, a C$_1$-C$_2$ alkyl group, or methyl. In particular, Z$^{17}$ can be methyl or ethyl.

Additionally or alternatively, Z$^{18}$, Z$^{19}$ and Z$^{20}$ can be each independently a C$_1$-C$_5$ alkyl group, a C$_1$-C$_4$ alkyl group, a C$_1$-C$_3$ alkyl group, a C$_1$-C$_2$ alkyl group, or methyl.

Additionally or alternatively, each Z$^{17}$ can be a C$_1$-C$_2$ alkyl group and Z$^{18}$, Z$^{19}$ and Z$^{20}$ can be each independently a C$_1$-C$_2$ alkyl group.

Additionally or alternatively, Z$^{18}$, Z$^{19}$ and Z$^{20}$ can be each independently a C$_1$-C$_5$ alkoxy group, a C$_1$-C$_4$ alkoxy group, a C$_1$-C$_3$ alkoxy group, a C$_1$-C$_2$ alkoxy group, or methoxy.

Additionally or alternatively, each Z$^{17}$ can be a C$_1$-C$_2$ alkyl group and Z$^{18}$, Z$^{19}$ and Z$^{20}$ can be each independently a C$_1$-C$_2$ alkoxy group.

Additionally or alternatively, each Z$^{17}$ can be a C$_1$-C$_2$ alkyl group and Z$^{18}$, Z$^{19}$ and Z$^{20}$ can be each independently a C$_1$-C$_2$ alkyl group or a C$_1$-C$_2$ alkoxy group.

Additionally or alternatively, Z$^{18}$, Z$^{19}$ and Z$^{20}$ can be each independently a nitrogen-containing C$_1$-C$_9$ alkyl group, a nitrogen-containing C$_1$-C$_8$ alkyl group, a nitrogen-containing C$_1$-C$_7$ alkyl group, a nitrogen-containing C$_1$-C$_6$ alkyl group, a nitrogen-containing C$_1$-C$_5$ alkyl group, a nitrogen-containing C$_1$-C$_4$ alkyl group, a nitrogen-containing C$_1$-C$_3$ alkyl group, a nitrogen-containing C$_1$-C$_2$ alkyl group, or a methylamine. In particular, Z$^{18}$, Z$^{19}$ and Z$^{20}$ can be each independently a nitrogen-containing C$_2$-C$_{10}$ alkyl group, a nitrogen-containing C$_3$-C$_{10}$ alkyl group, a nitrogen-containing C$_3$-C$_9$ alkyl group, or a nitrogen-containing C$_3$-C$_8$ alkyl group. The aforementioned nitrogen-containing alkyl groups may have one or more nitrogen atoms (e.g., 2, 3, etc.). Examples of nitrogen-containing C$_1$-C$_{10}$ alkyl groups include, but are not limited to,

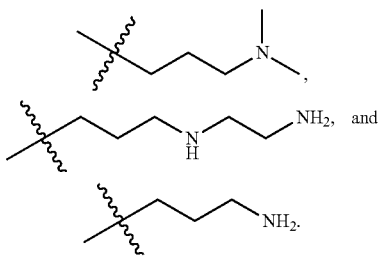

Additionally or alternatively, each $Z^{17}$ can be a $C_1$-$C_2$ alkyl group and $Z^{18}$, $Z^{19}$ and $Z^{20}$ can be each independently a nitrogen-containing $C_3$-$C_8$ alkyl group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group, a $C_1$-$C_2$ alkoxy group or a nitrogen-containing $C_3$-$C_8$ alkyl group.

Additionally or alternatively, $Z^{18}$, $Z^{19}$ and $Z^{20}$ can be each independently a nitrogen-containing heteroaralkyl group. The nitrogen-containing heteroaralkyl group can be a nitrogen-containing $C_4$-$C_{12}$ heteroaralkyl group, a nitrogen-containing $C_4$-$C_{10}$ heteroaralkyl group, or a nitrogen-containing $C_4$-$C_8$ heteroaralkyl group. Examples of nitrogen-containing heteroaralkyl groups include but are not limited to pyridinylethyl, pyridinylpropyl, pyridinylmethyl, indolylmethyl, pyrazinylethyl, and pyrazinylpropyl. The aforementioned nitrogen-containing heteroaralkyl groups may have one or more nitrogen atoms (e.g., 2, 3, etc.).

Additionally or alternatively, each $Z^{17}$ can be a $C_1$-$C_2$ alkyl group and $Z^{18}$, $Z^{19}$ and $Z^{20}$ can be each independently a nitrogen-containing heteroaralkyl group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group, a $C_1$-$C_2$ alkoxy group, a nitrogen-containing $C_3$-$C_8$ alkyl group or a nitrogen-containing heteroaralkyl group.

Additionally or alternatively, $Z^{18}$, $Z^{19}$ and $Z^{20}$ can be each independently a nitrogen-containing heterocycloalkyl group, wherein the heterocycloalkyl group may be optionally substituted with a $C_1$-$C_6$ alkyl group, particularly a $C_1$-$C_4$ alkyl group. The nitrogen-containing heterocycloalkyl group can be a nitrogen-containing $C_4$-$C_{12}$ heterocycloalkyl group, a nitrogen-containing $C_4$-$C_{10}$ heterocycloalkyl group, or a nitrogen-containing $C_4$-$C_8$ heterocycloalkyl group. Examples of nitrogen-containing heterocycloalkyl groups include but are not limited to piperazinylethyl, piperazinylpropyl, piperidinylethyl, piperidinylpropyl. The aforementioned nitrogen-containing heterocycloalkyl groups may have one or more nitrogen atoms (e.g., 2, 3, etc.).

Additionally or alternatively, each $Z^{17}$ can be a $C_1$-$C_2$ alkyl group and $Z^8$, $Z^{19}$ and $Z^{20}$ can be each independently a nitrogen-containing optionally substituted heterocycloalkyl group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group, a $C_1$-$C_2$ alkoxy group, a nitrogen-containing $C_3$-$C_8$ alkyl group, a nitrogen-containing heteroaralkyl group, or a nitrogen-containing optionally substituted heterocycloalkyl group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroaralkyl group, or a nitrogen-containing optionally substituted $C_4$-$C_{10}$ heterocycloalkyl group.

In a particular embodiment, $Z^{17}$ can be ethyl and $Z^{18}$, $Z^{19}$ and $Z^{20}$ can be ethoxy, such that the compound corresponding to Formula (XI) can be tetraethyl orthosilicate (TEOS) ((EtO)$_4$Si).

In another particular embodiment, tris(3-trimethoxysilylpropyl)isocyanurate and tetraethyl orthosilicate (TEOS) ((EtO)$_4$Si) can be added to aqueous mixture to obtain an organosilica material with is copolymer comprising independent units of Formula (II) and independent units of Formula (IV).

In another particular embodiment, a compound of Formula (VIII) can be 1,1,3,3,5,5-hexaethoxy-1,3,5-trisilacyclohexane ([(EtO)$_2$SiCH$_2$]$_3$) and a compound of Formula (XI) can be tetraethyl orthosilicate (TEOS) ((EtO)$_4$Si).

In another particular embodiment, $Z^{17}$ can be ethyl, $Z^{18}$ can be methyl and $Z^{19}$ and $Z^{20}$ can be ethoxy, such that the compound corresponding to Formula (XI) can be methyltriethoxysilane (MTES) ((EtO)$_3$CH$_3$Si).

In another particular embodiment, a compound of Formula (VIII) can be 1,1,3,3,5,5-hexaethoxy-1,3,5-trisilacyclohexane ([(EtO)$_2$SiCH$_2$]$_3$) and a compound of Formula (X) can be methyltriethoxysilane (MTES) ((EtO)$_3$CH$_3$Si).

In another particular embodiment, a compound of Formula (VIII) can be 1,3,5-trimethyl-1,3,5-triethoxy-1,3,5-trisilacyclohexane ([EtOCH$_3$SiCH$_2$]$_3$ and a compound of Formula (XI) can be tetraethyl orthosilicate (TEOS) ((EtO)$_4$Si).

In another particular embodiment, $Z^{17}$ can be ethyl, $Z^{18}$ and $Z^{19}$ can be ethoxy and $Z^{20}$ can be

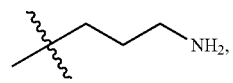

such that the compound corresponding to Formula (XI) can be (3-aminopropyl)triethoxysilane (H$_2$N(CH$_2$)$_3$(EtO)$_3$Si).

In another particular embodiment, a compound of Formula (VIII) can be 1,1,3,3,5,5-hexaethoxy-1,3,5-trisilacyclohexane ([(EtO)$_2$SiCH$_2$]$_3$) and a compound of Formula (XI) can be (3-aminopropyl)triethoxysilane (H$_2$N(CH$_2$)$_3$(EtO)$_3$Si).

In another particular embodiment, $Z^{17}$ can be methyl, $Z^{18}$ and $Z^{19}$ can be methoxy and $Z^{20}$ can be

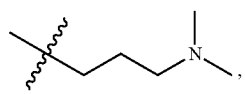 [SMILES: *CCCN(C)C]

such that the compound corresponding to Formula (XI) can be (N,N-dimethylaminopropyl)trimethoxysilane (((CH$_3$)$_2$N(CH$_2$)$_3$)(MeO)$_3$Si).

In another particular embodiment, a compound of Formula (VIII) can be 1,1,3,3,5,5-hexaethoxy-1,3,5-trisilacyclohexane ([(EtO)$_2$SiCH$_2$]$_3$) and a compound of Formula (XI) can be (N,N-dimethylaminopropyl)trimethoxysilane (((CH$_3$)$_2$N(CH$_2$)$_3$)(MeO)$_3$Si).

In another particular embodiment, $Z^{17}$ can be ethyl, $Z^{18}$ and $Z^{19}$ can be ethoxy and $Z^{20}$ can be

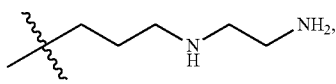 [SMILES: *CCCNCCN]

such that the compound corresponding to Formula (XI) can be (N-(2-aminoethyl)-3-aminopropyltriethoxysilane ((H$_2$N(CH$_2$)$_2$NH(CH$_2$)$_3$)(EtO)$_3$Si).

In another particular embodiment, a compound of Formula (VIII) can be 1,1,3,3,5,5-hexaethoxy-1,3,5-trisilacyclohexane ([(EtO)$_2$SiCH$_2$]$_3$) and a compound of Formula (XI) can be (N-(2-aminoethyl)-3-aminopropyltriethoxysilane ((H$_2$N(CH$_2$)$_2$NH(CH$_2$)$_3$)(EtO)$_3$Si).

In another particular embodiment, $Z^{17}$ can be ethyl, $Z^{18}$ and $Z^{19}$ can be ethoxy and $Z^{20}$ can be

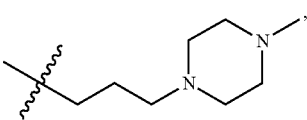 [SMILES: *CCCN1CCN(C)CC1]

such that the compound corresponding to Formula (XI) can be 4-methyl-1-(3-triethoxysilylpropyl)-piperazine.

In another particular embodiment, a compound of Formula (VIII) can be 1,1,3,3,5,5-hexaethoxy-1,3,5-trisilacyclohexane ([(EtO)$_2$SiCH$_2$]$_3$) and a compound of Formula (XI) can be 4-methyl-1-(3-triethoxysilylpropyl)-piperazine.

In another particular embodiment, $Z^{17}$ can be ethyl, $Z^{18}$ and $Z^{19}$ can be ethoxy and $Z^{20}$ can be

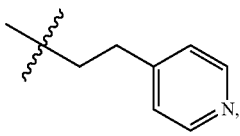

such that the compound corresponding to Formula (XI) can be 4-(2-(triethoxysily)ethyl)pyridine.

In another particular embodiment, a compound of Formula (VIII) can 1,1,3,3,5,5-hexaethoxy-1,3,5-trisilacyclohexane ([(EtO)$_2$SiCH$_2$]$_3$) and a compound of Formula (XI) can be 4-(2-(triethoxysily)ethyl)pyridine.

In another particular embodiment, $Z^{17}$ can be ethyl, $Z^{18}$ and $Z^{19}$ can be ethoxy and $Z^{20}$ can be

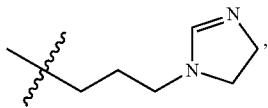 [SMILES: *CCCN1C=NCC1]

such that the compound corresponding to Formula (XI) can be 1-(3-(triethoxysilyl)propyl)-4,5-dihydro-1H-imidazole.

In another particular embodiment, a compound of Formula (VIII) can be 1,1,3,3,5,5-hexaethoxy-1,3,5-trisilacyclohexane ([(EtO)$_2$SiCH$_2$]$_3$) and a compound of Formula (XI) can be 1-(3-(triethoxysilyl)propyl)-4,5-dihydro-1H-imidazole.

The molar ratio of compound of Formula (VIII) or a compound of Formula (IX) to compound of Formula (XI) may vary within wide limits, such as from about 99:1 to about 1:99, from about 1:5 to about 5:1, from about 4:1 to about 1:4 or from about 3:2 to about 2:3. For example, a molar ratio of compound of Formula (VIII) or a compound of Formula (IX) to compound of Formula (XI) can be from about 4:1 to 1:4 or from about 2.5:1 to about 1:2.5, about 2:1 to about 1:2, such as about 1.5:1 to about 1.5:1.

III.F. Compounds of Formula (XII)

In additional embodiments, the methods provided herein can further comprise adding to the aqueous solution a compound of Formula $Z^{21}Z^{22}Z^{23}Si$—$R^4$—Si $Z^{21}Z^{23}Z^{24}$ (XII) to obtain an organosilica material which is a copolymer comprising at least one independent unit Formula (I) and/or Formula (II) as described herein, at least one independent unit of Formula (V) as described herein and optionally at least one independent unit of Formulas (III) and/or (IV) as described herein, wherein each $Z^{21}$ independently can be a $C_1$-$C_4$ alkoxy group; $Z^{22}$ and $Z^{23}$ each independently can be a $C_1$-$C_4$ alkoxy group or a $C_1$-$C_4$ alkyl group; and each $R^4$ can be selected from the group consisting a $C_1$-$C_8$ alkylene group, a $C_2$-$C_8$ alkenylene group, a $C_2$-$C_8$ alkynylene group, a nitrogen-containing $C_2$-$C_{10}$ alkylene group, an optionally substituted $C_6$-$C_{20}$ aralkyl group, and an optionally substituted $C_4$-$C_{20}$ heterocycloalkyl group.

Additionally or alternatively, each $Z^{21}$ independently can be a $C_1$-$C_4$ alkoxy group; $Z^{22}$ and $Z^{23}$ each independently can be a $C_1$-$C_4$ alkoxy group or a $C_1$-$C_4$ alkyl group; and each $R^1$ can be selected from the group consisting a $C_1$-$C_8$ alkylene group, a $C_2$-$C_8$ alkenylene group, and a $C_2$-$C_8$ alkynylene group. Additionally or alternatively, $R^1$ can optionally be a nitrogen-containing $C_1$-$C_{10}$ alkylene group, an optionally substituted $C_6$-$C_{20}$ aralkyl group, and/or an optionally substituted $C_4$-$C_{20}$ heterocycloalkyl group.

In various embodiments, each $Z^{21}$ can be a $C_1$-$C_3$ alkoxy group, a $C_1$-$C_2$ alkoxy group, or methoxy.

Additionally or alternatively, $Z^{22}$ and $Z^{23}$ each independently can be a $C_1$-$C_3$ alkoxy group, a $C_1$-$C_2$ alkoxy group, or methoxy.

Additionally or alternatively, each $Z^{21}$ can be a $C_1$-$C_2$ alkoxy group and $Z^{22}$ and $Z^{23}$ each independently can be a $C_1$-$C_2$ alkoxy group.

Additionally or alternatively, $Z^{22}$ and $Z^{23}$ each independently can be a $C_1$-$C_3$ alkyl group, a $C_1$-$C_2$ alkyl group, or methyl.

Additionally or alternatively, each $Z^{21}$ can be a $C_1$-$C_2$ alkoxy group and $Z^{22}$ and $Z^{23}$ each independently can be a $C_1$-$C_2$ alkyl group.

Additionally or alternatively, $Z^{21}$ can be a $C_1$-$C_2$ alkoxy group and $Z^{22}$ and $Z^{23}$ each independently can be a $C_1$-$C_2$ alkoxy group or a $C_1$-$C_2$ alkyl group.

Additionally or alternatively, each $R^4$ can be a $C_1$-$C_7$ alkylene group, a $C_1$-$C_6$ alkylene group, a $C_1$-$C_5$ alkylene group, a $C_1$-$C_4$ alkylene group, a $C_1$-$C_3$ alkylene group, a $C_1$-$C_2$ alkylene group, or —CH$_2$—.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^7$ can be a $C_1$-$C_2$ alkylene group.

Additionally or alternatively, each $R^4$ can be a $C_2$-$C_7$ alkenylene group, a $C_1$-$C_6$ alkylene group, a $C_2$-$C_5$ alkenylene group, a $C_2$-$C_4$ a alkenylene group, a $C_2$-$C_3$ alkenylene group, or —CH═CH—.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^4$ can be a $C_1$-$C_2$ alkenylene group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^1$ can be a $C_1$-$C_2$ alkylene group or a $C_1$-$C_2$ alkenylene group.

Additionally or alternatively, each $R^4$ can be a $C_2$-$C_7$ alkynylene group, a $C_1$-$C_6$ alkynylene group, a $C_2$-$C_5$ alkynylene group, a $C_2$-$C_4$ a alkynylene group, a $C_2$-$C_3$ alkynylene group, or —C≡C—.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and $R^4$ can be a $C_2$-$C_4$ alkynylene group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^4$ can be a $C_2$-$C_4$ alkylene group, a $C_2$-$C_4$ alkenylene group or a $C_2$-$C_4$ alkynylene group.

Additionally or alternatively, each $R^4$ can be a nitrogen-containing $C_2$-$C_{10}$ alkylene group, a nitrogen-containing $C_3$-$C_{10}$ alkylene group, a nitrogen-containing $C_4$-$C_{10}$ alkylene group, a nitrogen-containing $C_4$-$C_9$ alkylene group, a nitrogen-containing $C_4$-$C_8$ alkylene group, or nitrogen containing $C_3$-$C_8$ alkylene group. The aforementioned nitrogen-containing alkylene groups may have one or more nitrogen atoms (e.g., 2, 3, etc.). Examples of nitrogen-containing alkylene groups include, but are not limited to,

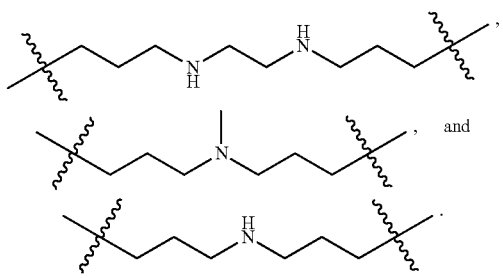

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^4$ can be a nitrogen-containing $C_4$-$C_{10}$ alkylene group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^1$ can be a $C_2$-$C_4$ alkylene group, a $C_2$-$C_4$ alkenylene group, a $C_2$-$C_4$ alkynylene group or a nitrogen-containing $C_4$-$C_{10}$ alkylene group.

Additionally or alternatively, each $R^4$ can be an optionally substituted $C_6$-$C_{20}$ aralkyl, an optionally substituted $C_6$-$C_{14}$ aralkyl, or an optionally substituted $C_6$-$C_{10}$ aralkyl. Examples of $C_6$-$C_{20}$ aralkyls include, but are not limited to, phenymethyl, phenylethyl, and naphthylmethyl. The aralkyl may be optionally substituted with a $C_1$-$C_6$ alkyl group, particularly a $C_1$-$C_4$ alkyl group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^4$ can be an optionally substituted $C_6$-$C_{10}$ aralkyl.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^4$ can be a $C_2$-$C_4$ alkylene group, a $C_2$-$C_4$ alkenylene group, a $C_2$-$C_4$ alkynylene group, or an optionally substituted $C_6$-$C_{10}$ aralkyl.

Additionally or alternatively, $R^4$ can be an optionally substituted $C_4$-$C_{20}$ heterocycloalkyl group, an optionally substituted $C_4$-$C_{16}$ heterocycloalkyl group, an optionally substituted $C_4$-$C_{12}$ heterocycloalkyl group, or an optionally substituted $C_4$-$C_{10}$ heterocycloalkyl group. Examples of $C_4$-$C_{20}$ heterocycloalkyl groups include, but are not limited to, thienylmethyl, furylethyl, pyrrolylmethyl, piperazinylethyl, pyridylmethyl, benzoxazolylethyl, quinolinylpropyl, and imidazolylpropyl. The heterocycloalkyl may be optionally substituted with a $C_1$-$C_6$ alkyl group, particularly a $C_1$-$C_4$ alkyl group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and $R^4$ can be an optionally substituted $C_4$-$C_{12}$ heterocycloalkyl group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^4$ can be a $C_2$-$C_4$ alkylene group, a $C_2$-$C_4$ alkenylene group, a $C_2$-$C_4$ alkynylene group, an optionally substituted $C_6$-$C_{10}$ aralkyl, or an optionally substituted $C_4$-$C_{12}$ heterocycloalkyl group.

In a particular embodiment, $Z^{21}$ and $Z^{22}$ can be ethoxy, $Z^{23}$ can be methyl and $R^4$ can be —$CH_2CH_2$—, such that compound corresponding to Formula (XII) can be 1,2-bis(methyldiethoxysilyl)ethane ($CH_3(EtO)_2Si$—$CH_2CH_2$—$Si(EtO)_2CH_3$).

In another particular embodiment, a compound of Formula (VIII) can be 1,1,3,3,5,5-hexaethoxy-1,3,5-trisilacyclohexane ($[(EtO)_2SiCH_2]_3$), and a compound of Formula (XII) can be 1,2-bis(methyldiethoxysilyl)ethane ($CH_3(EtO)_2Si$—$CH_2CH_2$—$Si(EtO)_2CH_3$).

In another particular embodiment, $Z^{21}$, $Z^{22}$ and $Z^{23}$ can be ethoxy and $R^4$ can be —$CH_2$—, such that compound corresponding to Formula (XII) can be bis(triethoxysilyl)methane (($EtO)_3Si$—$CH_2$—$Si(EtO)_3$).

In another particular embodiment, a compound of Formula (VIII) can be 1,1,3,3,5,5-hexaethoxy-1,3,5-trisilacyclohexane ($[(EtO)_2SiCH_2]_3$) and a compound of Formula (XII) can be bis(triethoxysilyl)methane (($EtO)_3Si$—$CH_2$—$Si(EtO)_3$).

In another particular embodiment, $Z^{21}$, $Z^{22}$ and $Z^{23}$ can be ethoxy and $R^4$ can be —HC=CH—, such that compound corresponding to Formula (XI) can be 1,2-bis(triethoxysilyl)ethylene (($EtO)_3Si$—HC=CH—$Si(EtO)_3$).

In another particular embodiment, a compound of Formula (VIII) can be 1,1,3,3,5,5-hexaethoxy-1,3,5-trisilacyclohexane ($[(EtO)_2SiCH_2]_3$)) and a compound of Formula (XII) can be 1,2-bis(triethoxysilyl)ethylene (($EtO)_3Si$—HC=CH—$Si(EtO)_3$).

In another particular embodiment, a compound of Formula (XII) can be bis(triethoxysilyl)methane (($EtO)_3Si$—$CH_2$—$Si(EtO)_3$) and a compound of Formula (XI) can be tetraethyl orthosilicate (TEOS) (($EtO)_4Si$).

In a particular embodiment, $Z^{21}$, $Z^{22}$ and $Z^{23}$ can be methoxy and $R^4$ can be

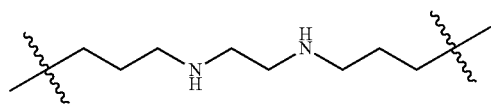

such that compound corresponding to Formula (XII) can be N,N'-bis[(3-trimethoxysilyl)propyl]ethylenediamine.

In another particular embodiment, a compound of Formula (VIII) can be 1,1,3,3,5,5-hexaethoxy-1,3,5-trisilacyclohexane ([(EtO)$_2$SiCH$_2$]$_3$) and a compound of Formula (XII) can be N,N'-bis[(3-trimethoxysilyl)propyl]ethylenediamine.

In another particular embodiment, $Z^{21}$ and $Z^{22}$ can be ethoxy, $Z^{23}$ can be methyl and $R^4$ can be

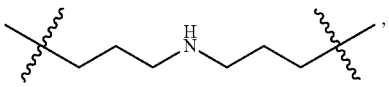 [SMILES: *CCCNCCC*]

such that compound corresponding to Formula (XII) can be bis[(methyldiethoxysilyl)propyl]amine.

In another particular embodiment, Formula (VIII) can be 1,1,3,3,5,5-hexaethoxy-1,3,5-trisilacyclohexane ([(EtO)$_2$SiCH$_2$]$_3$) and a compound of Formula (XII) can be bis[(methyldiethoxysilyl)propyl]amine.

In another particular embodiment, $Z^{21}$ and $Z^{22}$ can be methoxy, $Z^{23}$ can be methyl and $R^4$ can be

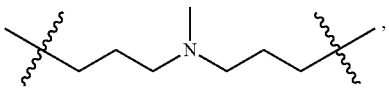 [SMILES: *CCCN(C)CCC*]

such that compound corresponding to Formula (IX) can be bis[(methyldimethoxysilyl)propyl]-N-methylamine.

In another particular embodiment, a compound of Formula (VIII) can be 1,1,3,3,5,5-hexaethoxy-1,3,5-trisilacyclohexane ([(EtO)$_2$SiCH$_2$]$_3$) and a compound of Formula (XII) can be bis[(methyldimethoxysilyl)propyl]-N-methylamine and optionally, no other compounds are added to the aqueous mixture.

The molar ratio of a compound of Formula (VIII) or a compound of Formula (IX) to a compound of Formula (XII) may vary within wide limits, such as from about 99:1 to about 1:99, from about 1:5 to about 5:1, from about 4:1 to about 1:4 or from about 3:2 to about 2:3. For example, a molar ratio of compound of Formula (VIII) or compound of Formula (IX) to compound of Formula (XIII) can be from about 4:1 to 1:4 or from about 2.5:1 to 1:2.5, about 2:1 to about 1:2, such as about 1.5:1 to about 1.5:1.

III.G. Sources of Trivalent Metal Oxide

In additional embodiments, the methods provided herein can comprise adding to the aqueous solution a source of a trivalent metal oxide.

Sources of trivalent metal oxides can include, but are not limited to, corresponding salts, alkoxides, oxides, and/or hydroxides of the trivalent metal, e.g., aluminum sulphate, aluminum nitrate, colloidal alumina, aluminum trihydroxide, hydroxylated alumina, Al$_2$O$_3$, aluminum halides (e.g., AlCl$_3$), NaAlO$_2$, boron nitride, B$_2$O$_3$ and/or H$_3$BO$_3$.

In various aspects, the source of trivalent metal oxide may be a compound of Formula M$^3$(OZ$^{24}$)$_3$ (XIII) to obtain an organosilica material which is a copolymer comprising at least one independent unit Formula (I) and/or Formula (II) as described herein, at least one independent unit of Formula (VI) as described herein and optionally at least one independent unit of Formulas (III), (IV) and/or (V) as described herein, wherein M$^3$ can be a Group 13 metal and each $Z^{24}$ independently can be a C$_1$-C$_6$ alkyl group.

In one embodiment, M$^3$ can be B, Al, Ga, In, Il, or Uut. In particular, M$^3$ can be Al or B.

Additionally or alternatively, each $Z^{24}$ can be a C$_1$-C$_6$ alkyl group, a C$_1$-C$_5$ alkyl group, a C$_1$-C$_4$ alkyl group, a C$_1$-C$_3$ alkyl group, a C$_1$-C$_2$ alkyl group or methyl. In particular, $Z^{15}$ can be methyl, ethyl, propyl or butyl.

Additionally or alternatively, M$^3$ can be Al or B and each $Z^{24}$ can be methyl, ethyl, propyl or butyl.

In a particular embodiment, M$^3$ can be Al and each $Z^{24}$ can be methyl, such that compound corresponding to Formula (XIII) can be aluminum trimethoxide.

In a particular embodiment, M$^3$ can be Al and each $Z^{24}$ can be ethyl, such that compound corresponding to Formula (XIII) can be aluminum triethoxide.

In a particular embodiment, M$^3$ can be Al and each $Z^{24}$ can be propyl, such that compound corresponding to Formula (XIII) can be aluminum isopropoxide.

In a particular embodiment, M$^3$ can be Al and each $Z^{24}$ can be butyl, such that compound corresponding to Formula (XIII) can be aluminum tri-sec-butoxide.

In another particular embodiment, a compound of Formula (VIII) can be 1,1,3,3,5,5-hexaethoxy-1,3,5-trisilacyclohexane, ([(EtO)$_2$SiCH$_2$]$_3$) and a compound of Formula (XIII) can be selected from the group consisting of aluminum trimethoxide, aluminum triethoxide, aluminum isopropoxide, and aluminum tri-sec-butoxide.

In another particular embodiment, a compound of Formula (VIII) can be 1,1,3,3,5,5-hexaethoxy-1,3,5-trisilacyclohexane, ([(EtO)$_2$SiCH$_2$]$_3$) and a compound of Formula (XIII) can be aluminum tri-sec-butoxide.

Additionally or alternatively, the source of trivalent metal oxide may be a compound of Formula (Z$^{16}$O)$_2$M$^4$-O—Si(OZ$^{17}$)$_3$ (XIV) to obtain an organosilica material which is a copolymer comprising at least one independent unit Formula (I) and/or Formula (II) as described herein, at least one independent unit of Formula (VII) as described herein and optionally at least one independent unit of Formulas (III), (IV), (V) and/or (VI) as described herein, wherein M$^4$ can be a Group 13 metal and $Z^{25}$ and $Z^{26}$ each independently can be a C$_1$-C$_6$ alkyl group.

In one embodiment, M$^4$ can be B, Al, Ga, In, Il, or Uut. In particular, M$^4$ can be Al or B.

Additionally or alternatively, $Z^{25}$ and $Z^{26}$ each independently can be a C$_1$-C$_6$ alkyl group, a C$_1$-C$_5$ alkyl group, a C$_1$-C$_4$ alkyl group, a C$_1$-C$_3$ alkyl group, a C$_1$-C$_2$ alkyl group or methyl. In particular, $Z^{25}$ and $Z^{26}$ each independently can be methyl, ethyl, propyl or butyl.

Additionally or alternatively, M$^4$ can be Al or B and $Z^{25}$ and $Z^{26}$ each independently can be methyl, ethyl, propyl or butyl.

Additionally or alternatively, the source of a trivalent metal oxide may be a source of a compound of Formula (XIII) (e.g., AlCl$_3$), and/or a source of a compound of Formula (XIV).

The molar ratio of compound of Formula (VIII) or Formula (IX) to trivalent metal oxide may vary within wide limits, such as from about 99:1 to about 1:99, from about 30:1 to about 1:1, from about 25:1 to about 1:1, from about 20:1 to about 3:1 or from about 20:1 to about 5:1.

III.H. Metal Chelate Sources

In additional embodiments, the methods provided herein can further comprise adding to the aqueous solution a source of metal chelate compounds.

Examples of metal chelate compounds, when present, can include titanium chelate compounds such as triethoxy.mono(acetylacetonato) titanium, tri-n-propoxy.mono(acetylacetonato)titanium, tri-i-propoxy.mono(acetylacetonato)titanium, tri-n-butoxy.mono(acetylacetonato)titanium, tri-sec-butoxy.mono(acetylacetonato)titanium, tri-t-butoxy.mono(acetylacetonato)titanium, diethoxy.bis(acetylacetonato)titanium, di-n-propoxy.bis(acetylacetonato), di-i- propoxy.bis(acetylacetonato)titanium, di-n-butoxy.bis(acetylacetonato)titanium, di-sec-butoxy.bis(acetylacetonato)titanium, di-t-butoxy.bis(acetylacetonato)titanium, monoethoxy.tris(acetylacetonato)titanium, mono-n-propoxy.tris(acetylacetonato) titanium, mono-i-propoxy.tris(acetylacetonato)titanium, mono-n-butoxy. tris(acetylacetonato)titanium, mono-sec-butoxy.tris(acetylacetonato)titanium, mono-t-butoxy-tris(acetylacetonato)titanium, tetrakis(acetylacetonato)titanium, triethoxy.mono(ethylacetoacetaato)titanium, tri-n-propoxy.mono(ethylacetoacetato)titanium, tri-i-propoxy.mono(ethylacetoacetato) titanium, tri-n-butoxy.mono(ethylacetoacetato) titanium, tri-sec-butoxy.mono(ethylacetoacetato) titanium, tri-t-butoxy-mono(ethylacetoacetato)titanium, diethoxy.bis(ethylacetoacetato)titanium, di-n-propoxy.bis(ethylacetoacetato)titanium, di-i-propoxy.bis(ethylacetoacetato)titanium, di-n-butoxy.bis(ethylacetoacetato)titanium, di-sec-butoxy.bis(ethylacetoacetato)titanium, di-t-butoxy.bis(ethylacetoacetato)titanium, monoethoxy.tris(ethylacetoacetato)titanium, mono-n-propoxy.tris(ethylacetoaetato)titanium, mono-i-propoxy.tris(ethylacetoacetato) titanium, mono-n-butoxy.tris(ethylacetoacetato)titanium, mono-sec-butoxy.tris(ethylacetoacetato)titanium, mono-t-butoxy.tris(ethylacetoacetato)titanium, tetrakis(ethylacetoacetato)titanium, mono(acetylacetonato)tris(ethylacetoacetato)titanium, bis(acetylacetonato)bis(ethylacetoacetato)titanium, and tris(acetylacetonato)mono(ethylacetoacetato)titanium; zirconium chelate compounds such as triethoxy.mono(acetylacetonato)zirconium, tri-n-propoxy.mono(acetylacetonato)zirconium, tri-i-propoxy.mono(acetylacetonato)zirconium, tri-n-butoxy.mono(acetylacetonato)zirconium, tri-sec-butoxy.mono(acetylacetonato)zirconium, tri-t-butoxy.mono(acetylacetonato)zirconium, diethoxy.bis(acetylacetonato)zirconium, di-n-propoxy.bis(acetylacetonato)zirconium, di-i-propoxy.bis(acetylacetonato)zirconium, di-n-butoxy.bis(acetylacetonato)zirconium, di-sec-butoxy.bis(acetylacetonato)zirconium, di-t-butoxy.bis(acetylacetonato)zirconium, monoethoxy.tris(acetylacetonato)zirconium, mono-n-propoxy.tris(acetylacetonato)zirconium, mono-i-propoxy.tris(acetylacetonato)zirconium, mono-n-butoxy.tris(acetylacetonato)zirconium, mono-sec-butoxy.tris(acetylacetonato)zirconium, mono-t-butoxy.tris(acetylacetonato)zirconium, tetrakis(acetylacetonato)zirconium, triethoxy.mono(ethylacetoacetato)zirconium, tri-n-propoxy.mono(ethylacetoacetato)zirconium, tri-i-propoxy.mono(ethylacetoacetato)zirconium, tri-n-butoxy.mono(ethylacetoacetato)zirconium, tri-sec-butoxy.mono(ethylacetoacetato)zirconium, tri-t-butoxy.mono(ethylacetoacetato)zirconium, diethoxy.bis(ethylacetoacetato)zirconium, di-n-propoxy.bis(ethylacetoacetato)zirconium, di-i-propoxy.bis(ethylacetoacetato)zirconium, di-n-butoxy.bis(ethylacetoacetato)zirconium, di-sec-butoxy.bis(ethylacetoacetato)zirconium, di-t-butoxy.bis(ethylacetoacetato)zirconium, monoethoxy.tris(ethylacetoacetato)zirconium, mono-n-propoxy.tris(ethylacetoacetato)zirconium, mono-i-propoxy.tris(ethylacetoacetato)zirconium, mono-n-butoxy.tris(ethylacetoacetato)zirconium, mono-sec-butoxy.tris(ethylacetoacetato)zirconium, mono-t-butoxy.tris(ethylacetoacetato)zirconium, tetrakis(ethylacetoacetato)zirconium, mono(acetylacetonato)tris(ethylacetoacetato)zirconium, bis(acetylacetonato)bis(ethylacetoacetato)zirconium, and tris(acetylacetonato)mono(ethylacetoacetato)zirconium; and aluminum chelate compounds such as tris(acetylacetonato)aluminum and tris(ethylacetoacetato)aluminum. Of these, the chelate compounds of titanium or aluminum can be of note, of which the chelate compounds of titanium can be particularly of note. These metal chelate compounds may be used either singly or in combination.

III.I. Molar Ratio

In the methods described herein, a molar ratio of Formula (VIII):Formula (VIII), Formula (VIII):Formula (IX), Formula (VIII):Formula (X), Formula (IX) to Formula (XI) Formula (VIII):Formula (XII), Formula (XII):Formula (XI), Formula (VIII):Formula (XIII), and Formula (VII):Formula (XI) of about 99:1 to about 1:99, about 75:1 to about 1:99, about 50:1 to about 1:99, about 25:1 to about 1:99, about 15:1 to about 1:99, about 50:1 to about 1:50, about 25:1 to about 1:25 or about 15:1 to about 1:15 may be used. For example, molar ratios of about 3:2, about 4:1, about 4:3, about 5:1, about 2:3, about 1:1 about 5:2 and about 15:1 may be used. For example, a molar ratio of Formula (VIII): Formula (VIII) can be about 3:2. A molar ratio of Formula (VIII):Formula (XI) can be about 2:3, about 4:3, about 4:1 or about 3:2. A molar ratio of Formula (VIII):Formula (XII) can be about 2:3, and about 4:1. A molar ratio of Formula (XII):Formula (XI) can be about 5:2, about 1:1, about 1:2 or about 2:3. A molar ratio of Formula (VIII):Formula (XIII) and Formula (VIII):Formula (XIV) can be about 15:1 or about 5:1. A molar ratio of Formula (IX):Formula (VIII) and Formula (IX):Formula (XI) can be about 2:3.

For the sake of the following discussion, the compounds of Formula (VIII), (X) and (XI) and (XII) shall be referred to collectively as starting siloxane. Depending on the choice of starting materials, the solution may have a variety of compositions. For example, if base is used, the solution may have molar ratios of starting siloxane to OH of from about 1:5 to about 1:20, such as from about 1:5 to about 1:15 or from about 1:5 to 1:10, or from about 1:6 to 1:20. If acid is used, the solution may have molar ratios of starting siloxane: $H^+$ of from about 50:1 to about 5:1, such as from about 45:1 to about 10:1. In both cases when acid or base is used, the molar ratios of starting siloxane to $H_2O$ may vary from about 1:50 to about 1:1000, such as from about 1:100 to about 1:500.

III.I. Aging the Solution

The solution formed in the methods described herein can be aged for at least about 4 hours, at least about 6 hours, at least about 12 hours, at least about 18 hours, at least about 24 hours (1 day), at least about 30 hours, at least about 36 hours, at least about 42 hours, at least about 48 hours (2 days), at least about 54 hours, at least about 60 hours, at least about 66 hours, at least about 72 hours (3 days), at least about 96 hours (4 days), at least about 120 hours (5 days) or at least about 144 hours (6 days).

Additionally or alternatively, the solution formed in the methods described herein can be aged for about 4 hours to about 144 hours (6 days), about 4 hours to about 120 hours (5 days), about 4 hours to about 96 hours (4 days), about 4 hours to about 72 hours (3 days), about 4 hours to about 66 hours, about 4 hours to about 60 hours, about 4 hours to about 54 hours, about 4 hours to about 48 hours (2 days), about 4 hours to about 42 hours, about 4 hours to about 36 hours, about 4 hours to about 30 hours, about 4 hours to about 24 hours (1 day), about 4 hours to about 18 hours, about 4 hours to about 12 hours, about 4 hours to about 6 hours, about 6 hours to about 144 hours (6 days), about 6 hours to about 120 hours (5 days), about 6 hours to about 96 hours (4 days), about 6 hours to about 72 hours (3 days), about 6 hours to about 66 hours, about 6 hours to about 60 hours, about 6 hours to about 54 hours, about 6 hours to about 48 hours (2 days), about 6 hours to about 42 hours, about 6 hours to about 36 hours, about 6 hours to about 30 hours, about 6 hours to about 24 hours (1 day), about 6 hours to about 18 hours, about 6 hours to about 12 hours, about 12 hours to about 144 hours (6 days), about 12 hours to about 120 hours (5 days), about 12 hours to about 96 hours (4 days), about 12 hours to about 72 hours (3 days), about 12 hours to about 66 hours, about 12 hours to about 60 hours, about 12 hours to about 54 hours, about 12 hours to about 48 hours (2 days), about 12 hours to about 42 hours, about 12 hours to about 36 hours, about 12 hours to about 30 hours, about 12 hours to about 24 hours (1 day), about 12 hours to about 18 hours, about 18 hours to about 144 hours (6 days), about 18 hours to about 120 hours (5 days), about 18 hours to about 96 hours (4 days), about 18 hours to about 72 hours (3 days), about 18 hours to about 66 hours, about 18 hours to about 60 hours, about 18 hours to about 54 hours, about 18 hours to about 48 hours (2 days), about 18 hours to about 42 hours, about 18 hours to about 36 hours, about 18 hours to about 30 hours, about 18 hours to about 24 hours (1 day), about 24 hours(1 day) to about 144 hours (6 days), about 24 (1 day) hours (1 day) to about 120 hours (5 days), about 24 hours (1 day) to about 96 hours (4 days), about 24 hours (1 day) to about 72 hours (3 days), about 24 hours (1 day) to about 66 hours, about 24 hours (1 day) to about 60 hours, about 24 hours (1 day) to about 54 hours, about 24 hours (1 day) to about 48 hours (2 days), about 24 hours (1 day) to about 42 hours, about 24 hours (1 day) to about 36 hours, about 24 hours (1 day) to about 30 hours, about 30 hours to about 144 hours (6 days), about 30 hours to about 120 hours (5 days), about 30 hours to about 96 hours (4 days), about 30 hours to about 72 hours (3 days), about 30 hours to about 66 hours, about 30 hours to about 60 hours, about 30 hours to about 54 hours, about 30 hours to about 48 hours (2 days), about 30 hours to about 42 hours, about 30 hours to about 36 hours, about 36 hours to about 144 hours (6 days), about 36 hours to about 120 hours (5 days), about 36 hours to about 96 hours (4 days), about 36 hours to about 72 hours (3 days), about 36 hours to about 66 hours, about 36 hours to about 60 hours, about 36 hours to about 54 hours, about 36 hours to about 48 hours (2 days), about 36 hours to about 42 hours, about 42 hours to about 144 hours (6 days), about 42 hours to about 120 hours (5 days), about 42 hours to about 96 hours (4 days), about 42 hours to about 72 hours (3 days), about 42 hours to about 66 hours, about 42 hours to about 60 hours, about 42 hours to about 54 hours, about 42 hours to about 48 hours (2 days), about 48 hours (2 days) to about 144 hours (6 days), about 48 hours (2 days) to about 120 hours (5 days), about 48 hours (2 days) to about 96 hours (4 days), about 48 hours (2 days) to about 72 hours (3 days), about 48 hours (2 days) to about 66 hours, about 48 hours (2 days) to about 60 hours, about 48 hours (2 days) to about 54 hours, about 54 hours to about 144 hours (6 days), about 54 hours to about 120 hours (5 days), about 54 hours to about 96 hours (4 days), about 54 hours to about 72 hours (3 days), about 54 hours to about 66 hours, about 54 hours to about 60 hours, about 60 hours to about 144 hours (6 days), about 60 hours to about 120 hours (5 days), about 60 hours to about 96 hours (4 days), about 60 hours to about 72 hours (3 days), about 60 hours to about 66 hours, about 66 hours to about 144 hours (6 days), about 66 hours to about 120 hours (5 days), about 66 hours to about 96 hours (4 days), about 66 hours to about 72 hours (3 days), about 72 hours (3 days) to about 144 hours (6 days), about 72 hours (3 days) to about 120 hours (5 days), about 72 hours (3 days) to about 96 hours (4 days), about 96 hours (4 days) to about 144 hours (6 days), about 96 hours (4 days) to about 120 hours (5 days), or about 120 hours (5 days) to about 144 hours (6 days).

Additionally or alternatively, the solution formed in the method can be aged at temperature of at least about 10° C., at least about 20° C., at least about 30° C., at least about 40° C., at least about 50° C., at least about 60° C., at least about 70° C., at least about 80° C., at least about 90° C., at least about 100° C., at least about 110° C., at least about 120° C. at least about 130° C., at least about 140° C., at least about 150° C., at least about 175° C., at least about 200° C., at least about 250° C., or about 300° C.

Additionally or alternatively, the solution formed in the method can be aged at temperature of about 10° C. to about 300° C., about 10° C. to about 250° C., about 10° C. to about 200° C., about 10° C. to about 175° C., about 10° C. to about 150° C., about 10° C. to about 140° C., about 10° C. to about 130° C., about 10° C. to about 120° C., about 10° C. to about 110° C., about 10° C. to about 100° C., about 10° C. to about 90° C., about 10° C. to about 80° C., about 10° C. to about 70° C., about 10° C. to about 60° C., about 10° C. to about 50° C., about 20° C. to about 300° C., about 20° C. to about 250° C., about 20° C. to about 200° C., about 20° C. to about 175° C., about 20° C. to about 150° C., about 20° C. to about 140° C., about 20° C. to about 130° C., about 20° C. to about 120° C., about 20° C. to about 110° C., about 20° C. to about 100° C., about 20° C. to about 90° C., about 20° C. to about 80° C., about 20° C. to about 70° C., about 20° C. to about 60° C., about 20° C. to about 50° C., about 30° C. to about 300° C., about 30° C. to about 250° C., about 30° C. to about 200° C., about 30° C. to about 175° C., about 30° C. to about 150° C., about 30° C. to about 140° C., about 30° C. to about 130° C., about 30° C. to about 120° C., about 30° C. to about 110° C., about 30° C. to about 100° C., about 30° C. to about 90° C., about 30° C. to about 80° C., about 30° C. to about 70° C., about 30° C. to about 60° C., about 30° C. to about 50° C., about 50° C. to about 300° C., about 50° C. to about 250° C., about 50° C. to about 200° C., about 50° C. to about 175° C., about 50° C. to about 150° C., about 50° C. to about 140° C., about 50° C. to about 130° C., about 50° C. to about 120° C., about 50° C. to about 110° C., about 50° C. to about 100° C., about 50° C. to about 90° C., about 50° C. to about 80° C., about 50° C. to about 70° C., about 50° C. to about 60° C., about 70° C. to about 300° C., about 70° C. to about 250° C., about 70° C. to about 200° C., about 70° C. to about 175° C., about 70° C. to about 150° C., about 70° C. to about 140° C., about 70° C. to about 130° C., about 70° C. to about 120° C., about 70° C. to about 110° C., about 70° C. to about 100° C., about 70° C. to about 90° C., about 70° C. to about 80° C., about 80° C. to about 300° C., about 80° C. to about 250° C., about 80° C. to about 200° C., about 80° C. to about 175° C., about 80° C. to about 150° C., about 80° C. to about 140° C., about 80° C. to about 130° C., about 80° C. to about 120° C., about 80° C. to about 110° C., about 80° C. to about 100° C., about 80° C. to about 90° C., about 90° C. to about 300° C., about 90° C. to about 250° C., about 90° C. to about 200° C., about 90° C. to about 175° C., about 90° C. to about 150° C., about 90° C. to about 140° C., about 90° C. to about 130° C., about 90° C. to about 120° C., about 90° C. to about 110° C., about 90° C. to about 100° C., about 100° C. to about 300° C., about 100° C. to about 250° C., about 100° C. to about 200° C., about 100° C. to about 175° C., about 100° C. to about 150° C., about 100° C. to about 140° C., about 100° C. to about 130° C., about 100° C. to about 120° C., about 100° C. to about 110° C., about 110° C. to about 300° C., about 110° C. to about 250° C., about 110° C. to about 200° C., about 110° C. to about 175° C., about 110° C. to about 150° C., about 110° C. to about 140° C., about 110° C. to about 130° C., about 110° C. to about 120° C., about 120° C. to about 300° C., about 120° C. to about 250° C., about 120° C. to about 200° C., about 120° C. to about 175° C., about 120° C. to about 150° C., about 120° C. to about 140° C., about 120° C. to about 130° C., about 130° C. to about 300° C., about 130° C. to about 250° C., about 130° C. to about 200° C., about 130° C. to about 175° C., about 130° C. to about 150° C., or about 130° C. to about 140° C.

III.J. Drying the Pre-Product

The methods described herein comprise drying the pre-product (e.g., a gel) to produce an organosilica material support.

In some embodiments, the pre-product (e.g., a gel) formed in the method can be dried at a temperature of greater than or equal to about 50° C., greater than or equal to about 70° C., greater than or equal to about 80° C., greater than or equal to about 100° C., greater than or equal to about 110° C., greater than or equal to about 120° C., greater than or equal to about 150° C., greater than or equal to about 200° C., greater than or equal to about 250° C., greater than or equal to about 300° C., greater than or equal to about 350° C., greater than or equal to about 400° C., greater than or equal to about 450° C., greater than or equal to about 500° C., greater than or equal to about 550° C., or greater than or equal to about 600° C.

Additionally or alternatively, the pre-product (e.g., a gel) formed in the method can be dried at temperature of about 50° C. to about 600° C., about 50° C. to about 550° C., about 50° C. to about 500° C., about 50° C. to about 450° C., about 50° C. to about 400° C., about 50° C. to about 350° C., about 50° C. to about 300° C., about 50° C. to about 250° C., about 50° C. to about 200° C., about 50° C. to about 150° C., about 50° C. to about 120° C., about 50° C. to about 110° C., about 50° C. to about 100° C., about 50° C. to about 80° C., about 50° C. to about 70° C., about 70° C. to about 600° C., about 70° C. to about 550° C., about 70° C. to about 500° C., about 70° C. to about 450° C., about 70° C. to about 400° C., about 70° C. to about 350° C., about 70° C. to about 300° C., about 70° C. to about 250° C., about 70° C. to about 200° C., about 70° C. to about 150° C., about 70° C. to about 120° C., about 70° C. to about 110° C., about 70° C. to about 100° C., about 70° C. to about 80° C., about 80° C. to about 600° C., about 70° C. to about 550° C., about 80° C. to about 500° C., about 80° C. to about 450° C., about 80° C. to about 400° C., about 80° C. to about 350° C., about 80° C. to about 300° C., about 80° C. to about 250° C., about 80° C. to about 200° C., about 80° C. to about 150° C., about 80° C. to about 120° C., about 80° C. to about 110° C., or about 80° C. to about 100° C.

In a particular embodiment, the pre-product (e.g., a gel) formed in the method can be dried at temperature from about 70° C. to about 200° C.

Additionally or alternatively, the pre-product (e.g., a gel) formed in the method can be dried in a $N_2$ and/or air atmosphere.

III.K. Addition of Binder

In additional embodiments, the methods of making an organosilica material can further comprise adding a binder material as described herein. In particular, the binder material may be selected from the group consisting of active and inactive materials, inorganic materials, clays, alumina, silica, silica-alumina, titania, zirconia, or a combination thereof. Particularly, the binder may be silica-alumina, alumina and/or zirconia.

III.L. Optional Further Steps

In some embodiments, the method can further comprise calcining the organosilica material to obtain a silica material. The calcining can be performed in air or an inert gas, such as nitrogen or air enriched in nitrogen. Calcining can take place at a temperature of at least about 300° C., at least about 350° C., at least about 400° C., at least about 450° C., at least about 500° C., at least about 550° C., at least about 600° C., or at least about 650° C., for example at least about 400° C. Additionally or alternatively, calcining can be performed at a temperature of about 300° C. to about 650° C., about 300° C. to about 600° C., about 300° C. to about 550° C., about 300° C. to about 500° C., about 300° C. to about 450° C., about 300° C. to about 400° C., about 300° C. to about 350° C., about 350° C. to about 650° C., about 350° C. to about 600° C., about 350° C. to about 550° C., about 350° C. to about 500° C., about 350° C. to about 450° C., about 350° C. to about 400° C., about 400° C. to about 650° C., about 400° C. to about 600° C., about 400° C. to about 550° C., about 400° C. to about 500° C., about 400° C. to about 450° C., about 450° C. to about 650° C., about 450° C. to about 600° C., about 450° C. to about 550° C., about 450° C. to about 500° C., about 500° C. to about 650° C., about 500° C. to about 600° C., about 500° C. to about 550° C., about 550° C. to about 650° C., about 550° C. to about 600° C. or about 600° C. to about 650° C.

IV. Further Embodiments

The disclosure can additionally or alternately include one or more of the following embodiments.

Embodiment 1

A method for separating an aromatic compound from a lube base stock, the method comprising contacting a lube base stock containing an aromatic compound with an organosilica material, which is a polymer of at least one monomer selected from the group consisting of:

a. a monomer of Formula $[Z^1OZ^2OSiCH_2]_3$ (I), wherein $Z^1$ and $Z^2$ each independently represent a hydrogen atom, a $C_1$-$C_4$ alkyl group, or a bond to a silicon atom of another monomer; and b. a cyclic polyurea monomer of Formula

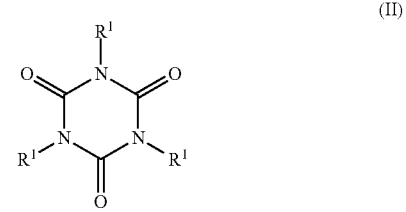

(II)

wherein each $R^1$ independently is a $X^1OX^2X^3SiX^4$ group, wherein each $X^1$ represents a hydrogen atom, a $C_1$-$C_4$ alkyl group, or a bond to a silicon atom of another monomer unit; $X^2$ and $X^3$ each independently represent a hydroxyl group, a $C_1$-$C_4$ alkyl group, a $C_1$-$C_4$ alkoxy group, or an oxygen atom bonded to a silicon atom of another monomer unit; and each $X^4$ represents a $C_1$-$C_8$ alkylene group bonded to a nitrogen atom of the cyclic polyurea.

Embodiment 2

The method of embodiment 1, wherein $Z^1$ and $Z^2$ each independently represent a hydrogen atom, a $C_1$-$C_2$ alkyl group, or a bond to a silicon atom of another monomer.

Embodiment 3

The method of embodiment 2, wherein $Z^1$ and $Z^2$ each independently represent a hydrogen atom, ethyl, or a bond to a silicon atom of another monomer.

Embodiment 4

The method of any one of the previous embodiments, wherein each $X^1$ represents a hydrogen atom, a $C_1$-$C_2$ alkyl group, or a bond to a silicon atom of another monomer unit; $X^2$ and $X^3$ each independently represent a hydroxyl group, a $C_1$-$C_2$ alkyl group, a $C_1$-$C_2$ alkoxy group, or an oxygen atom bonded to a silicon atom of another monomer unit; and each $X^4$ represents a $C_1$-$C_4$ alkylene group bonded to a nitrogen atom of the cyclic polyurea.

Embodiment 5

The method of any one of the previous embodiments, wherein each $X^1$ represents a hydrogen atom, methyl or a bond to a silicon atom of another monomer unit; $X^2$ and $X^3$ each independently represent a hydroxyl group, methoxy or an oxygen atom bonded to a silicon atom of another monomer unit and $X^4$ represents —$CH_2CH_2CH_2$— bonded to a nitrogen atom of the cyclic polyurea.

Embodiment 6

The method of any one of the previous claims, wherein the organosilica material further comprises at least one other monomer selected from the group consisting of:
(i) a further independent unit of Formula (I);
(ii) a further independent unit of Formula (II);
(iii) an independent unit of Formula $[Z^3OZ^4SiCH_2]_3$ (III), wherein each $Z^3$ represents a hydrogen atom, a $C_1$-$C_4$ alkyl group, or a bond to a silicon atom of another monomer and each $Z^4$ represents a $C_1$-$C_6$ alkyl group;
(iv) an independent unit of Formula $Z^5OZ^6Z^7Z^8Si$ (IV), wherein each $Z^5$ represents a hydrogen atom, a $C_1$-$C_4$ alkyl group, or a bond to a silicon atom of another monomer; and $Z^6$, $Z^7$, and $Z^8$ are each independently selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroalkyl group, a nitrogen-containing optionally substituted heterocycloalkyl group, and an oxygen atom bonded to a silicon atom of another monomer;
(v) an independent unit of Formula $Z^9Z^{10}Z^{11}Si$—R—$SiZ^9Z^{10}Z^{11}$ (V), wherein each $Z^9$ independently represents a hydroxyl group, a $C_1$-$C_4$ alkoxy group, or an oxygen atom bonded to a silicon atom of another comonomer; $Z^{10}$ and $Z^{11}$ each independently represent a hydroxyl group, a $C_1$-$C_4$ alkoxy group, a $C_1$-$C_4$ alkyl group, or an oxygen atom bonded to a silicon atom of another monomer; and R is selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl, and an optionally substituted $C_4$-$C_{20}$ heterocycloalkyl group;

(vi) a independent unit of Formula $M^2(OZ^{12})_3$ (VI), wherein $M^1$ represents a Group 13 metal and each $Z^{12}$ independently represents a hydrogen atom, a $C_1$-$C_6$ alkyl, or a bond to a silicon atom of another monomer; and
(vii) an independent unit of Formula $(Z^{13}O)_2M^2$-O—Si$(OZ^{14})_3$ (VII), wherein $M^2$ represents a Group 13 metal and $Z^{13}$ and $Z^{14}$ each independently represent a hydrogen atom, a $C_1$-$C_6$ alkyl group, or a bond to a silicon atom of another monomer.

Embodiment 7

The method of any one of the previous embodiments, wherein at least one unit of Formula (I) and at least one independent unit of Formula (II) is present, wherein $Z^1$ and $Z^2$ each independently represent a hydrogen atom, ethyl, or a bond to a silicon atom of another monomer; each $X^1$ represents a hydrogen atom, methyl or a bond to a silicon atom of another monomer unit; $X^2$ and $X^3$ each independently represent a hydroxyl group, methoxy or an oxygen atom bonded to a silicon atom of another monomer unit and $X^4$ represents —$CH_2CH_2CH_2$— bonded to a nitrogen atom of the cyclic polyurea.

Embodiment 8

The method of embodiment 6 or 7, wherein at least one independent unit of Formula (III) is present, wherein each $Z^3$ represents a hydrogen atom, a $C_1$-$C_2$ alkyl group, or a bond to a silicon atom of another siloxane monomer; and each $Z^4$ represents a $C_1$-$C_2$ alkyl group.

Embodiment 9

The method of any one of embodiments 6-8, wherein each $Z^3$ represents a hydrogen atom, ethyl, or a bond to a silicon atom of another siloxane monomer; and each $Z^4$ represents methyl.

Embodiment 10

The method of any one of embodiments 6-9, wherein at least one independent unit of Formula (IV) is present, wherein each $Z^5$ represents a hydrogen atom, a $C_1$-$C_2$ alkyl group, or a bond to a silicon atom of another monomer; and $Z^6$, $Z^7$, and $Z^8$ are each independently selected from the group consisting of a hydroxyl group, a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroalkyl group, a nitrogen-containing optionally substituted $C_4$-$C_{10}$ heterocycloalkyl group, and an oxygen atom bonded to a silicon atom of another monomer.

Embodiment 11

The method of any one of embodiments 6-10, wherein each $Z^5$ represents a hydrogen atom, methyl, ethyl, or a bond to a silicon atom of another monomer; and $Z^6$, $Z^7$, and $Z^8$ are each independently selected from the group consisting of a hydroxyl group, methyl, methoxy, ethoxy,

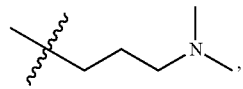

-continued

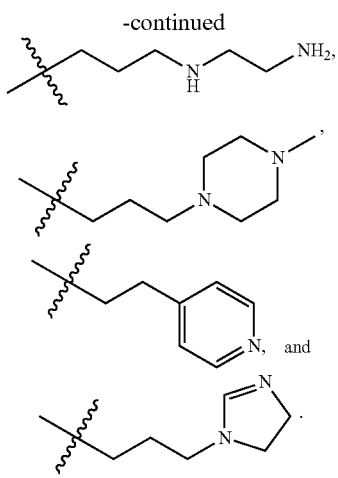

Embodiment 12

The method of any one of embodiments 6-11, wherein at least one independent unit of Formula (V) is present, wherein each $Z^9$ represents a hydroxyl group, a $C_1$-$C_2$ alkoxy group, or an oxygen atom bonded to a silicon atom of another comonomer; $Z^{10}$ and $Z^{11}$ each independently represent a hydroxyl group, a $C_1$-$C_2$ alkoxy group, a $C_1$-$C_2$ alkyl group, or an oxygen atom bonded to a silicon atom of another monomer; and R is selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl and an optionally substituted $C_4$-$C_{12}$ heterocycloalkyl group.

Embodiment 13

The method any one of embodiments 6-12, wherein $Z^9$ represents a hydroxyl group, methoxy, ethoxy, or an oxygen atom bonded to a silicon atom of another comonomer; $Z^{10}$ and $Z^{11}$ each independently represent a hydroxyl group, methoxy, ethoxy, methyl, or an oxygen atom bonded to a silicon atom of another monomer; and R is selected from the group consisting of —$CH_2$—, —$CH_2CH_2$—, —$HC=CH$—,

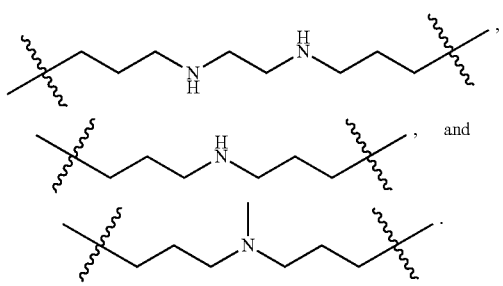

Embodiment 14

The method of any one of embodiments 6-13, wherein at least one independent unit of Formula (VI) is present, wherein $M^1$ is Al or B and each $Z^{12}$ represents a hydrogen atom, a $C_1$-$C_4$ alkyl group, or a bond to a silicon atom or another monomer.

Embodiment 15

The method of any one of embodiments 6-14, wherein at least one independent unit of Formula (VII) is present, wherein $M^2$ is Al or B and $Z^{13}$ and $Z^{14}$ each independently represent a hydrogen atom, a $C_1$-$C_4$ alkyl group, or a bond to a silicon atom of another monomer.

Embodiment 16

The method of any one of the previous embodiments, wherein the organosilica material support has a total surface area of about 200 $m^2$/g to about 2500 $m^2$/g.

Embodiment 17

The method of any one of the previous embodiments, wherein the organosilica material support has a pore volume of about 0.1 $cm^3$/g about 3.0 $cm^3$/g.

Embodiment 18

The method of any one of the previous embodiments, wherein the organosilica material support has an average pore diameter of 2.0 nm to 25 nm.

Embodiment 19

The method of any one of the previous embodiments, wherein the aromatic compound is a single ring aromatic, a double ring aromatic, or a multi-ring aromatic.

Embodiment 20

The method of any one of the previous embodiments, wherein at least 0.1 wt % of the aromatic is removed from the lube base stock.

Embodiment 21

The method of any one of the previous embodiments, wherein the lube base stock is contacted with the organosilica material at a temperature of about 20° C. to about 200° C. and/or a pressure of about 5 psig to about 100 psig.

Embodiment 22

The method of any one of the previous embodiments, wherein the organosilica material has a total aromatic adsorption capacity of at least about 3 g/100 g adsorbent

Embodiment 23

The method of any one of the previous embodiments, wherein the organosilica material has a single ring aromatic separation factor (S12) of at least about 6.

Embodiment 24

The method of any one of the previous embodiments further comprising contacting the lube base stock containing an aromatic compound with another porous material in combination with the organosilica material.

Embodiment 25

The method of embodiment 24, wherein the another porous material is a microporous material, a mesoporous material, an analogous periodic mesoporous material, a metal oxide, a carbon, and a combination thereof.

Embodiment 26

The method of embodiment 24 or 25, wherein the another porous material any one of the previous claims, wherein the adsorbent material is a zeolite material.

Embodiment 27

The method of any one of the previous embodiments, wherein the organosilica material is packed into a column and the lube base stock is contacted therein.

Embodiment 28

An at least partially purified lube base made by the method of any one of the previous embodiments.

EXAMPLES

The following examples are merely illustrative, and do not limit this disclosure in any way.

Example 1—Synthesis of Organosilica Materials

1A. Synthesis of an Isocyanurate Mesoporous Organosilica (MO)

An aqueous mixture of 31.2 g 30 wt % $NH_4OH$ and 39.9 g deionized (DI) water was prepared. To the aqueous mixture, 12 g (30 mmol) of 1,1,3,3,5,5-hexaethoxy-1,3,5-trisilacyclohexane, and 12.2 g (20 mmol) of tris(3-trimethoxysilylpropyl)isocyanurate was added to form a solution. The solution stirred was for a day (18-30 hours) at 20-25° C. The solution was cured at 70° C. in an oven for one day (18-30 hours). The solution was dried at 120° C. under vacuum oven over night (16-24 hours) to produce Sample 1.

1B. Synthesis of Another Isocyanurate MO

An aqueous mixture of 62.3 g 30 wt % $NH_4OH$ and 79.2 g DI water was prepared. To the aqueous mixture, 15.3 g (25 mmol) of tris(3-trimethoxysilylpropyl)isocyanurate was added to form a solution. The solution was stirred for a day (18-30 hours) at 20-25° C. The solution was cured at 70° C. in an oven for one day (18-30 hours). The solution was dried at 120° C. under vacuum oven over night (16-24 hours) to produce Sample 2.

Example 2—Separation of Aromatics Testing

The following experimental procedure was used test adsorption capacity and separation factor (S12).

Experimental Procedure

1. Several different amounts of adsorbents were placed into vials in a high throughput batch reactor unit. Typical amounts were 100, 200, 400, and 800 mg of adsorbents.
2. The adsorbents were pre-treated at a temperature of 120-200° C. to remove physisorbed water from the adsorbents.
3. 3 g of EHC-50 lube base stock were introduced into each of the wells.
4. The wells were agitated at 30° C. for 24 hours.
5. After exposing the adsorbent to the feed for 24 hours, the feed was removed from the well.
6. The fluid was analyzed for aromatics using a Perkin Elmer Lambda 850 UV-Vis spectrophotometer with Scantraq software by FTG. Samples were analyzed at room temp (~15-25 C) in a ~1 mm flow cell. If necessary, samples may be combined with cyclohexane in solution.

Two key parameters, adsorption capacity (g of aromatic adsorbed/100 g of adsorbent) and selectivity (separation factor based upon the ability to removal aromatics in the presence of saturates designated as S12), were evaluated for each of the adsorbents based upon the data collected from the high throughput batch adsorption experiments. It should be noted that each of the adsorbents removed the aromatics unselectively, i.e. the adsorbent did not have a predilection to remove the one-ring aromatics over the other aromatics present, therefore S12 can be used to group the selectivity of all the aromatics in the feed over that of the saturates. The capacity and separation factors calculated based on liquid phase adsorption data was used to evaluate the adsorbent for the aromatic trimming of base stocks. The approach used direct experimental measurements of total moles and composition of liquid before and after contact with adsorbent, adsorbent loading and temperature providing an experimental value of surface excess to determine the adsorption capacity of the adsorbent. In other words, the capacity of the adsorbent was determined from the difference in the aromatics in the feed minus that adsorbed by the porous material divided by the weight of the adsorbent (moles of aromatic/g of adsorbent). Using an average molecular weight of the feed, the grams of aromatic per 100 g of adsorbent can be calculated.

Additionally, the selectivity of the adsorbent can be calculated using Gurvitsch's Rule. The selectivity is defined as (XP1R/BC1R)/(XPNR/BCNR) where XP1R=$n_{ie}$1R/M+BC1R and XPNR=$n_{ie}$NR/M+BCNR; M=molar density of the feed*pore volume of the adsorbent; $n_{ie}$1R=moles of feed*(mole fraction of 1-ring aromatics in the feed−mole fraction of 1 ring aromatics in the bulk after adsorption)/grams of adsorbent; $n_{ie}$NR=moles of feed*(mole fraction of non-aromatics in the feed−mole fraction of non-aromatics in the bulk after adsorption)/grams of adsorbent; BC1R=mole fraction of 1 ring aromatics in the bulk after adsorption; BCNR=mole fraction of non-aromatics in the bulk after adsorption. These calculations can be repeated for any number of aromatic species, i.e. 2-ring, 3-ring, and multi-ring aromatic species, to determine the separation factor for the adsorbent. Typically, for good adsorption processes, separation factor of 3 is acceptable but this can have deleterious effects on the size of the beds, the cycle time between adsorption and regeneration, and the number of beds required for the process.

Figure 2:
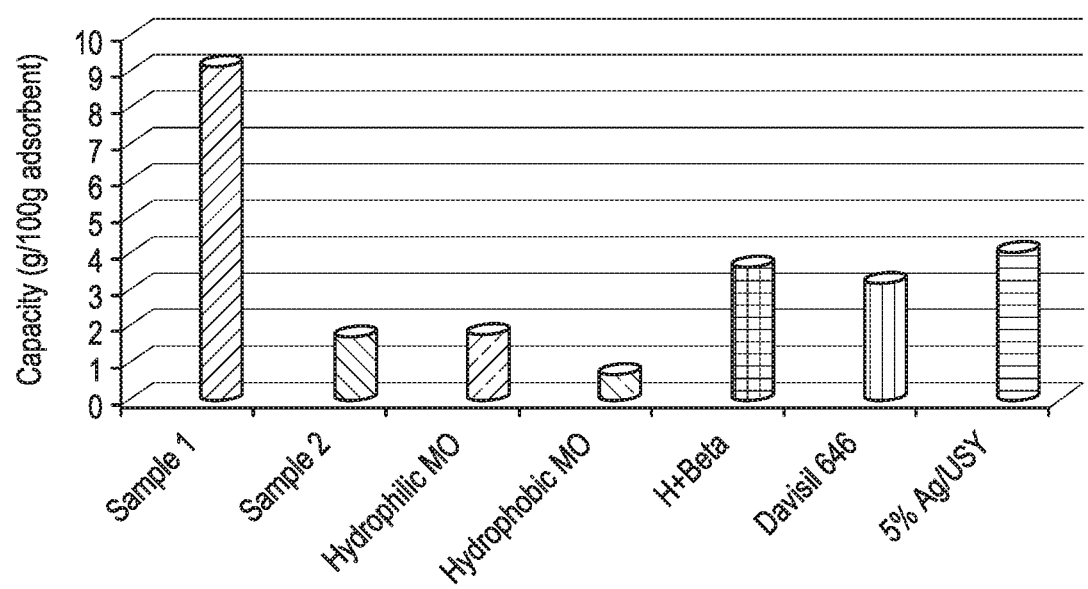
FIG. 2 illustrates aromatic capacity for various materials tested.
Figure 3:
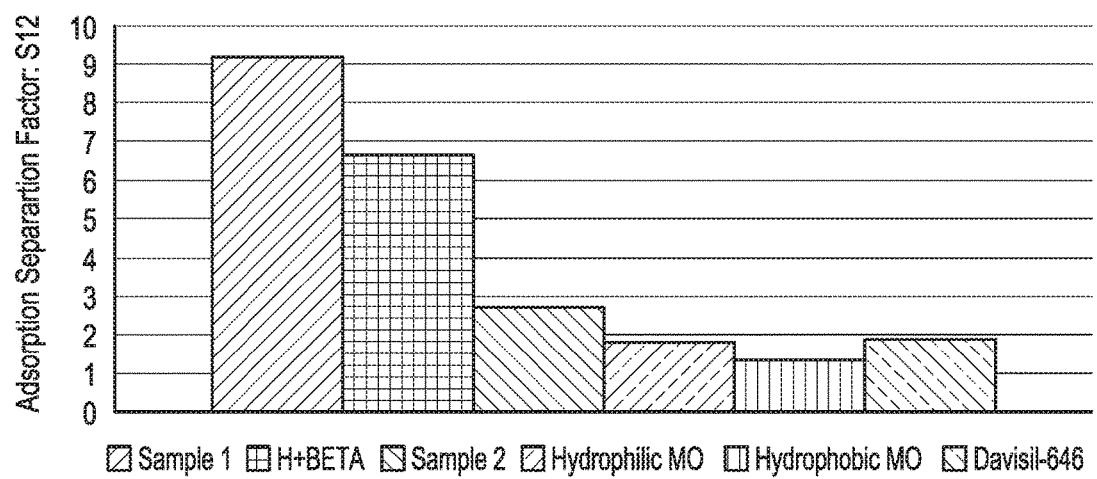
FIG. 3 illustrates adsorption separation factor (S12) for various materials tested.

Samples 1 and 2 were tested along with H+Beta, Davisil 646 (obtained from Sigma-Aldrich) and 5% Ag-USY, hydrophilic MO, and hydrophobic MO for comparison purposes. FIG. 2 shows aromatic adsorption capacity for Sample 1, Sample 2, hydrophilic MO, hydrophobic MO H+Beta, Davisil 646 and 5% Ag-USY. FIG. 3 shows separation factor S12 for Sample 1, Sample 2, hydrophobic MO, hydrophilic MO Davisil 646 and H+Beta. As shown in the FIGS. 2 and 3, Sample 1 showed the highest capacity (almost twice that of the H+Beta and 5% Ag-USY, two of the zeolitic adsorbents) and selectivity towards the adsorption of aromatic species in lube base stocks.

What is claimed is:

1. A method for separating an aromatic compound from a lube base stock, the method comprising contacting a lube base stock containing an aromatic compound with an organosilica material, which is a co-polymer of:

(a) a monomer of Formula $[Z^1OZ^2OSiCH_2]_3$ (I), wherein $Z^1$ and $Z^2$ each independently represent a hydrogen atom, a $C_1$-$C_4$ alkyl group, or a bond to a silicon atom of another monomer; and (b) a cyclic polyurea monomer of Formula

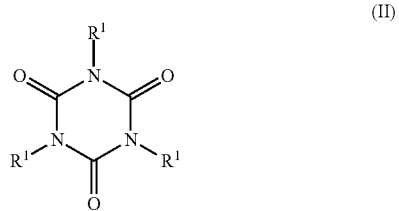

(II)

wherein each $R^1$ independently is a $X^1OX^2X^3SiX^4$ group, wherein each $X^1$ represents a hydrogen atom, a $C_1$-$C_4$ alkyl group, or a bond to a silicon atom of another monomer; $X^2$ and $X^3$ each independently represent a hydroxyl group, a $C_1$-$C_4$ alkyl group, a $C_1$-$C_4$ alkoxy group, or an oxygen atom bonded to a silicon atom of another monomer; and each $X^4$ represents a $C_1$-$C_8$ alkylene group bonded to a nitrogen atom of the cyclic polyurea monomer.

2. The method of claim 1, wherein $Z^1$ and $Z^2$ each independently represent a hydrogen atom, a $C_1$-$C_2$ alkyl group, or a bond to a silicon atom of another monomer.

3. The method of claim 2, wherein $Z^1$ and $Z^2$ each independently represent a hydrogen atom, an ethyl group, or a bond to a silicon atom of another monomer.

4. The method of claim 1, wherein each $X^1$ represents a hydrogen atom, a $C_1$-$C_2$ alkyl group, or a bond to a silicon atom of another monomer; $X^2$ and $X^3$ each independently represent a hydroxyl group, a $C_1$-$C_2$ alkyl group, a $C_1$-$C_2$ alkoxy group, or an oxygen atom bonded to a silicon atom of another monomer; and each $X^4$ represents a $C_1$-$C_4$ alkylene group bonded to a nitrogen atom of the cyclic polyurea monomer.

5. The method of claim 4, wherein each $X^1$ represents a hydrogen atom, a methyl group, or a bond to a silicon atom of another monomer; $X^2$ and $X^3$ each independently represent a hydroxyl group, a methoxy group, or an oxygen atom bonded to a silicon atom of another monomer; and each $X^4$ represents —$CH_2CH_2CH_2$— bonded to a nitrogen atom of the cyclic polyurea monomer.

6. The method of claim 1, wherein the organosilica material is a co-polymer which further comprises at least one other monomer selected from the group consisting of:

(i) an independent unit of Formula $[Z^3OZ^4SiCH_2]_3$ (III), wherein each $Z^3$ represents a hydrogen atom, a $C_1$-$C_4$ alkyl group, or a bond to a silicon atom of another monomer and each $Z^4$ represents a $C_1$-$C_6$ alkyl group;

(ii) an independent unit of Formula $Z^5OZ^6Z^7Z^8Si$ (IV), wherein each $Z^5$ represents a hydrogen atom, a $C_1$-$C_4$ alkyl group, or a bond to a silicon atom of another monomer; and $Z^6$, $Z^7$, and $Z^8$ are each independently selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroalkyl group, a nitrogen-containing optionally substituted heterocycloalkyl group, and an oxygen atom bonded to a silicon atom of another monomer;

(iii) an independent unit of Formula $Z^9Z^{10}Z^{11}Si$—R—$SiZ^9Z^{10}Z^{11}$ (V), wherein each $Z^9$ independently represents a hydroxyl group, a $C_1$-$C_4$ alkoxy group, or an oxygen atom bonded to a silicon atom of another comonomer; $Z^{10}$ and $Z^{11}$ each independently represent a hydroxyl group, a $C_1$-$C_4$ alkoxy group, a $C_1$-$C_4$ alkyl group, or an oxygen atom bonded to a silicon atom of another monomer; and R is selected from the group consisting of a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl group, and an optionally substituted $C_4$-$C_{20}$ heterocycloalkyl group;

(iv) an independent unit of Formula $M^1(OZ^{12})_3$ (VI), wherein $M^1$ represents a Group 13 metal and each $Z^{12}$ independently represents a hydrogen atom, a $C_1$-$C_6$ alkyl group, or a bond to a silicon atom of another monomer; and (v) an independent unit of Formula $(Z^{13}O)_2M^2$-O—Si$(OZ^{14})_3$ (VII), wherein $M^2$ represents a Group 13 metal and $Z^{13}$ and $Z^{14}$ each independently represent a hydrogen atom, a $C_1$-$C_6$ alkyl group, or a bond to a silicon atom of another monomer.

7. The method of claim 6, wherein at least one independent unit of Formula (III) is present, wherein each $Z^3$ represents a hydrogen atom, a $C_1$-$C_2$ alkyl group, or a bond to a silicon atom of another monomer; and each $Z^4$ represents a $C_1$-$C_2$ alkyl group.

8. The method of claim 7, wherein each $Z^3$ represents a hydrogen atom, an ethyl group, or a bond to a silicon atom of another monomer; and each $Z^4$ represents methyl group.

9. The method of claim 6, wherein at least one independent unit of Formula (IV) is present, wherein each $Z^5$ represents a hydrogen atom, a $C_1$-$C_2$ alkyl group, or a bond to a silicon atom of another monomer; and $Z^6$, $Z^7$, and $Z^8$ are each independently selected from the group consisting of a hydroxyl group, a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroalkyl group, a nitrogen-containing optionally substituted $C_4$-$C_{10}$ heterocycloalkyl group, and an oxygen atom bonded to a silicon atom of another monomer.

10. The method of claim 9, wherein each $Z^5$ represents a hydrogen atom, a methyl group, an ethyl group, or a bond to a silicon atom of another monomer; and $Z^6$, $Z^7$, and $Z^8$ are each independently selected from the group consisting of a hydroxyl group, a methyl group, a methoxy group, an ethoxy group,

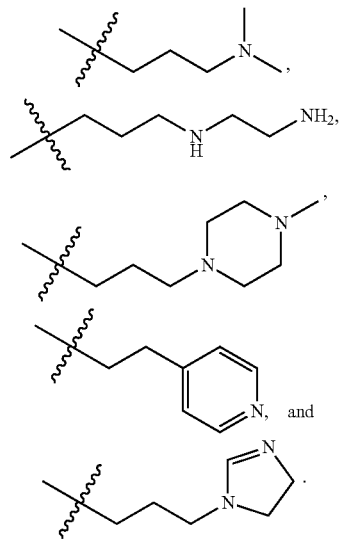

11. The method of claim 6, wherein at least one independent unit of Formula (V) is present, wherein each $Z^9$ represents a hydroxyl group, a $C_1$-$C_2$ alkoxy group, or an oxygen atom bonded to a silicon atom of another comonomer; $Z^{10}$ and $Z^{11}$ each independently represent a hydroxyl group, a $C_1$-$C_2$ alkoxy group, a $C_1$-$C_2$ alkyl group, or an oxygen atom bonded to a silicon atom of another monomer; and R is selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl group, and an optionally substituted $C_4$-$C_{12}$ heterocycloalkyl group.

12. The method of claim 11, wherein each $Z^9$ represents a hydroxyl group, a methoxy group, an ethoxy group, or an oxygen atom bonded to a silicon atom of another comonomer; $Z^{10}$ and $Z^{11}$ each independently represent a hydroxyl group, a methoxy group, an ethoxy group, a methyl group, or an oxygen atom bonded to a silicon atom of another monomer; and R is selected from the group consisting of —CH$_2$—, —CH$_2$CH$_2$—, —HC=CH—,

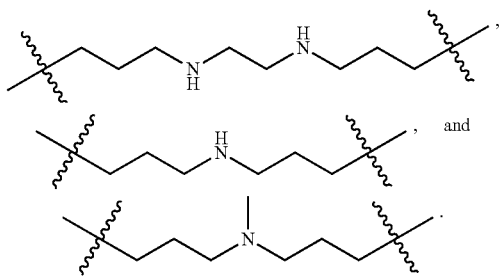

13. The method of claim 6, wherein at least one independent unit of Formula (VI) is present, wherein $M^1$ is Al or B and each $Z^{12}$ represents a hydrogen atom, a $C_1$-$C_4$ alkyl group, or a bond to a silicon atom of another monomer.

14. The method of claim 6, wherein at least one independent unit of Formula (VII) is present, wherein $M^2$ is Al or B and $Z^{13}$ and $Z^{14}$ each independently represent a hydrogen atom, a $C_1$-$C_4$ alkyl group, or a bond to a silicon atom of another monomer.

15. The method of claim 1, wherein the organosilica material has a total surface area of 200 m$^2$/g to 2500 m$^2$/g.

16. The method of claim 1, wherein the organosilica material has a pore volume of 0.1 cm$^3$/g to 3.0 cm$^3$/g.

17. The method of claim 1, wherein the organosilica material has an average pore diameter of 2.0 nm to 25 nm.

18. The method of claim 1, wherein the aromatic compound is a single ring aromatic compound, a double ring aromatic compound, or a multi-ring aromatic compound.

19. The method of claim 1, wherein at least 0.1 wt % of the aromatic compound is removed from the lube base stock after contacting the lube base stock with the organosilica material.

20. The method of claim 1, wherein the lube base stock is contacted with the organosilica material at a temperature of 20° C. to 200° C. and/or a pressure of 5 psig to 100 psig.

21. The method of claim 1, wherein the organosilica material has a total aromatic adsorption capacity of at least 3 g/100 g organosilica material.

22. The method of claim 1, wherein the organosilica material has a single ring aromatic separation factor (S12) of at least 6.

23. The method of claim 1 further comprising contacting the lube base stock containing an aromatic compound with another porous material in combination with the organosilica material.

24. The method of claim 23, wherein the another porous material is a microporous material, a mesoporous material, an analogous periodic mesoporous material, a metal oxide, carbon, or a combination thereof.

25. The method of claim 24, wherein the another porous material is a zeolite material.

26. The method of claim 1, wherein the organosilica material is packed into a column and the lube base stock is contacted therein.

27. The method of claim 1, wherein separation of the aromatic compound from the lube base stock produces an at least partially purified lube base stock.

* * * * *